United States Patent
Silpe et al.

(10) Patent No.: US 12,209,256 B2
(45) Date of Patent: Jan. 28, 2025

(54) SYSTEM FOR PROTEIN INACTIVATION AND RECOMBINANT PHAGES FOR TARGETED BACTERIAL KILLING, INFECTION, BIODETECTION, AND AS A MEANS OF PROTEIN EXTRACTION

(71) Applicant: The Trustees of Princeton University, Princeton, NJ (US)

(72) Inventors: Justin E. Silpe, Lawrenceville, NJ (US); Bonnie L. Bassler, Princeton, NJ (US)

(73) Assignee: THE TRUSTEES OF PRINCETON UNIVERSITY, Princeton, NJ (US)

(*) Notice: Subject to any disclaimer, the term of this patent is extended or adjusted under 35 U.S.C. 154(b) by 767 days.

(21) Appl. No.: 17/289,336

(22) PCT Filed: Oct. 31, 2019

(86) PCT No.: PCT/US2019/059133
§ 371 (c)(1),
(2) Date: Apr. 28, 2021

(87) PCT Pub. No.: WO2020/092748
PCT Pub. Date: May 7, 2020

(65) Prior Publication Data
US 2022/0010284 A1  Jan. 13, 2022

Related U.S. Application Data

(60) Provisional application No. 62/754,143, filed on Nov. 1, 2018.

(51) Int. Cl.
*C12N 7/00* (2006.01)
*C12N 15/73* (2006.01)
*C12N 15/74* (2006.01)

(52) U.S. Cl.
CPC .............. *C12N 7/00* (2013.01); *C12N 15/73* (2013.01); *C12N 15/74* (2013.01); *C12N 2795/10121* (2013.01); *C12N 2795/10122* (2013.01)

(58) Field of Classification Search
None
See application file for complete search history.

(56) References Cited

U.S. PATENT DOCUMENTS

| | | | | |
|---|---|---|---|---|
| 4,833,080 | A * | 5/1989 | Brent | C07K 14/39 435/317.1 |
| 10,047,405 | B2 * | 8/2018 | Kotula | C12N 15/73 |
| 10,837,004 | B2 * | 11/2020 | Cady | C12N 9/22 |
| 11,174,486 | B2 * | 11/2021 | Hasty | A61K 35/74 |
| 2007/0014770 | A1 * | 1/2007 | Holland | A61P 17/00 435/235.1 |
| 2012/0027786 | A1 | 2/2012 | Gupta et al. | |
| 2013/0121967 | A1 * | 5/2013 | Leah | A61P 31/04 435/235.1 |
| 2015/0237870 | A1 * | 8/2015 | Pei | C12N 9/18 435/235.1 |
| 2015/0322440 | A1 | 11/2015 | Chang et al. | |
| 2016/0312313 | A1 | 10/2016 | Kotula et al. | |
| 2018/0148729 | A1 | 5/2018 | Hasty et al. | |

FOREIGN PATENT DOCUMENTS

WO   WO-2017177196 A1 * 10/2017  ............. A01N 63/00

OTHER PUBLICATIONS

Borysowski, J., Lobocka, M., Miedzybrodzki, R., Weber-Dabrowska, B., & Górski, A. (2011). Potential of Bacteriophages and Their Lysins in the Treatment of MRSA. BioDrugs: Clinical Immunotherapeutics, Biopharmaceuticals, and Gene Therapy, 25(6), 347-355. (Year: 2011).*
Lan, S. F., Huang, C. H., Chang, C. H., Liao, W. C., Lin, I. H., Jian, W. N., Wu, Y. G., Chen, S. Y., & Wong, H. C. (2009). Characterization of a new plasmid-like prophage in a pandemic Vibrio parahaemolyticus O3:K6 strain. Applied and environmental microbiology, 75(9), 2659-2667. (Year: 2009).*
International Search Report and Written Opinion for corresponding PCT Application No. PCT/US2019/059133, dated Jan. 31, 2020.

* cited by examiner

*Primary Examiner* — Janet L Andres
*Assistant Examiner* — Carey Alexander Stuart
(74) *Attorney, Agent, or Firm* — MEAGHER EMANUEL LAKS GOLDBERG & LIAO, LLP

(57) ABSTRACT

Recombinant phages that infect and kill bacterial hosts in response to user-defined inputs are provided. The components that encode the user-defined inputs can be combined, such that multiple inputs are maintained on a single recombinant phage, enabling precise control over the targeting strategy. The phages can be engineered to kill a specific bacterial species or multiple species simultaneously. Recombinant phages can also be engineered to harbor fluorescent and bioluminescent reporter genes that enable them to be used for tracking, detection, and in biosensing applications. Recombinant phages can also be used to lyse bacterial cells that produce recombinant proteins, as a rapid method to enable extraction and high-level purification of potentially valuable and/or industrially important proteins. Systems are provided that can be used to control the activity of a protein of interest, by taking advantage of an interaction between Qtip and a phage repressor protein.

30 Claims, 7 Drawing Sheets
Specification includes a Sequence Listing.

SYSTEM FOR PROTEIN INACTIVATION AND RECOMBINANT PHAGES FOR TARGETED BACTERIAL KILLING, INFECTION, BIODETECTION, AND AS A MEANS OF PROTEIN EXTRACTION

CROSS REFERENCE TO RELATED APPLICATIONS

This application claims priority to U.S. Provisional Application No. 62/754,143 filed Nov. 1, 2018, which is hereby incorporated in its entirety by reference.

STATEMENT REGARDING FEDERALLY SPONSORED RESEARCH OR DEVELOPMENT

This invention was made with government support under Grant No. GM065859 awarded by the National Institutes of Health and Grant No. MCB-1713731 awarded by the National Science Foundation. The government has certain rights in the invention.

SEQUENCE LISTING

The present application is being filed along with a Sequence Listing in electronic format. The Sequence Listing is provided as a file entitled PRIN-65376_ST25.TXT, created Oct. 30, 2019, which is approximately 57,889 bytes in size. The information in the electronic format of the Sequence Listing is incorporated herein by reference in its entirety.

FIELD OF THE INVENTION

The present invention is drawn to systems and methods for protein inactivation and controlling phage lytic programs, and in particular, systems and methods that utilize a regulator of a phage lytic gene, wherein the engineered recombinant phage is capable of responding to a host-produced quorum-sensing autoinducer.

BACKGROUND

Bacteria use the cell-cell communication process called quorum sensing (QS) to coordinate group behaviors. QS depends on the production, release, and group-wide detection of signal molecules called autoinducers (AI).

In bacteria, virulence factors and the emergence of toxigenic subtypes from non-toxigenic strains can often be traced back to phages (Waldor and Friedman, 2005). Indeed, interaction with phages is thought to have significantly contributed to overall bacterial evolution (Faruque and Mekalanos, 2012). *V. cholerae* has provided insight into how phages have shaped their pathogenic hosts. The gene encoding the major *V. cholerae* virulence factor CTX, is located on the genome of the lysogenic CTXφ temperate phage (Waldor and Mekalanos, 1996). Only *V. cholerae* strains harboring CTXφ cause epidemic and pandemic cholera disease (Faruque and Mekalanos, 2012). Thus, while *V. cholerae* is considered the causative agent of cholera, the etiology must also include the CTXφ phage.

Much of our understanding of temperate phage biology stems from seminal work on phage lambda (Ptashne, 2004). Upon infection, temperate phages can lyse the host cell and propagate, or they can lysogenize the host cell and remain dormant as prophages. In lambda, this fate determination switch is governed by the status of a single protein, the lambda cI repressor (Ptashne, 2004). If present in abundance, cI represses phage lytic genes and commits the phage to the lysogenic program. If cI is limiting or absent, for example, following inactivation due to the host stress response (SOS), repression is relieved, phage lytic genes are expressed, and the host cell is lysed. Evidence that phages may exploit cues beyond host cell stress to drive the lysogeny-lysis switch has only recently been demonstrated in a phage-phage communication process, coined the arbitrium system (Erez et al., 2017). Briefly, SPbeta phage encode a peptide that they produce upon infection of *Bacillus*. The peptide is detected by prophages in neighboring cells via a phage-encoded receptor. The phage peptide-receptor pair repress lysis across the population.

Although desirable, a system that has the capacity to control lysis and respond to host-produced QS AI has never been created.

BRIEF SUMMARY

A first aspect of the disclosed invention is drawn to an engineered recombinant phage that is capable of responding to a host-produced quorum-sensing autoinducer and includes a first DNA construct configured to drive a phage lytic program for a first bacterium, where at least one regulator of a phage lytic gene is subject to a promoter. Optionally, the engineered recombinant phage includes a component from a phage that is specific to a second bacterium different from the first bacterium. Optionally, a regulator of the phage lytic gene is a phage protein, such as Qtip (quorum triggered inactivator of cI protein). Optionally, a regulator of the phage lytic gene is a non-phage protein. Optionally, a regulator of a phage lytic gene encodes a repressor or an antirepressor. Optionally, the promoter is activated by a specific species of bacteria. Optionally, the phage has been modified such that it does not respond to any of its native biological inputs.

Optionally, the promoter is configured to configured to be light-activated via a photoresponsive transcription factor, or activated by the presence of a chemical species such as a small molecule, a metabolite, or an artificial inducer.

Optionally, the engineered recombinant phage includes a plurality of DNA constructs, such as: (i) a second DNA construct configured to prevent a phage lytic program, where the second genetic construct has at least one regulator of a phage lytic gene subject to a promoter; or (ii) a second DNA construct configured to lyse bacteria producing recombinant proteins.

A second aspect of the disclosed invention is drawn to a method for selectively lysing a bacterium. The method includes providing a disclosed engineered recombinant phage, contacting a target bacterium with the phage, and allowing the phage to lyse the bacterium.

A third aspect of the disclosed invention is a prophylactic treatment method for a high-risk individual. The method includes introducing the disclosed engineered recombinant phages, which are delivered by commensal bacteria to the high-risk individual prior to coming in contact with a pathogenic bacterium. The engineered recombinant phage includes a first DNA construct configured to drive a phage lytic program for the pathogenic bacterium, and where at least one regulator of a phage lytic gene is subject to a promoter that is activated by the pathogenic bacterium. Optionally, the promoter is induced by an external trigger or activated by a cue that is specifically produced by the pathogenic bacterium.

A fourth aspect of the disclosed invention is a method for manufacturing an engineered recombinant phage. The method includes providing a first gene adapted to drive a phage lytic program, and providing a first promoter, then integrating the first gene under the first promoter on a plasmid such that the phage is capable of responding to a host-produced quorum-sensing autoinducer. Optionally, the method includes removing a natural lytic regulatory component of the phage, modifying the phage such that it does not respond to any of its native biological inputs, or a combination thereof. Optionally, the first gene, the first promoter, or both comprises either synthetic DNA or transgenic DNA.

Optionally, the integration is accomplished by a method selected from the group consisting of: in-vitro or in-vivo transposon mutagenesis, homologous recombination promoted by natural competence mechanisms or a suicide vector, recombineering with the lambda red system, restriction enzyme-based cloning or isothermal assembly, and genome editing using transcription activator-like effector nucleases (TALENs), zinc-finger nucleases (ZFNs), or clustered regulatory interspaced short palindromic repeat (CRISPR-Cas) based procedures.

A fifth aspect of the disclosed invention is an engineered recombinant phage that includes a DNA construct with a reporter tag, such as a fluorescent or luminescent reporter tag, subject to a promoter, wherein the phage is capable of responding to a host-produced quorum-sensing autoinducer.

A sixth aspect of the disclosed invention is a system for inactivating a protein of interest. The system includes a first promoter controlling expression of a qtip (quorum triggered inactivator of cI protein) gene, and a second promoter, such as a natural promoter of the protein of interest, controlling expression of a gene that encodes a phage repressor protein fused to a protein of interest, configured such that the phage repressor protein is capable of being inactivated when Qtip is expressed and interacts with the phage repressor protein. Optionally, the first promoter may be activated by a specific species of bacteria, light-activated via a photoresponsive transcription factor, or activated by the presence of a chemical species such as a small molecule, a metabolite, or an artificial inducer.

A seventh aspect of the disclosed invention is a method for controlling the activity of a protein of interest, that includes providing a system as previously described. Then, producing (i) a fusion protein containing the phage repressor protein fused to a protein of interest by expressing the gene that encodes the phage repressor protein fused to a protein of interest, and (ii) a Qtip protein by inducing expression of the qtip gene at a point in time after the fusion protein is produced. The Qtip protein is then allowed to inactivate the phage repressor protein.

DETAILED DESCRIPTION

Figure 1A:
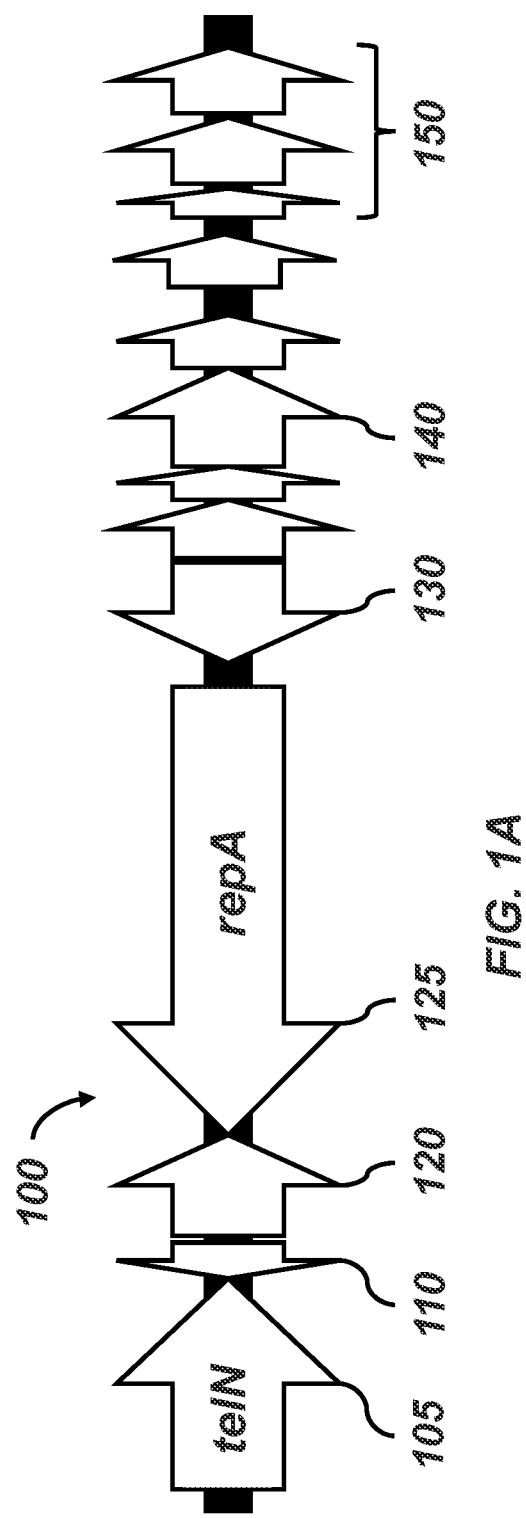
FIG. 1A is a representation of the organization of a region of the phage VP882 genome.

The term "conservative substitution" as used herein refers to an amino acid replacement in a protein that changes a given amino acid to a different amino acid with similar biochemical properties (e.g. charge, hydrophobicity and size).

The term "homology" as used herein refers to a degree of identity. There may be partial homology or complete homology. A partially identical sequence is one that is less than 100% identical to another sequence.

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "pharmaceutically acceptable" as used herein with respect to an amount or substance means that an amount or substance which is, within the scope of sound medical judgment, suitable for use in contact with the tissues of humans and lower animals without undue toxicity, irritation, allergic response, and the like, commensurate with a reasonable benefit/risk ratio, and effective for the intended use when the substance is used in a pharmaceutical composition.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

The term "protein" or its interchangeably used term "polypeptide" as used herein refer to a molecule composed of monomers (amino acids) linearly linked by amide bonds (also known as peptide bonds). Post-translational modifications of the polypeptide, for example, glycosylations, acetylations, phosphorylations, and the like are also encompassed. The terms "protein" or "polypeptide" also includes variants which should encompass any polypeptide comprising, or alternatively or preferably consisting of, any natural or genetically engineered polypeptide having more than 70%, preferably more than 80%, even more preferably more than 90%, again more preferably more than 95%, and most preferably more than 97% amino acid sequence identity with the sequence of the polypeptide. Preferred methods of generating a variant of a polypeptide is by genetic engineering, preferably by insertion, substitution, deletion or a combination thereof.

The term "recombinant" as used herein with respect to a polypeptide or protein means that a polypeptide or protein is derived from recombinant (e.g., microbial or mammalian) expression systems, where "microbial" refers to recombinant polypeptides or proteins made in bacterial or fungal (e.g., yeast) expression systems.

A first aspect of the disclosed invention is drawn to an engineered recombinant phage that is capable of responding to a host-produced quorum-sensing autoinducer and includes a first DNA construct configured to drive a phage lytic program for a first bacterium, where at least one regulator of a phage lytic gene is subject to a promoter.

Host-produced quorum-sensing autoinducer. The host-produced quorum-sensing autoinducer can include any known to those of skill in the art, including but not limited to 3,5-dimethylpyrazine-2-ol (DPO), cholera autoinducer-1 (CAI-1), autoinducer-2 (AI-2), N-acyl homoserine lactones, and autoinducing peptides.

Regulator of a phage lytic gene. Any regulator of a phage lytic gene known to those of skill in the art may be used, including, but not limited to VqmA, HapR, LuxR, VpsT, LasR, RhlR, EL222, AraC, LacI, TetR, HilA, and CRP. In some embodiments, the regulator of the phage lytic gene is a phage protein, such as Qtip. Qtip is a small (79 amino acid) protein [SEQ ID NO.: 1] that aggregates and inactivates the VP882 repressor of lysis.

In some embodiments, the regulator of the phage lytic gene is a non-phage protein.

In some embodiments, the recombinant phage may include one or more additional phage lytic genes, which may utilize a component from a phage that is specific to a second bacterium that is different from the first bacterium. That is, one of skill in the art can produce a recombinant phage that can drive a lytic program in two or more species of bacteria, by putting different regulators under one or more promoters.

In some embodiments, the at least one regulator of a phage lytic gene encodes a repressor known to those of skill in the art, including, but not limited to phage repressors, cI-like repressors, LexA-like repressors, and TetR-type repressors. In some embodiments, the at least one regulator of a phage lytic gene encodes an antirepressor known to those of skill in the art, including, but not limited to Qtip, Ant, Tum, and RstC.

In some embodiments, the page can include a plurality of DNA constructs, such as a second DNA construct configured to prevent a phage lytic program, the second DNA construct having at least one regulator of a phage lytic gene subject to a promoter. The recombinant phage may include a second DNA construct configured to lyse bacteria producing recombinant proteins.

Promoter. The promoter may be any appropriate promoter known to those of skill in the art. In some embodiments, the promoter is activated by a specific species of bacteria, such that expression of the promoter-controlled gene is restricted to the specific species of bacteria. In some embodiments, the promoter is configured to be light-activated via a photoresponsive transcription factor, such as the EL222 bacterial transcription factor (a photosensor LOV domain and a Helix-Turn-Helix (HTH) DNA-binding domain), where in the dark, the LOV domain binds the HTH domain, blocking dimerization and DNA binding, while blue light illumination produces structural changes that allow the EL222 to dimerize and bind DNA.

In some embodiments, the promoter is configured to be activated by the presence of a chemical species, such as a small molecule, a metabolite, or an artificial inducer.

In some embodiments, the phage has been modified such that it does not respond to any of its native biological inputs.

As an example, the vibriophage, VP882 has the capacity to respond to a host-produced QS AI. The VP882 phage-encoded protein, Gp56, which as used herein is named as VqmA$_{Phage}$, is a viral DPO binding QS receptor and transcription factor with homology to the *Vibrio* QS receptor VqmA. DPO, via VqmA$_{Phage}$, activates the phage lytic program via induction of expression of a phage gene that, as used herein, is named Op (quorum triggered inactivator of cI protein). Qtip is a small (79 amino acid) protein [SEQ ID NO.: 1] that aggregates and inactivates the VP882 repressor of lysis. DPO-bound VqmA$_{Phage}$ recognizes the *V. cholerae* vqmR promoter whereas *V. cholerae* VqmA is unable to recognize the phage qtip promoter. This "one-sided conversation" enables the VP882 prophage to influence host QS while executing its own lifestyle programs with immunity from host interference. Thus, this is a novel phage-encoded receptor that senses a host-produced AI to mediate the lysis-lysogeny decision.

Phages related to VP882 encode DNA-binding transcription factors and small proteins in the identical genomic locations as VP882 vqmA$_{Phage}$ and qtip, respectively. Qtip aggregates the repressors from these phages but not the distant, prototypical lambda repressor. In the opposite vein, the protein encoded in the qtip location in one of these other phages, despite having no similarity to Qtip, can induce aggregation of the VP882 repressor. Thus phages, in addition to VP882, control their lysis-lysogeny decisions by tuning into host-produced signaling factors using a Qtip-like lysis de-repression mechanism. The VP882 phage can be reprogrammed to be insensitive to native inputs but responsive to user-defined cues. These reprogrammable "kill-switches" could be useful for environmental, industrial, and medical applications.

*V. cholerae* VqmA (denoted VqmA$_{Vc}$) is a dual QS receptor-transcription factor. Predicted VqmA homologs consisted of C-terminal DNA-binding domains and N-terminal PAS-domains, presumably for binding the ligand, DPO. To identify other DPO-binding proteins, a bioinformatic search was performed for proteins possessing the PAS fold-4 subtype domain (InterPro, IPR013656) present in *V. cholerae* VqmA$_{Vc}$. Of the 103,219 returned proteins, only one was in the virus category, Gp56 of the Myoviridae virus VP882, a non-integrating temperate phage from a pandemic *V. parahaemolyticus* 03:K6 strain. VP882 infects vibrios including *V. parahaemolyticus* and *V. cholerae*, however, the GC content of the VP882-encoded gp56 is markedly higher than host encoded vqmA genes (55.5% in phage VP882 versus 46.5% and 47.5% in *V. parahaemolyticus* and *V. cholerae*, respectively) suggesting the phage gene was not directly transferred from the *Vibrio* host. Referring to FIG. 1A, telN (105) and repA (125) are conserved across linear plasmid-like phage. In addition, gp55 (110) encodes the Qtip antirepressor, gp56 (120) encodes the VqmA$_{Phage}$ QS receptor, gp59 (130) encodes the cI repressor, gp62 (140) encodes the Q antiterminator, and gp69-71 (150) encode the lysis genes.

Examination of the 38.2 kb VP882 genome (100) shows that gp56 (120) lies between repA (125) and telN (105); two essential genes conserved across all known linear phage, which are required for replication and maintenance as linear plasmids, respectively. The curious location of gp56 (120), hereafter called VqmA$_{Phage}$, within a critical region of the phage genome, suggested that it too might be essential for some crucial phage-related process.

Figure 1B:
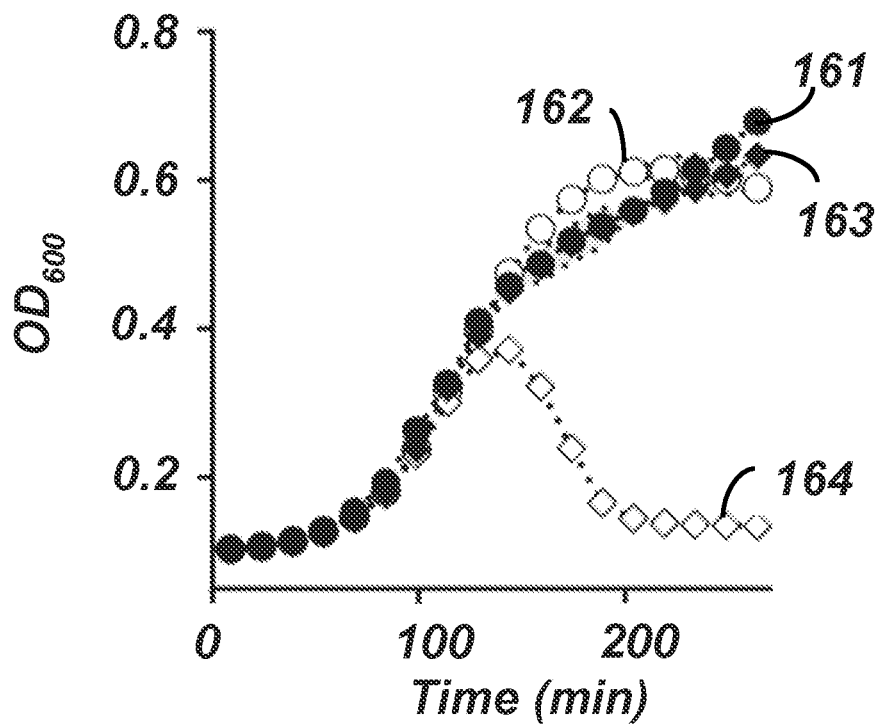
FIG. 1B is a graph of growth curves of $V.$ $parahaemolyticus$ lysogenized with phage VP882 (163, 164) or cured of phage VP882 (161, 162) harboring inducible $vqmA_{Phage}$, where, as applicable, $vqmA_{Phage}$ expression was induced with 0.2% ara.

VqmA$_{Phage}$ induces host cell lysis. To study the function of VqmA$_{Phage}$, vqmA$_{Phage}$ was cloned onto a vector under an arabinose inducible promoter and introduced it into the *V. parahaemolyticus* clinical isolate in which the phage was originally discovered. Referring to FIG. 1B, induction of VqmA$_{Phage}$ caused a precipitous decline in optical density (OD$_{600}$) following initial growth in strains having the prophage (163, 164), suggesting that VqmA$_{Phage}$ promotes cell lysis. A similar effect occurred when the original *V. parahaemolyticus* isolate carrying the VP882 phage was exposed to the DNA damaging agent mitomycin C (MMC), a known inducer of lytic development for many temperate phages including VP882. To determine if the effect of VqmA$_{Phage}$ was a phage-dependent process, the *V. parahaemolyticus* host was cured of the VP882 phage using plasmid incompatibility. Arabinose-induction of vqmA$_{Phage}$ in the *V. parahaemolyticus* strain lacking the prophage (FIG. 1B, 162) did not cause lysis.

FIG. 1B shows growth curves of *V. parahaemolyticus* lysogenized with phage VP882 (163, 164) or cured of phage VP882 (161, 162) harboring inducible vqmA$_{Phage}$, where As indicated, vqmA$_{Phage}$ expression was induced with 0.2% ara.

Consistent with this result, induction of vqmA$_{Phage}$ in bacterial hosts that do not harbor the VP882 prophage (*Escherichia coli, V. cholerae*, and a different isolate of *V. parahaemolyticus*) also did not cause lysis. Thus, VqmA$_{Phage}$ promotes host cell lysis in a phage-dependent manner.

MMC treatment, in addition to lysing the host, leads to production of VP882 phage particles and their release into culture fluids. Indeed, VP882 phage DNA could be purified from culture fluids of MMC-treated but not untreated *V. parahaemolyticus* harboring phage VP882. Induction of VqmA$_{Phage}$ in *V. parahaemolyticus* harboring phage VP882 also results in release of phage DNA. Phage DNA could not be isolated if the phage was defective for the major capsid gene (gp07::Tn5). These results demonstrate that VqmA$_{Phage}$, like MMC, launches the complete phage VP882 lytic cycle.

Figure 1C:
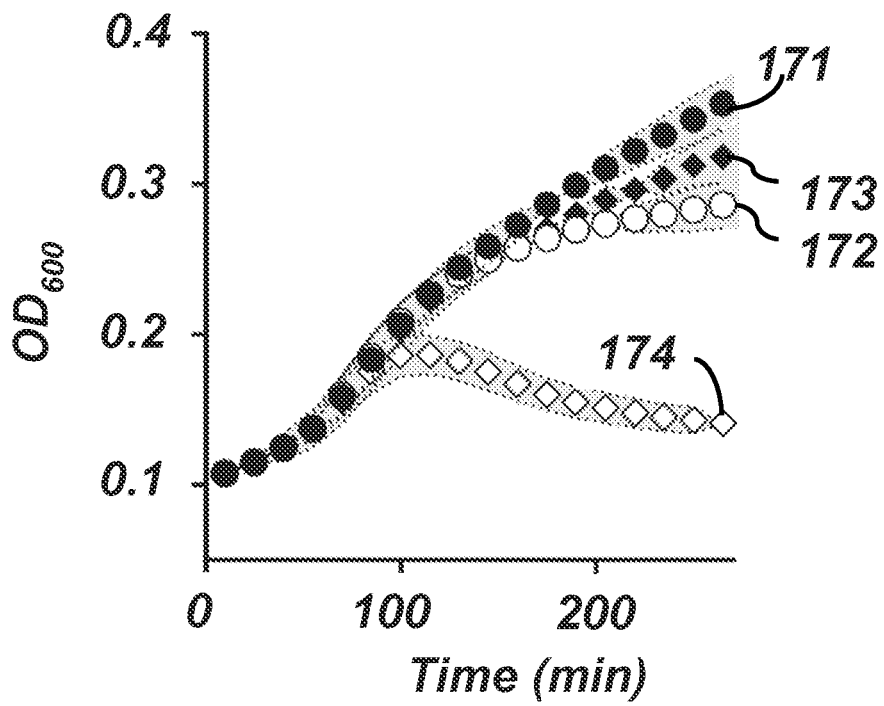
FIG. 1C is a graph of growth curves of $V.$ $parahaemolyticus$ lysogenized with phage VP882 harboring inducible $vqmA_{Phage}$ in minimal medium lacking threonine, where, as applicable, $vqmA_{Phage}$ expression was induced with 0.2% ara and DPO was present at 10 µM.

VqmA$_{Phage}$ is activated by the quorum-sensing autoinducer DPO. VqmA$_{Vc}$ and DPO were originally discovered as a QS receptor-AI pair in *V. cholerae* where they control biofilm formation and virulence factor production. Maximal transcriptional activation of the direct target of VqmA$_{Vc}$, vqmR, occurs only when VqmA$_{Vc}$ is bound to DPO. A phage genome that encodes a VqmA homolog suggests that VqmA$_{Phage}$ activity could likewise be modulated by DPO. Vibrios produce DPO from threonine so growth in minimal medium lacking threonine eliminates DPO production, including in a lysogenized *V. parahaemolyticus* strain used as part of a study discussed herein. In the absence of DPO, induction of VqmA$_{Phage}$ in the *V. parahaemolyticus* caused a low, basal level of cell lysis, whereas maximal host cell lysis occurred when DPO was supplied. See FIG. 1C, where vqmA$_{Phage}$ expression was induced with 0.2% ara (172, 174) and DPO was present at 10 μM (173, 174). As seen, no lysis occurred when DPO was added in the absence of induction of VqmA$_{Phage}$. Thus, DPO drives VqmA$_{Phage}$ activity.

Figure 1D:
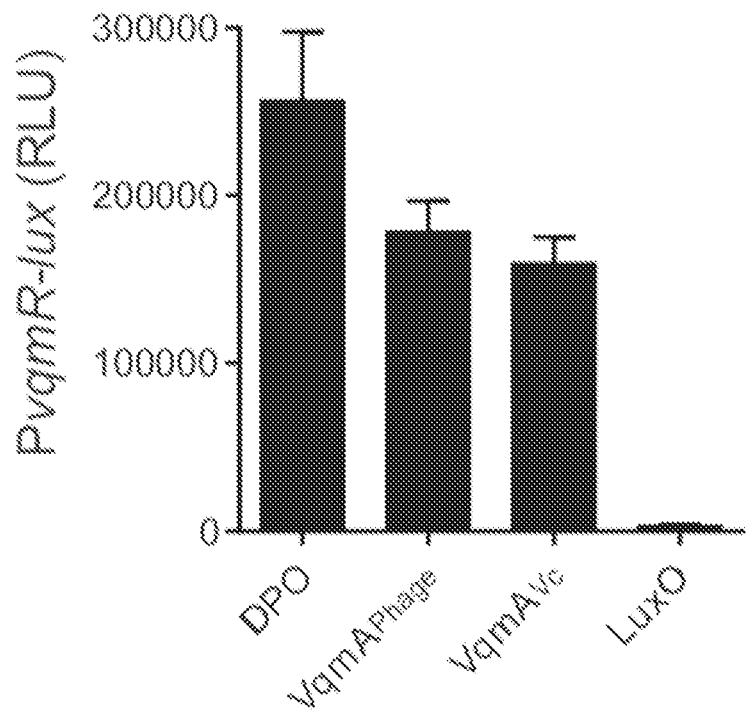
FIG. 1D is a graph showing the quantitation, in relative light units (RLU), of DPO from purified proteins in a DPO-dependent $E.$ $coli$ reporter assay, where the left bar shows the 10 µM synthetic DPO standard, and the other bars, from left to right, reflect $VqmA_{Phage}$, $VqmA_{Vc}$, and LuxO.
Figure 1E:
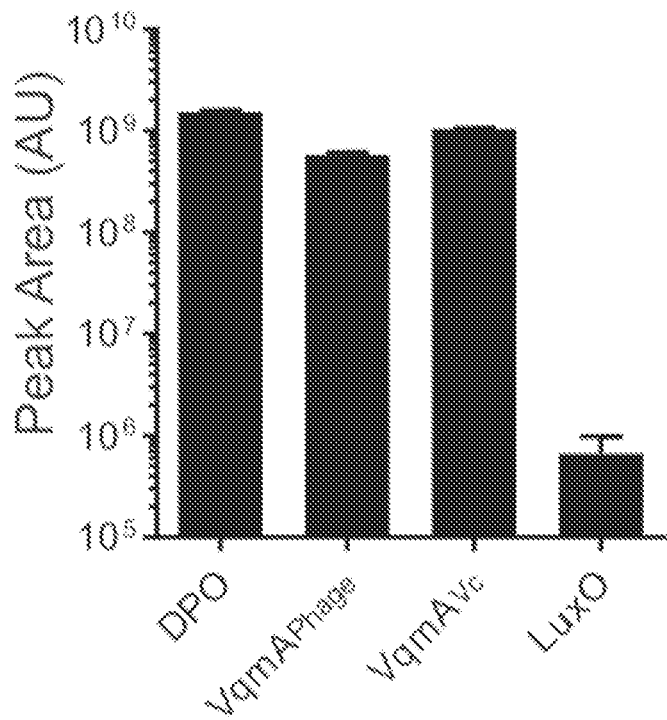
FIG. 1E is a graph showing the quantitation, in arbitrary units (AU), of DPO from the extracts in FIG. 1D by LC-MS, showing results from (from left to right) 100 µM synthetic DPO standard, $VqmA_{Phage}$, $VqmA_{Vc}$, and LuxO.

To explore whether DPO acts directly on VqmA$_{Phage}$, the VqmA$_{Phage}$ protein from *E. coli* was overexpressed and purified. Importantly, *E. coli* naturally produces DPO. VqmA$_{Vc}$ was also overexpressed and purified. As a control, *V. cholerae* LuxO, a DNA-binding QS transcription factor that does not bind DPO, was overexpressed and purified. The three proteins were denatured, removed from suspension, and the remaining soluble fractions were extracted and assessed for DPO content by bioassay and liquid chromatography-mass spectrometry (LC-MS). Synthetic DPO was used as the standard. Referring to FIG. 1D, the extracts made from the two VqmA proteins yielded activity in the DPO bioassay whereas the LuxO protein yielded none. Referring to FIG. 1E, the major component released from VqmA$_{Vc}$ and VqmA$_{Phage}$ was DPO. Indeed, one thousand-fold more DPO was present in each of the VqmA protein extracts than in the LuxO extract, which yielded the background level of DPO. Thus, VqmA$_{Phage}$ binds to and is activated by the quorum-sensing autoinducer DPO, which promotes the phage lytic lifecycle.

Lytic development in phage VP882 is sensitive to at least two inputs, DNA damage and QS. The first input, DNA damage, leads to proteolysis of the phage VP882 cI repressor, which occurs in a host RecA-dependent fashion and requires no other phage components. QS constitutes the second input and involves the production of the bacterial host cell density-dependent factor, DPO, to activate a phage-dependent process consisting of VqmA$_{Phage}$-induced expression of qtip; ber.

Without wishing to be held to a particular theory, two feedback mechanisms that could amplify VqmA$_{Phage}$ production, once initiated. First, VqmA$_{Phage}$ activates its own expression. Second, phage plasmid copy number increases in the absence of cI similar to the plasmid-like phage N15. Qtip-directed inactivation of cI thus elevates phage copy number, increasing the pool of vqmA$_{Phage}$ and qtip DNA that can be transcribed. Aided by these two mechanisms, it is suspected that low-level production of VqmA$_{Phage}$, triggered by some environmental stimulus or unstable state, is sufficient to drive the phage lysis program.

DNA damage and quorum-sensing control phage lysis via activation of expression of the gene encoding the Q antiterminator. It can be seen that cI directly represses the gene encoding the antiterminator Q, and cI is cleaved upon DNA damage, which launches the phage lysis program. DPO-driven QS, mediated by VqmA$_{Phage}$, also launches the phage lysis program. The occurrence of these two phage regulatory systems in the context of the natural *V. parahaemolyticus* host can be connected.

First DNA damage: MMC was added to the *V. parahaemolyticus* lysogen harboring a plasmid carrying a reporter for the antiterminator Q (Pq-lux) or a reporter for its target operon (Pgp69-lux). Light production rapidly increased with a 10-minute offset between activation of Pq-lux and activation of Pgp69-lux. The delay between the two reporters was consistent with a model in which the antiterminator Q is produced first and, only after, and as a consequence of Q production, are genes involved in lysis expressed.

Second QS: Light output from *V. parahaemolyticus* lysogens carrying either Pq-lux or Pgp69-lux and also the arabinose inducible VqmA$_{Phage}$ construct was monitored. Thirty minutes after arabinose addition, light production from the Pq-lux reporter occurred. Ten minutes later, light production commenced from the Pgp69-lux reporter. Again, this shows that q expression occurs prior to genes for lysis. The time delay in the QS experiment roughly matches the delay in the MMC experiment. Thus, DNA damage-induced lysis and QS-induced lysis converge at the point of activation of expression of q, after which, Q activates gp69 irrespective of which input launched the program.

VqmA$_{Phage}$ activates expression of a gene encoding an antirepressor. VqmA$_{Phage}$ could act in one of three ways to initiate the Q-directed phage lysis program: by directly activating q expression, by directly repressing cI expression, thereby de-repressing q, or by indirectly repressing cI, again leading to de-repression of q. To distinguish between these possibilities, VqmA$_{Phage}$ was produced from one plasmid in *E. coli* and Pq-lux expression was monitored from a second plasmid in *E. coli*. No change in light production occurred, excluding the first possibility that VqmA$_{Phage}$ directly activates q expression. To this system, a third plasmid carrying the phage cI gene was introduced. cI repressed Pq-lux expression, but again, no effect on reporter activity occurred when vqmA$_{Phage}$ was expressed, eliminating the second possibility that VqmA$_{Phage}$ directly represses cI. To investigate the third possibility, that an additional, VqmA$_{Phage}$-controlled intermediate component exists linking VqmA$_{Phage}$ to repression of cI and subsequent de-repression of q, the lysis-defective phage carrying Tn5 in q was introduced into *E. coli* harboring the plasmid with inducible vqmA$_{Phage}$ and the Pq-lux reporter plasmid. Addition of arabinose to this strain resulted in a twenty-fold increase in Pq-lux output, indicating that an element encoded on the phage is required to connect VqmA$_{Phage}$ to cI expression.

To identify the gene that VqmA$_{Phage}$ controls, a recombinant *E. coli* strain carrying arabinose inducible vqmA$_{Phage}$, Pq-lux, and the cI repressor gene on a single plasmid was made. Into this strain, a library of phage genomic fragments on a vector were introduced. The transformants were screened for those that activated Pq-lux expression following induction of vqmA$_{Phage}$. One ~600 bp phage genomic fragment that was sufficient (denoted "Active Fragment") was identified. This fragment mapped to a region immediately upstream of the vqmA$_{Phage}$ locus and harbored only one complete ORF (gp55) of 240 bp. This was verified by electromobility shift assays (EMSA) that the VqmA$_{Phage}$ protein binds phage DNA immediately upstream of gp55.

To show that Gp55 (Qtip) links VqmA$_{Phage}$ to cI repression and, in turn, to q de-repression, the gp55 ORF was cloned under a tetracycline inducible promoter on a plasmid (pTetA-gp55) and introduced it into the *E. coli* strain harboring the above combined reporter. Induction of gp55 was sufficient to generate Pq-lux activity. The pTetA-gp55 construct was introduced into the *V. parahaemolyticus* strain harboring the VP882 lysogen. Induction of gp55 expression caused host cell lysis comparable to when MMC was added or vqmA$_{Phage}$ was induced. These results indicate that Gp55 (Qtip) is the effector connecting QS to de-repression of q to the triggering of host cell lysis.

Gp55 (Qtip) is a 79 amino acid protein with no predicted domains and no significant homology to any protein in the NCBI database. The small size and lack of a DNA-binding domain implies that Gp55 may act post-translationally on cI. To test this, HALO-cI and HIS-Gp55 were individually produced from plasmids in recombinant *E. coli*, collected and combined the cell pellets from the two strains, lysed the cells, and purified the HIS-Gp55 protein. It was seen that cI binds to Gp55 during purification and that the effect of Gp55 on q promoter activity occurs only when cI is present. These results suggest that Gp55 is an antirepressor, which acts directly on the cI repressor and prevents cI from binding to q promoter DNA.

To explore the Qtip mechanism of inactivation of cI in vivo, HALO-cI protein localization was monitored at the single-cell level in *E. coli*. In the absence of Qtip, the cI protein was uniformly dispersed in the cytoplasm. Production of Qtip caused cI to form foci located primarily at the cell poles and Qtip colocalizes with cI suggesting that Qtip drives aggregation of the cI repressor. By contrast, in MMC-treated cells, the cI protein remained diffuse indicating that cleavage of cI does not cause foci formation. Thus, both the QS and DNA damage inputs eliminate cI activity, derepress q, and cause lysis, however, their underlying mechanisms of action are different: DNA damage stimulates cI cleavage, whereas VqmA$_{Phage}$—directed QS produces Qtip, which inactivates the cI repressor via aggregation.

The Qtip mechanism is reminiscent of small phage antirepressors such as those from coliphage P1, 186, and N15 which engage in non-covalent interactions with partner repressor proteins, thereby, inhibiting repressor activity. However, unlike in phage VP882, the promoters driving these antirepressors are LexA-controlled, indicating they are induced exclusively by DNA-damage, not by QS.

Figure 2:
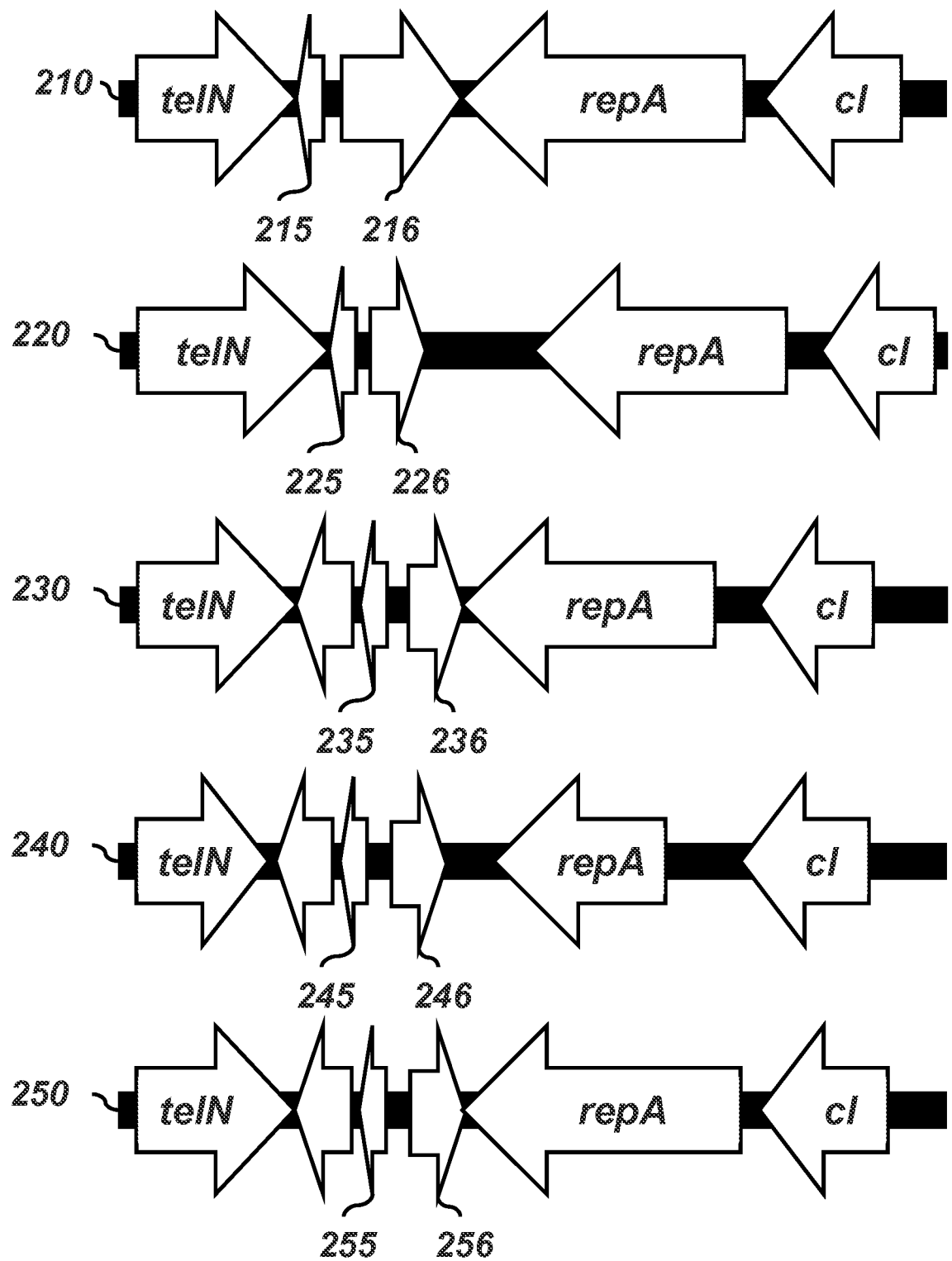
FIG. 2 is a syntenic comparison of the regions of plasmid-like phages VP882 (NC_009016.1), MJ1, Vp58.5 (NC_027981.1), VHML (NC_004456.1), and vB_VpaM_MAR (NC_019722.1) between the telN and repA loci.

Referring to FIG. 2, while VqmA$_{Phage}$ (216) and Qtip (215) appear unique to phage VP882 (210), their locations in the phage VP882 genome, between two essential genes present in plasmid-like phages (telN and repA), allows for the prediction (using informatics, etc.) of ORFs with putative DNA binding domains and predict ORFs that encode Qtip-like proteins in the identical locations in other plasmid-like phage genomes. Examination of one such phage, MJ1 (220), shows that its Qtip-like protein, ORF$_{584}$ (225) [SEQ ID NO.: 2], can substitute for Qtip, sequester a non-cognate repressor protein, albeit with a different sub-cellular localization, and launch the phage VP882 lysis program. By contrast, Qtip and ORF$_{584}$ do not function with the distantly-related lambda repressor. Other qtip-like domains (235, 245, 255) can be seen in VP58.5 (230), VHML (240), and vB_VpaM_MAR (250).

With respect to vibriophage, the antirepressor, RstC, encoded by the CTX satellite phage RS1, which is integrated into some *V. cholerae* genomes induces aggregation of multiple RstR repressor variants that share little identity (Davis et al., 2002). Davis hypothesized that RstC recognizes a common structural motif in the RstR proteins. Similarly, Qtip can aggregate multiple repressor proteins, and moreover, different Qtip-like antirepressors with little amino acid identity can aggregate the same phage repressor protein.

An asymmetric binding pattern was uncovered: VqmA$_{Phage}$ binds its own (qtip) and host (vqmR) target promoters, whereas VqmA$_{Vc}$ only binds its own (vqmR) target promoter. The lack of sequence similarity between PvqmR [SEQ ID NO.: 3] and Pqtip [SEQ ID NO.: 4], coupled with the ability of VqmA$_{Phage}$ to bind both, can represent a strategy by which the VP882 phage can tune-in and respond to host QS, while maintaining the ability to execute its own Qtip-mediated lysis-lysogeny pathway without host interference.

Database analyses show that *V. cholerae* strain FORC 055, has two CRISPRs matching regions of the VP882 genome (AATCGAAAAAGAGCTCCGCGGCGACCTGTTCCA [SEQ ID NO.: 5]) suggesting that *V. cholerae* is vulnerable to phage VP882 and needs to defend itself.

Further, phage-*Vibrio* interactions could occur during human infection. For example, *V. cholerae* encounters the host and associated microbiota upon infection. DPO is produced by the host microbiota from the threonine-rich resource, mucin, and DPO represses *V. cholerae* biofilm formation and virulence. Thus, the human host and its microbiota "team up" to defend against *V. cholerae* using DPO. DPO is also produced and detected by *V. cholerae* leading to dispersal, a crucial step in the *V. cholerae* lifecycle because it maximizes dissemination to new hosts. It is envisioned that a phage also uses DPO to trigger dissemination, in this case, via host *V. cholerae* cell lysis at high host-cell population density. This strategy likely maximizes phage infection of the next *V. cholerae* cell. Thus, interactions across the eukaryotic, bacterial, and viral kingdoms all rely on one QS AI, DPO. Presumably, each entity in these combined beneficial and parasitic partnerships is garnering the information encoded in the DPO molecule to optimize its survival and reproduction.

gp62 is the VqmA$_{Phage}$-controlled gene required for lysis. To identify phage genes required for lysis, in vitro Tn5 mutagenesis was used. Individual mutant phage were introduced into the phage-cured *V. parahaemolyticus* host harboring arabinose inducible vqmA$_{Phage}$ where they were assessed for the ability/inability to lyse the host when arabinose was added. Phage mutants with insertions in gp62 were defective for lysis. By contrast, a phage carrying a Tn5 insertion immediately downstream of gp62 had the wild-type (WT) lysis phenotype. In trans expression of gp62 restored lysis to *V. parahaemolyticus* carrying the VP882 phage harboring gp62::Tn5. These results show that Gp62 is necessary for phage-mediated host lysis.

Epistasis analysis was used to define the relationship between VqmA$_{Phage}$ and Gp62. In trans expression of gp62 caused lysis in strains carrying either the wild-type VP882 phage or a VP882 phage with a Tn5 in vqmA$_{Phage}$. By contrast, in trans expression of vqmA$_{Phage}$ in a strain carrying the VP882 phage harboring gp62::Tn5 was lysis defective. Thus, Gp62 acts downstream of vqmA$_{phage}$. Consistent with this finding, strains carrying VP882 phage harboring vqmA$_{phage}$::Tn5 lyse upon MMC treatment, whereas strains carrying VP882 phage harboring gp62::Tn5 do not. These results suggest that DNA damage—mediated by Gp62—and QS communication—mediated by DPO, VqmA$_{Phage}$, and Gp62—constitute two distinct triggers that promote phage VP882-induced host cell lysis.

Figure 3A:
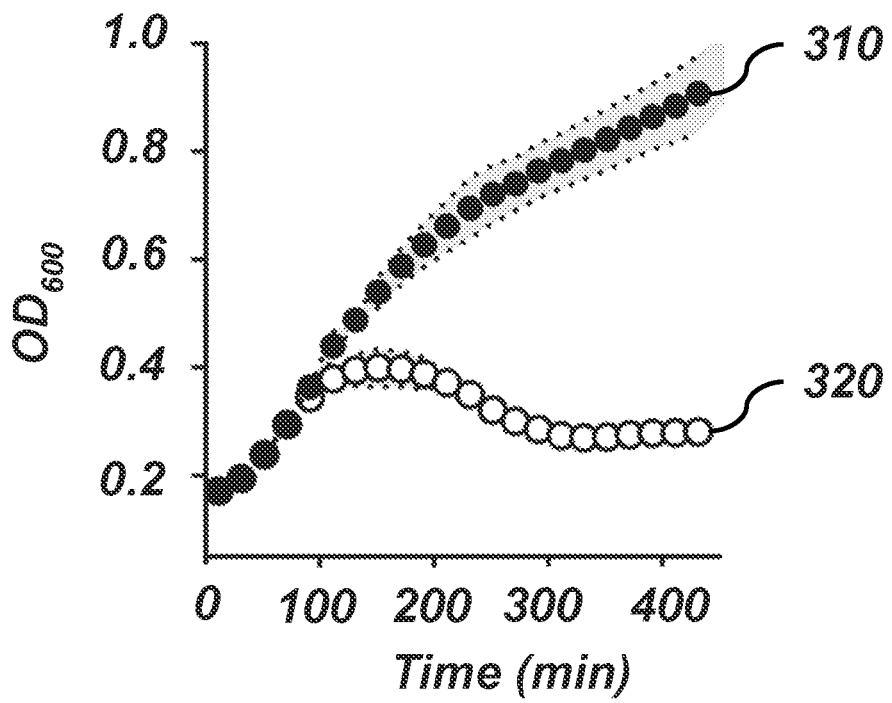
FIG. 3A is a graph showing the growth of $E.$ $coli$ carrying arabinose inducible 69-71 on a plasmid in medium lacking (black, 310) or containing (white, 320) 0.4% arabinose.

Gp62 is a phage antiterminator and Gp70 is a lysin.

gp62 is predicted to encode a protein similar to Q from the lambdoid bacteriophage 82 (pairwise BLAST E-value, 5e-19; 30% identity), suggesting that Gp62 is likely a regulator of phage lytic genes. To determine what Gp62 controls, a region ~1 kb downstream of gp62 encoding a three-gene operon (gp69-71, ref. 150 in FIG. 1A) was focused on. Four observations motivated this: First, the gp69-71 5'UTR harbors at least one rho-independent terminator, suggesting an antiterminator mechanism. Second, gp70 encodes a protein with a lysozyme domain. Third, qRT-PCR showed that the gp69-71 operon is not expressed by the phage carrying the gp62::Tn5 mutation but is upregulated more than 500-fold prior to lysis when gp62 is present. Fourth, introduction and induction of the gp69-71 operon was sufficient to cause lysis of *E. coli* lacking any other phage genes. FIG. 3A is a graph showing the growth of *E. coli* carrying arabinose inducible 69-71 on a plasmid in medium lacking (black, 310) or containing (white, 320) 0.4% arabinose.

Figure 3B:
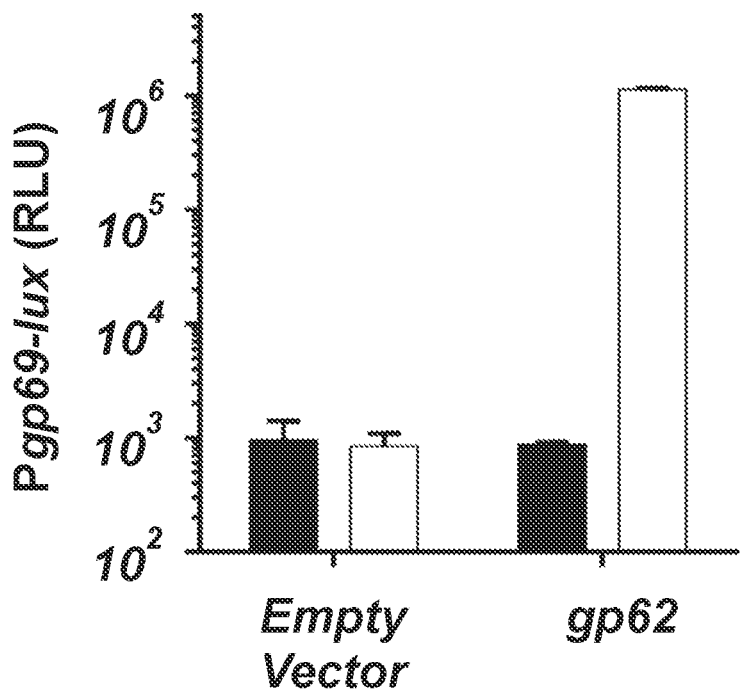
FIG. 3B is a graph showing the relative luminescence units (RLU) of an $E.$ $coli$ carrying a plasmid with Pgp69-lux and a second empty plasmid or the plasmid with arabinose inducible gp62, where the black bars indicate no arabinose, and the white bars indicate 0.2% arabinose.

To explore the link between Gp62 and gp69-71 a Pgp69-lux transcriptional fusion was engineered that included the putative antiterminator sequence. Referring to FIG. 3B, in recombinant *E. coli*, production of Gp62 protein was sufficient to activate the expression of the Pgp69-lux fusion. Thus, the gp69-71 promoter/terminator is likely the direct target of Gp62. As used herein, Gp62 may be referred to as Q.

Gp59 is a phage lysis repressor.

Figure 3C:
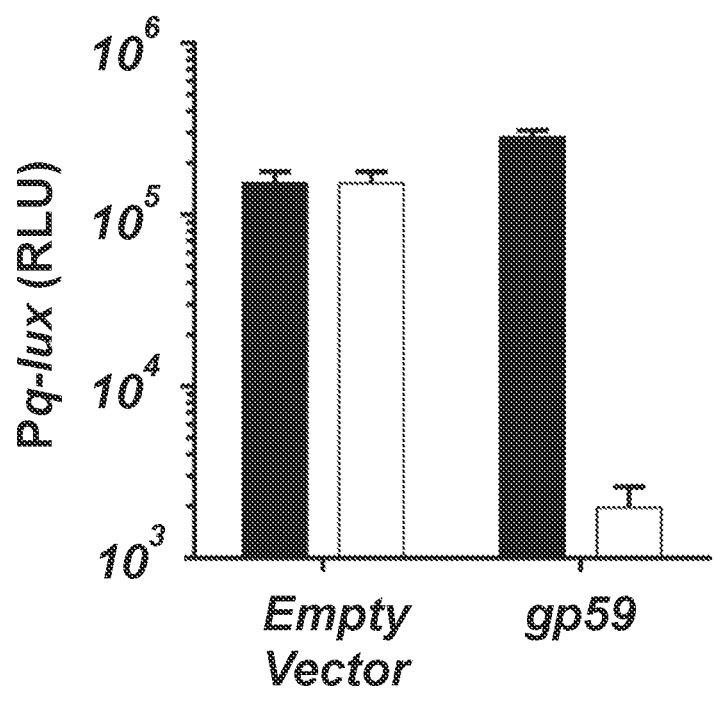
FIG. 3C is a graph showing the Pq-lux expression from $E.$ $coli$ carrying an empty plasmid or the plasmid with arabinose inducible gp59, where the black bars indicate no arabinose, and the white bars indicate 0.2% arabinose.

The results show that the Q antiterminator is required for phage-driven lysis. Q can be kept in check to enable the lysogenic state. To explore regulation, a Pq-lux transcriptional fusion was made. Twenty-five-fold more light was produced from this fusion in the *V. parahaemolyticus* strain that had been cured of the phage than in the strain carrying the phage, suggesting that the prophage encodes a repressor of Pq that promotes lysogeny. An ORF, gp59, predicted to encode a DNA-binding repressor similar to cI (pairwise BLAST E-value, 5e-22; 37% identity) is located adjacent to but in the opposite orientation of the operon encoding the q gene. In trans expression of gp59 repressed Pq-lux in *V. parahaemolyticus*. Moreover, Gp59 repression of Pq is likely direct. Referring to FIG. 3C, in recombinant *E. coli*, arabinose-induction of gp59 is sufficient to repress Pq-lux output 140-fold. Thus, Gp59 is the phage VP882 repressor of lysis.

Like lambda cI, Gp59 can be cleaved during the RecA-activated SOS response, which can explain how MMC induces VP882 phage-mediated lysis. A functional HIS-HALO-Gp59 protein fusion was generated and its fate in untreated and MMC-treated recA$^+$ and ΔrecA *E. coli* cells was followed. Western blot revealed a single band of the expected size (~60 kDa) in the untreated samples and lower-molecular-weight bands, presumably cleavage products, in the MMC-treated recA$^+$ sample. The HIS-HALO-Gp59 protein in the ΔrecA sample was unaffected by MMC treatment, suggesting that RecA is required for MMC-mediated cleavage of Gp59. Consistent with this result, addition of MMC to recA$^+$*E. coli* carrying the Pq-lux reporter plasmid and HIS-HALO-Gp59 led to a significant increase in light production, whereas if the *E. coli* was ΔrecA, MMC had no effect. These results suggest that Gp59 is subject to cleavage in a DNA-damage (MMC) and host-SOS response (recA) dependent manner, and moreover, that the activating effect of MMC on Pq coincides with this cleavage. As used herein, Gp59 may be referred to as cI.

Phage Qtip-type proteins and their host partner repressor proteins are conserved.

Databases for possible cI partners were scanned, and multiple putative repressors were identified, from VP882, MJ1, VP58.5, vB_VpaM_MAR, VHML, and lambda. One within the Gram-negative marine bacterium, *Marinobacterium jannaschii* DSM 6295 showed the cl-like gene was located on a previously unreported ~35 kb contig with predicted repA and telN genes nearby. The repA gene from this element was confirmed as functional by PCR amplification of the repA locus, ligation to an antibiotic resistance cassette, and demonstration that the resulting vector was maintained as a plasmid in *E. coli*. The primers used were JSO-0897 (GAATACACTCCTTGTAAGTGATTGT-TATAAGGAGC [SEQ ID NO.: 6]) and JSO-0899 (TGTTC-GATAATTATTTGGTCTTCGGTCATTTTTCC [SEQ ID NO.: 7]) for VP882 and JSO-1279 (CCACGGAATAG-GAGGTGTTTAG [SEQ ID NO.: 8]) and JSO-1280

(GAGGGATATCCATTACGCCAG [SEQ ID NO.: 9]) for MJ1. This result suggested that *M. jannaschii* is lysogenized with a VP882-like phage that harbors the cI-like gene. We hereafter refer to this element as phage MJ1. Co-expression of phage VP882 Qtip with HALO-cI from MJ1 resulted in foci. Aggregation also occurred when Qtip was co-expressed with a HALO-cI repressor from another vibriophage, VP58.5. No aggregation occurred when phage VP882 Qtip was co-expressed with lambda HALO-cI (FIG. 4F). Lambda cI has less similarity to the VP882, MJ1, and VP58.5 cI proteins than the three proteins have to one another (Figure S4D). Thus, Qtip sequesters closely-related but not distantly-related phage repressors.

The region intervening the phage MJ1 telN and repA genes lacks a predicted vqmA$_{Phage}$ gene. Rather, there is an ORF encoding a different, putative transcription factor. Adjacent to that ORF, encoded in the opposite orientation, is a small gene (orf584). This arrangement exactly parallels the genomic organization of phage VP882 qtip-vqmA$_{Phage}$. Despite orf584 and qtip having no detectable sequence similarity, it was expected that phage MJ1 orf584 encodes a protein with a Qtip-like function. Phage MJ1 orf584 was cloned and induced, and it caused aggregation of phage MJ1 cI and phage VP882 cI but not lambda cI. ORF$_{584}$ leads to a stripe of cI localization along the length of the cell, whereas Qtip leads to foci at the poles. Like Qtip, ORF$_{584}$ is sufficient to disrupt cI repressor activity, as its induction leads to de-repression of phage VP882 Pq expression and lysis of *V. parahaemolyticus* lysogenized with phage VP882. These results suggest that ORF$_{584}$ and Qtip are functionally analogous: they induce aggregation of their native and related phage repressors, launching the phage lysis programs.

The genomes of nine linear plasmid-like phages were inspected. VP882, MJ1, VP58.5, VHML, vB_VpaM_MAR, N15, PY54, pKO2, and PhiHAP1. In 5 of the 9 cases, in the qtip-vqmA$_{phage}$ location, small genes and oppositely-oriented ORFs with strongly predicted DNA-binding domains could be identified (see FIG. 2). Only phage VP882 harbors an obvious VqmA$_{Phage}$ homolog; it is speculated that these additional phage-encoded DNA binding proteins respond to other host-produced cues to activate transcription of their partner genes encoding Qtip-like antirepressors.

VqmA$_{Phage}$ can substitute for VqmA$_{Vc}$ but not the reverse.

VqmA-directed QS has only been studied in *V. cholerae*, where VqmA$_{Vc}$, DPO, VqmR, and the downstream targets were discovered (Liu et al., 2006; Papenfort et al., 2015, 2017). Therefore, the VP882 prophage was transferred to *V. cholerae*.

It was first tested whether VqmA$_{Phage}$ could replace VqmA$_{Vc}$. As a control we show that, as expected, a ΔvqmA$_{Vc}$ *V. cholerae* strain carrying a PvqmR-mKate2 reporter produces no fluorescence because VqmA is required for activation of vqmR expression (FIG. 5A and Papenfort et al., 2015). Reintroduction of vqmA$_{Vc}$ or introduction of vqmA$_{phage}$ on a plasmid restored expression of PvqmR-mKate2 showing that vqmA$_{Phage}$ complements the *V. cholerae* ΔvqmA$_{Vc}$ mutation. Using EMSAs, it was found that both VqmA$_{Vc}$ and VqmA$_{Phage}$ bind the *V. cholerae* vqmR promoter. By contrast, while VqmA$_{Phage}$ activates a Pqtip-lux reporter and VqmA$_{Phage}$ binds qtip promoter DNA, *V. cholerae* VqmA does neither. Consistent with this finding, arabinose induction of vqmA$_{Vc}$ does not trigger lysis of *V. cholerae* carrying the VP882 prophage while vqmA$_{Phage}$ does (FIG. 5D). Thus, at least with respect to the tests we have performed, VqmA$_{Phage}$ can substitute for *V. cholerae* VqmA$_{Vc}$, but the reverse is not the case; *V. cholerae* VqmA$_{Vc}$ cannot carry out VqmA$_{Phage}$ functions. To summarize the results: Regulation of the phage VP882 lysis-lysogeny switch relies on the presence of one of two inputs, DNA damage or host DPO. The latter functions through VqmA$_{Phage}$. The consequences of DPO regulation of VqmA$_{Phage}$ is activation of phage lysis genes via Qtip, cI, and Q as well as possible modulation of the host QS output via activation of PvqmR.

Host QS Controls the Phage VP882 Lytic Cycle

The results show that DPO, in conjunction with VqmA$_{Phage}$, drives the phage VP882 lysis-lysogeny decision. If so, host QS should influence the phage lifecycle. To verify this idea, a mutant VP882 phage carrying vqmA$_{Phage}$-$e$::Tn5 was introduced into wild-type and Δtdh *V. cholerae*, each carrying the vector encoding arabinose-inducible vqmA$_{Phage}$. This strategy restricted VqmA$_{Phage}$ production to that from the inducible promoter on the plasmid. The *V. cholerae* growth over time was measured by OD$_{600}$ and phage production (viral load) was measured by quantitative PCR of viral preparations made from identical cultures that were grown in parallel to those from which the growth data was obtained. The Δtdh *V. cholerae* strain underwent minimal lysis and there was less than a 3-fold-change in viral load following induction of vqmA$_{Phage}$. By contrast, induction of vqmA$_{Phage}$ caused WT *V. cholerae* to lyse and viral load to increase 15-fold relative to when vqmA$_{Phage}$ was not induced. Thus, the VP882 phage fate switch can be driven by endogenously produced host DPO. We also supplied synthetic DPO to the WT and Δtdh strains. In this case, lysis occurred, and viral load increased in both strains to similar extents. Moreover, in the WT strain, 25% more lysis occurred, and viral load increased an additional 35% when exogenous DPO was provided compared to when only endogenously-produced DPO was present (FIGS. 6B and 6C). Thus, given a fixed amount of VqmA$_{Phage}$, DPO becomes the determining factor controlling lysis by the phage.

To decouple QS regulation from Qtip-directed inactivation of cI, qtip was produced from an inducible promoter, thus bypassing the need for VqmA$_{Phage}$. Near-complete lysis and increased viral production occurred in both the WT and Δtdh strains in response to qtip expression and both processes were insensitive to DPO. Similar results were obtained when MMC was added instead of induction of qtip, suggesting that, at least under these test conditions, inactivation of cI by Qtip or by RecA-assisted cleavage promotes the same outcomes to the host and the phage populations. However, input from Qtip enables the phage lysis-lysogeny decision to be connected to the cell density of the host.

Phage VP882 as a QS-activated kill switch.

The plasmid-like nature of phage VP882 allows it to be maintained in non-native hosts via its endogenously-encoded replication machinery. Among the limited number of plasmid-like prophages that have been discovered, phage VP882 is unique in that it also encodes a receptor for a host-produced QS AI, which is shown to activate the phage lytic cycle. This singular arrangement allows one to explore possibilities for synthetic control of VP882 with the goal of generating a recombinant phage with highly specific, quorum-controlled lytic triggers.

In contrast to the widespread production of DPO by diverse bacteria, the response to DPO, consisting of DPO binding to VqmA and activation of the vqmR promoter is, as far as is known, limited to the *Vibrio* genus. This asymmetry was exploited to design a *V. cholerae*-specific phage kill switch. To do this, the VP882 phage q gene was cloned under the *V. cholerae* vqmR promoter (called PvqmR-q) on a plasmid. This plasmid was introduced into *E. coli* and *V. cholerae* each lysogenized with the identical lysis-defective phage carrying a Tn5 in the q gene. Introduction of the plasmid carrying PvqmR-q did not alter growth of *E. coli*. However, no colonies could be recovered from *V. cholerae* suggesting that Q protein, made as a consequence of DPO-VqmA$_{Vc}$-directed activation of the vqmR promoter, killed the *V. cholerae* recipient. In contrast to the WT parent, no growth defect/no lysis occurred if the host was ΔvqmA *V. cholerae*. Indeed, ~5 orders of magnitude more colonies were recovered from the ΔvqmA *V. cholerae* strain verifying that VqmA$_{Vc}$ is required to transduce the DPO information to the vqmR-q promoter on the phage.

To test for cross-activation of the *V. cholerae* vqmR-based kill switch in other vibrios, the plasmid with PvqmR-q was introduced into *V. parahaemolyticus* and *V. vulnificus* strains lysogenized with the lysis-defective phage VP882 harboring q::Tn5. The same number of colonies were recovered following introduction of the PvqmR-q kill switch or a control plasmid, despite the fact that both *V. parahaemolyticus* and *V. vulnificus* naturally encode vqmA homologs and they make DPO. Moreover, the number of colonies recovered in both cases was 5 orders of magnitude higher than when the killing module was introduced into *V. cholerae*. This result is interpreted to mean that *V. parahaemolyticus* and *V. vulnificus* VqmA cannot recognize the *V. cholerae* vqmR promoter, and, therefore, they do not activate PvqmR-q expression and, in turn, the downstream lytic functions. Taken together, the PvqmR-q construct is recognized in a *V. cholerae* VqmA$_{Vc}$-specific manner and thus, this construct only kills *V. cholerae*, not closely related vibrios.

Phage VP882 kill switches specific for other pathogens.

To demonstrate the modularity of the species-specific kill switch, it was engineered to target a human pathogen unrelated to vibrios, *Salmonella typhimurium*. InvF is a transcriptional activator of genes encoding proteins essential for *S. typhimurium* pathogenicity. invF is indirectly activated by the HilD transcription factor. Specifically, HilD activates expression of hilA, encoding a second transcription factor, HilA, that directly activates expression of invF. The invF promoter was fused to the phage q gene (PinvF-q) and introduced the construct on a plasmid into *S. typhimurium* lysogenized with phage VP882 harboring q::Tn5, and also carrying a plasmid with tetracycline inducible hilD (pTetA-hilD). This *S. typhimurium* strain grew without defect, showing that q is not expressed. Addition of low level aTc (2 ng mL$^{-1}$) to induce hilD, caused a dramatic decline in growth. Isogenic *S. typhimurium* strains containing the PinvF-q and pTetA-hilD plasmids but lacking the VP882 phage or with pTetA-hilD and the phage, but lacking the PinvF-q plasmid were unaffected by aTc. These results show that *S. typhimurium* killing is phage- and kill switch-dependent.

These results demonstrate that one can exploit phage VP882 q::Tn5 as a template, and by exchanging the promoter driving q expression, one can engineer phage kill switch systems that are specific for different bacterial species. In some embodiments, plasmids were used to carry the PvqmR and PinvF to facilitate testing in different hosts lysogenized with the q::Tn5 phage mutant. However, these fusions can be integrated onto the phage VP882 genome, making the recombinant phage the only required element for the kill switch. Finally, as several points of regulation have been uncovered within the phage lytic program, including the repressor cI and three activators, VqmA$_{Phage}$, Qtip, and Q that function upstream and downstream of the cI repressor, it is envisioned that one could program phages to contain different logic circuits and multiple input dependencies.

Strains, DNA, Protein, and DPO Techniques

Unless otherwise indicated, *E. coli, V. cholerae, V. parahaemolyticus*, and *V. vulnificus* were grown with aeration in Luria-Bertani (LB-Miller, BD-Difco) broth at 37° C. Low salt LB (Lennox) broth was used for *S. typhimurium*, and *M. jannaschii* was grown in Marine Broth 2216 (BD-Difco) at room temperature. M9 minimal medium supplemented with 200 mM NaCl (for *V. parahaemolyticus* and *V. cholerae*) was used where indicated. Strains used are listed in Table 1.

TABLE 1

Strains used.

| Strain | Genotype |
|---|---|
| *Vibrios* | |
| *V. cholerae* | Wild-type C6706 |
| *V. cholerae* (KPS-842) | str. C6706, Δtdh |
| *V. cholerae* (KPS-661) | str. C6706, PvqmR-mKate2, PmicX-sfgfp::lacZ |
| *V. cholerae* (KPS-662) | str. C6706, ΔvqmA/PvqmR-mKate2, PmicX-sfgfp::lacZ |
| *V. parahaemolyticus* BB22OP | Wild-type |
| *V. parahaemolyticus* O3:K6 | Wild-type, phage VP882 lysogen |
| *V. vulnificus* | Wild-type |
| *E. coli* | |
| BL21(DE3) | *E. coli* str. B, F- ompT hsdSB (rBmB-) gal dcm (DE3) |
| BLR(DE3) | *E. coli* str. B, F- ompT hsdSB(rB- mB-) gal lac ile dcm Δ(srl- recA)306::Tn10 (tetR)(DE3) |
| BW25113 | lacIq, rrnBT14, ΔlacZWJ16, hsdR514, ΔaraBADAH33, ΔrhaBADLD78, tdh::kanR |
| T7Express lysY/Iq | *E. coli* str. B, MiniF lysY lacIq(CamR)/fhuA2 lacZ::T7 gene1 [lon] ompT gal sulA11 R(mcr-73::miniTn10-TetS)2 [dcm] R(zgb- 210::Tn10-TetS) endA1 Δ(mcrC-mrr) 114::IS10 |

TABLE 1-continued

Strains used.

| Strain | Genotype |
|---|---|
| TOP10 | F- mcrA Δ(mrr-hsdRMS-mcrBC) φ80lacZΔM15 ΔlacX74 recA1 araD139 Δ(ara-leu)7697 galU galK λ- rpsL(StrR) endA1 nupG |
| TransforMax EC100D pir+ | F- mcrA Δ(mrr-hsdRMS-mcrBC) φ80dlacZΔM15 ΔlacX74 recA1 endA1 araD139 Δ(ara, leu)7697 galU galK λ- rpsL (StrR) nupG pir+(DHFR) |
| *S. typhimurium* | Wild-type |
| *M. jannaschii* | Wild-type DSM 6295, ATCC 27135 |

Unless otherwise noted, antibiotics, were used at: 50 U mL$^{-1}$ polymyxin B (Pb, Sigma), 100 μg mL$^{-1}$ ampicillin (Amp, Sigma), 100 μg mL-1 kanamycin (Kan, GoldBio), 80 μg mL-1 Zeocin (Zeo, Thermo), and 5 μg mL$^{-1}$ or 10 μg mL$^{-1}$ chloramphenicol (Cm, Sigma). Cm concentration was 10 μg mL$^{-1}$ when it was the only antibiotic present and 5 μg mL$^{-1}$ when used in conjunction with other antibiotics. When multiple plasmids were simultaneously present within a single strain, care was exercised to limit the number of passages. Inducers were used as follows: *E. coli:* 250 ng mL$^{-1}$ mitomycin C (MMC, Sigma), 100 ng mL$^{-1}$ anhydrotetracycline (aTc, Clontech), 0.2% L-arabinose (ara, Sigma), 0.5 mM Isopropyl β-D-1-thiogalactopyranoside (IPTG, GoldBio). Vibrios: 50 ng mL$^{-1}$ MMC, 10 ng mL$^{-1}$ aTc, 0.2% ara. *S. typhimurium:* 2 ng mL$^{-1}$ aTc. The HIS-VqmA$_{Phage}$, HIS-VqmA$_{Vc}$, and HIS-LuxO proteins were produced and purified as described (Papenfort et al., 2017), with the exception that HIS-VqmA$_{Vc}$ was treated with thrombin CleanCleave (Sigma) post-purification. DPO was analyzed for bioactivity as described (Papenfort et al., 2017), with the exception that a different reporter strain was used, see table 2, below.

TABLE 2

Plasmids Used.

| Plasmids used | Organism |
|---|---|
| pJES-052 | *V. parahaemolyticus* VP882 lysogen and cured |
| pJES-052 | *V. parahaemolyticus* VP882 lysogen and cured |
| [pKP-367 + pJES-045] | BW25113 tdh::kanR *E. coli* |
| pJES-095; pKP-445; pWN-001 | proteins from BL21(DE3) *E. coli* |
| pJY-014; pJES-052; pJES-093; [JSP-003 + pJY-014]; [JSP-003 + pJES-052]; [JSP-003 + pJES-093]; [JSP-002 + pJY-014]; [JSP-002 + pJES-052]; [JSP-002 + pJES-093] | *V. parahaemolyticus* VP882 lysogen |
| [JSP-024 + pJY-014]; [JSP-024 + pJES-052]; [JSP-024 + pJES-093]; [JSP-003 + pJY-014]; [JSP-003 + pJES-052]; [JSP-003 + pJES-093] | *V. parahaemolyticus* VP882 lysogen |
| pJES-087 | TOP10 *E. coli* |
| [pJES-105 + pJY-014]; [pJES-105 + pJES-093] | TOP10 *E. coli* |
| pJES-097; [pJES-097 + pJES-174] | *V. parahaemolyticus* VP882 lysogen and cured |
| [pJES-104 + pJY-014]; [pJES-104 + pJES-159] | TOP10 *E. coli* |
| pJES-134 | BLR(DE3) and T7Express *E. coli* |
| [pJES-097 + pJES-134] | BLR(DE3) and T7Express *E. coli* |
| [pJES-104 + pJY-014]; [pJES-105 + pJY-014]; [pJES-104 + pJES-052]; [pJES-105 + pJES-052] | *V. parahaemolyticus* VP882 lysogen |
| [pJES-130 + pXB-300]; [pJES-130 + pJES-133]; [pJES-130 + pJES-141] | TOP10 *E. coli* |
| pJY-014; pJES-052; pJES-143 | *V. parahaemolyticus* VP882 lysogen |
| pJES-147; pJES-157; pJES-154 | proteins from BL21(DE3) *E. coli* |
| [pJES-143 + pJES-134]; [pJES-143 + pJES-156] | T7Express *E. coli* |
| [pJES-166 + pJES-134] | T7Express *E. coli* |
| Upper: [pJES-143 + pJES-134]; [pJES-143 + pJES-150]; [pJES-143 + pJES-151]; Lower: [pJES-153 + pJES-134]; [pJES-153 + pJES-150]; [pJES-153 + pJES-151] | T7Express *E. coli* |
| pJES-143; pJES-153 | *V. parahaemolyticus* VP882 lysogen |
| pJY-014; pJES-023; pJES-052 | KPS-662 *V. cholerae* |
| pKP-445; pJES-095 | proteins from BL21(DE3) *E. coli* |
| [pJES-119 + pJES-052]; [pJES-101 + pJES-052]; [pJES- 119 + pKP-375]; [pJES-101 + pKP-375] | TOP10 *E. coli* |
| [JSP-002 + pKP-375]; [JSP-002 + pJES-052] | *V. cholerae* |

TABLE 2-continued

Plasmids Used.

| Plasmids used | Organism |
| --- | --- |
| [JSP-024 + pJES-052]; [JSP-024 + pJES-143] | V. cholerae and KPS-842 V. cholerae |
| [JSP-024 + pJES-052]; [JSP-024 + pJES-143] | V. cholerae and KPS-842 V. cholerae |
| [JSP-003 + pJES-117] | V. cholerae, KPS-662 V. cholerae, V. ON vulnificus, V. parahaemolyticus VP882 lysogen |
| [pJES-171 + pJES-167]; [JSP-003 + pJES-171]; [JSP-003 + pJES-171 + pJES-167] | S. typhimurium 14028 |
| pJES-052 | V. parahaemolyticus VP882 lysogen and cured |
| none | V. parahaemolyticus VP882 lysogen and cured |
| pJES-052 | TOP10 E. coli, V. cholerae, V. parahaemolyticus BB22OP, V. parahaemolyticus VP882 lysogen |
| JSP-1270 | V. parahaemolyticus VP882 lysogen and cured |
| pKP-445; pWN-001; pJES-095 | proteins from BL21(DE3) E. coli |
| pJES-052; [JSP-003 + pJES-052] | V. parahaemolyticus VP882 lysogen |
| [pJES-052 + pJES-128 + pJES-125]; [pJES-052 + pJES- 128 + pJES-140] | TransforMax EC-100D E. coli |
| [pJES-104 + pJES-052]; [pJES-104 + pJES-052 + pJES- 174]; [pJES-104 + pJES-052 + JSP-003] | TOP10 E. coli |
| pJES-095 | TOP10 E. coli |
| [pJES-143 + pJES-140]; [pJES-143 + pJES-158] | proteins from BL21(DE3) E. coli |
| pJES-174; pJES-173 | TOP10 E. coli |
| [pJES-143 + pJES-134]; [pJES-143 + pJES-150]; [pJES- 143 + pJES-148]; [pJES-143 + pJES-151] | T7Express E. coli |
| [pJES-104 + pJES-143]; [pJES-104 + pJES-153] | TOP10 E. coli |
| [JSP-024 + pJES-143] | V. cholerae and KPS-842 V. cholerae |
| [JSP-003 + pJY-014]; [JSP-003 + pJES-117] | TOP10 E. coli |
| [pJES-120 + pJES-052] | TOP10 E. coli |
| pJES-174; pJES-177; pJES-176; pJES-175 | TOP10 E. coli |

Liquid Chromatography-Mass Spectrometry for DPO Detection

Standards were prepared in 50% MeOH. Samples and standards were loaded onto a 1 mm×75 mm C12 column (ACE 3 C18 PFP, Mac-Mod) using a Shimadzu HPLC system and PAL auto-sampler (20 µL per injection) at a flow rate of 70 µL min$^{-1}$. The column was maintained at 45° C. using a column oven. The column was connected inline to an electrospray source coupled to an LTQ-Orbitrap XL mass spectrometer (Thermo). Caffeine (2 pM µL$^{-1}$ in 50% acetonitrile with 0.1% formic acid) was injected as a lock mass through a tee at the column outlet using a syringe pump at 45 µL min$^{-1}$ (Harvard PHD 2000). Chromatographic separation was achieved with a linear gradient from 1% to 45% B in 6 min (A: 0.1% formic acid, B: 0.1% formic acid in acetonitrile) with an initial 1 min hold at 1% B and followed by 4 min wash at 100% B and equilibration for 8 min with 1% B (total 20 min program). Electrospray ionization was achieved using a spray voltage of 4.50 kV aided by sheath gas (Nitrogen) at a flow rate of 12 (arbitrary units) and auxiliary gas (Nitrogen) flow rate of 1 (arbitrary units). Full scan MS data were acquired in the Orbitrap at a resolution of 60,000 in profile mode from the m/z range of 110-220. Raw files were imported into Skyline v4.1 (MacCoss Lab) and peak areas for DPO were extracted using the small molecule workflow.

Cloning Techniques

Primers and dsDNA (gene blocks) used for plasmid construction are listed in Tables 3 and 4, respectively, both obtained from Integrated DNA Technologies. Plasmids are listed in Table S3. The publicly available VP882 annotations associated with the available sequence (NC_009016.1; (Lan et al., 2009)) were used for reference and cloning with the exception of cI and q (gp59 and gp62, respectively), which, based on experimental characterization and sequence alignments, were deemed to start 27 codons downstream from the currently annotated start site of cI (gp59) and 39 codons downstream from the currently annotated start site of q (gp62). Gibson assembly, intramolecular reclosure, and traditional cloning methods, including blunt and restriction enzyme-based cloning, were employed for all cloning (see Table 5). PCR with Q5 High Fidelity Polymerase was used to generate insert and backbone DNA. Primer pairs and templates are described in Table 5. Gibson assembly relied on the HiFi DNA assembly mix. Intramolecular reclosure used the KLD enzyme mix. In traditional cloning, inserts were treated with DpnI and backbones with DpnI and CIP. Ligations were performed with T4 DNA ligase. All enzymes used in cloning were obtained from NEB. Constructs were initially transformed into TOP10 E. coli (Invitrogen). DNA was introduced by electroporation using 0.1 cm gap cuvettes (USA Scientific) with a Bio-Rad MicroPulser. For vibrios, DNA was introduced by triparental mating, as described (Bassler et al., 1993). V. parahaemolyticus was cured of phage VP882 via introduction of a plasmid (pJES-174) containing a fragment harboring the native VP882 origin of replication and plating with selection for the plasmid. The strain was subsequently cured of pJES-174 by growth in the absence of antibiotic selection. For S. typhimurium, plasmids and phage were introduced using electroporation and triparental matings. The efficiency of the *V. cholerae*-specific kill switch was quantified by calculating the difference in CFUs obtained from the indicated *Vibrio* strains when mated with *E. coli* carrying a control plasmid (pJY-014) versus when mated with *E. coli* carrying the PvqmR-q kill switch plasmid (pJES-117).

TABLE 3

Oligonucleotides Used.

| Primer | Sequence (5' - 3') | 5'* | Purpose |
|---|---|---|---|
| JSO-0080 | GCATTTCCAGTGGAGGATAT [SEQ ID NO.: 22] | 5'P | Plasmid construction |
| JSO-0083 | GTTTTTGGATCCAATCAGCTTGAC GTTGTTGC [SEQ ID NO.: 23] | | Plasmid construction |
| JSO-0084 | GTCGACAATGAAGGGTCTTTTA [SEQ ID NO.: 24] | | Plasmid construction |
| JSO-0085 | GTTTTTTGGATCCGGTGATTGATT GAG [SEQ ID NO.: 25] | | Plasmid construction |
| JSO-0206 | TCTAGAAGAAGCTTGGGATC [SEQ ID NO.: 26] | | Plasmid construction |
| JSO-0250 | CTGTTGCATGGGCATAAAG [SEQ ID NO.: 27] | | Plasmid construction |
| JSO-0337 | TTCACACCTCCTGTACGC [SEQ ID NO.: 28] | | Plasmid construction |
| JSO-0367 | GTTTTTTGAGCTCTGTTTATGTAAG CAGACAGTTTTATTGTTCA [SEQ ID NO.: 29] | | Plasmid construction |
| JSO-0369 | TAATCAGAATTGGTTAATTGGTTG TAACACT [SEQ ID NO.: 30] | | Plasmid construction |
| JSO-0402 | GGATCCGGTGATTGATTGAGC [SEQ ID NO.: 31] | | Plasmid construction |
| JSO-0403 | GGAGAAACAGTAGAGAGTTGCGA TA [SEQ ID NO.: 32] | | Plasmid construction |
| JSO-0404 | ATGACTAAAAAAATTTCATTCATT ATTAACGGCC [SEQ ID NO.: 33] | | Plasmid construction |
| JSO-0406 | CCATTCCCAAACATTACCTACCAT TAA [SEQ ID NO.: 34] | | Plasmid construction |
| JSO-0429 | GGATCCGGTGATTGATTGAGC [SEQ ID NO.: 35] | | Plasmid construction |
| JSO-0703 | CACATTGGTCTCGAAGGATCC [SEQ ID NO.: 36] | | Plasmid construction |
| JSO-0897 | GAATACACTCCTTGTAAGTGATTG TTATAAGGAGC [SEQ ID NO.: 37] | 5'P | Plasmid construction |
| JSO-0898 | CCAAAAGCCCTGTTTCACACACA [SEQ ID NO.: 38] | 5'P | Plasmid construction |
| JSO-0899 | TGTTCGATAATTATTTGGTCTTCG GTCATTTTTCC [SEQ ID NO.: 39] | 5'P | Plasmid construction |
| JSO-0941 | AGAATCTTTATTTTCAGGGCATGT CAATAAGCGAAGGGGATGA [SEQ ID NO.: 40] | | Plasmid construction |
| JSO-0942 | TTCGGGCTTTGTTAGCAGCCGGAT CCTGGTTGCGCTAC [SEQ ID NO.: 41] | | Plasmid construction |
| JSO-0943 | TCCCCTTCGCTTATTGACATGCCCT GAAAATAAAGATTCTCGCC [SEQ ID NO.: 42] | | Plasmid construction |
| JSO-0944 | CTGCTCAAGTAGCGCAACCAGGAT CCGGCTGCTAACAAAG [SEQ ID NO.: 43] | | Plasmid construction |

TABLE 3-continued

| | Oligonucleotides Used. | | |
|---|---|---|---|
| JSO-0956 | CTCAATGCTCCAGGGCGTTT [SEQ ID NO.: 44] | 5'P | Plasmid construction |
| JSO-0957 | GCAGACACGTTGAAGAGTCCAG [SEQ ID NO.: 45] | 5'P | Plasmid construction |
| JSO-0959 | GCGCCTCCTACCTTTGATGTC [SEQ ID NO.: 46] | 5'P | Plasmid construction |
| JSO-0960 | GTTTTTTAATTAAGTCTGGCATCAATGCGGATAGTA [SEQ ID NO.: 47] | | Plasmid construction |
| JSO-0961 | ACCGATACTCCAATAAAAAACCCCG [SEQ ID NO.: 48] | 5'P | Plasmid construction |
| JSO-0962 | GTTTTTTAATTAAGGCAGCGTTCAATTAAACAAAAGACC [SEQ ID NO.: 49] | | Plasmid construction |
| JSO-0969 | TAACTAAGTAACTAGTACAGGAGGTGTGAAATGACT [SEQ ID NO.: 50] | | Plasmid construction |
| JSO-0978 | ATGAGAGTACGGGAATACAACGAGC [SEQ ID NO.: 51] | | Plasmid construction |
| JSO-0985 | TTAATTAACTCGAGCGGTACCCG [SEQ ID NO.: 52] | | Plasmid construction |
| JSO-0999 | GTTTTTTGGTACCTCTTACCAGCCTAACTTCGATCA [SEQ ID NO.: 53] | | Plasmid construction |
| JSO-1000 | AGCAATTTAACTGTGATAAACTACCGCA [SEQ ID NO.: 54] | | Plasmid construction |
| JSO-1001 | TCTTTTTGCATGCGGCGG [SEQ ID NO.: 55] | | Plasmid construction |
| JSO-1002 | AAGGATCAGATCACGCATCTTCC [SEQ ID NO.: 56] | 5'P | Plasmid construction |
| JSO-1014 | TTGCTCAATCAATCACCGGATCC [SEQ ID NO.: 57] | 5'P | Plasmid construction |
| JSO-1026 | GGATCCGGTGATTGATTGAGCA [SEQ ID NO.: 58] | | Plasmid construction |
| JSO-1058 | TGTCATCTGGCAAATGGTCACTGA [SEQ ID NO.: 59] | | Plasmid construction |
| JSO-1088 | CTGTTGCATGGGCATAAAGTTGC [SEQ ID NO.: 60] | | Plasmid construction |
| JSO-1096 | GCGCGTACAGGAGGTGTGAAATGAGAGTACGGGAATACAACGAG [SEQ ID NO.: 61] | | Plasmid construction |
| JSO-1106 | GCATAAAGCTTGCTCAATCAATCACC [SEQ ID NO.: 62] | 5'P | Plasmid construction |
| JSO-1114 | GTTTTTTAATTAACTTTTTCCAGGCTGGATTGTAGGG [SEQ ID NO.: 63] | | Plasmid construction |
| JSO-1115 | CTTTTTCCAGGCTGGATTGTAGGG [SEQ ID NO.: 64] | 5'P | Plasmid construction |
| JSO-1118 | GTTTTTTAATTAAAGCATCATCCCCTTCGCTTATTGACAT [SEQ ID NO.: 65] | | Plasmid construction |
| JSO-1119 | AGCATCATCCCCTTCGCTTATTGACAT [SEQ ID NO.: 66] | 5'P | Plasmid construction |
| JSO-1138 | GTTTTTTAATTAAGGTTGTTGTGTAGAGTTTAACTGGCC [SEQ ID NO.: 67] | | Plasmid construction |

TABLE 3-continued

| | Oligonucleotides Used. | |
|---|---|---|
| JSO-1159 | GAATCCCTGCTTCGTCCATTTGA [SEQ ID NO.: 68] | Plasmid construction |
| JSO-1160 | GTTTTTTAATTAACTACTCCGTCA AGCCGTCAATT [SEQ ID NO.: 69] | Plasmid construction |
| JSO-1185 | CGCGTTATCGCTCTGAAAGTACA [SEQ ID NO.: 70] | Plasmid construction |
| JSO-1186 | GTTTTTTAATTAACCAATTCCTGC AGGATTTTGCG [SEQ ID NO.: 71] | Plasmid construction |
| JSO-1189 | ATGAATTTTGGTAACGTCATAAGA CGACTTAGG [SEQ ID NO.: 72] | 5'P Plasmid construction |
| JSO-1195 | CATCTTATAATCCGTCGAAAAAAG TCTGG [SEQ ID NO.: 73] | Plasmid construction |
| JSO-1224 | GGCCAGTTAAACTCTACACAACAA [SEQ ID NO.: 74] | Plasmid construction |
| JSO-1225 | CGCAAAATCCTGCAGGAATTGG [SEQ ID NO.: 75] | Plasmid construction |
| JSO-1226 | ATGAAACATCATCACCATCACCAC [SEQ ID NO.: 76] | 5'P Plasmid construction |
| JSO-1227 | GTGGAGCTCCCATTTCACTTTTC [SEQ ID NO.: 77] | Plasmid construction |
| JSO-1228 | CGCTCTAGAACTAGTGGATCCC [SEQ ID NO.: 78] | Plasmid construction |
| JSO-1229 | AGGAGGTGTGAAGTGTGTGATTT [SEQ ID NO.: 79] | 5'P Plasmid construction |
| JSO-1230 | CTCAATCAATCACCGGATCCTG [SEQ ID NO.: 80] | Plasmid construction |
| JSO-1240 | GTCTCATGAGCGGATACATATTTG AATGT [SEQ ID NO.: 81] | 5'P Plasmid construction |
| JSO-1241 | GTTTTGGTACCTTTATAAAGGGGC TGCTGG [SEQ ID NO.: 82] | Plasmid construction |
| JSO-1242 | TCATCGAGTGCCTTTTGGCTG [SEQ ID NO.: 83] | Plasmid construction |
| JSO-1243 | TTCACACCTCCTGTGGAGCT [SEQ ID NO.: 84] | Plasmid construction |
| JSO-1246 | TTAATTAACCAATTCCTGCAGGAT TTTGCG [SEQ ID NO.: 85] | Plasmid construction |
| JSO-1247 | GGTATATCTCCTTCTTAAAGTTAA ACAAAATTATTTCTAGAGG [SEQ ID NO.: 86] | Plasmid construction |
| JSO-1248 | GTTTTTTGGATCCGGCTGCTAACA AAG [SEQ ID NO.: 87] | Plasmid construction |
| JSO-1249 | GTTTTTTGGATCCAAAAGGCACTC GATGACTA [SEQ ID NO.: 88] | Plasmid construction |
| JSO-1250 | GAAATGGGCAGCAGCCATC [SEQ ID NO.: 89] | 5'P Plasmid construction |
| JSO-1255 | CATGATGAATTCTCCTTAGTAAAG TTAAAATACC [SEQ ID NO.: 90] | Plasmid construction |
| JSO-1256 | GCAGAAATCGGTACTGGCTTT [SEQ ID NO.: 91] | Plasmid construction |

TABLE 3-continued

Oligonucleotides Used.

| | | |
|---|---|---|
| JSO-1271 | GCTCTGAAAGTACAGATCCTCAGTG [SEQ ID NO.: 92] | Plasmid construction |
| JSO-1272 | TGATAAAACGCAGCAGTTATAATTTGCGA [SEQ ID NO.: 93] | Plasmid construction |
| JSO-1273 | TTCACACCTCCTGCAGGTAC [SEQ ID NO.: 94] | Plasmid construction |
| JSO-1274 | ATGATGAATTTTGGTAACGTCATAAGACGACT [SEQ ID NO.: 95] | Plasmid construction |
| JSO-1279 | CCACGGAATAGGAGGTGTTTAG [SEQ ID NO.: 96] | Plasmid construction |
| JSO-1280 | GAGGGATATCCATTACGCCAG [SEQ ID NO.: 97] | Plasmid construction |

Tn5 construction**

| | | |
|---|---|---|
| JSO-0929 | ctgtctcttatacacatctATTCCCATGTCAGCCGTTAAGTG [SEQ ID NO.: 98] | 5'P oriR6ky-oriT-cmR |
| JSO-0930 | ctgtctcttatacacatctAGGGCACCAATAACTGCCTTAAA [SEQ ID NO.: 99] | 5'P oriR6ky-ori T-cmR |
| JSO-0931 | ctgtctcttatacacatctTCTAGAAGAAGCTTGGGATC [SEQ ID NO.: 100] | 5'P oriR6ky-oriT-cmR |
| JSO-0932 | ctgtctcttatacacatctCTGTTGCATGGGCATAAAG [SEQ ID NO.: 101] | 5'P oriR6ky-oriT-cmR |
| JSO-1029 | ctgtctcttatacacatctCAAATGGACGAAGCAGGGATTC [SEQ ID NO.: 102] | 5'P araC-pBAD-vqmAPhage-oriT-kanR |
| JSO-1031 | ctgtctcttatacacatctTCCCTGTTAAGTATCTTCCTGGC [SEQ ID NO.: 103] | 5'P araC-pBAD-vqmAPhage-oriT-kanR |

| EMSA | | | Pairs |
|---|---|---|---|
| JSO-1089 | GCATCATCCCCTTCGCTTATTGAC [SEQ ID NO.: 104] | 5'B EMSA: Pqtip | JSO-1089 x 0897 |
| JSO-0897 | GAATACACTCCTTGTAAGTGATTGTTATAAGGAGC [SEQ ID NO.: 105] | 5'P EMSA: Pqtip | JSO-1089 x 0897 |
| JSO-0525 | TCCGAGTATTGCGCGAGCTG [SEQ ID NO.: 106] | 5'B EMSA: PvqmR | JSO-525 x 526 |
| JSO-0526 | GTTTGTACTTTACCGAACGC [SEQ ID NO.: 107] | EMSA: PvqmR | JSO-525 x 526 |
| JSO-1093 | GATTTTCACCCTGGCCACCT [SEQ ID NO.: 108] | 5'B EMSA: Downstream of gp55 | JSO-1093 x 1095 |
| JSO-1095 | CCCGATCCCAAGCTTCTTCTAGA [SEQ ID NO.: 109] | EMSA: Downstream of gp55 | JSO-1093 x 1095 |
| JSO-1091 | CTGCCATCATCGAGCTACTGG [SEQ ID NO.: 110] | 5'B EMSA: Internal to gp55 | JSO-1091 x 1092 |
| JSO-1092 | GTTGATGATGAGCACTGGGAAGC [SEQ ID NO.: 111] | EMSA: Internal to gp55 | JSO-1091 x 1092 |
| J50-1090 | AGACAGGGCACACGATACCA [SEQ ID NO.: 112] | EMSA: Upstream to gp55, promoter | JSO-1089 x 1090 |

TABLE 3-continued

Oligonucleotides Used.

| qPCR | | | Pairs |
|---|---|---|---|
| JSO-0134 | GACCCATTTCTAAACGCGCT [SEQ ID NO.: 113] | qRT-PCR, hfq | JSO-134 x 135 |
| JSO-0135 | GCCGGCACAACTGTAGAAAT [SEQ ID NO.: 114] | qRT-PCR, hfq | JSO-134 x 135 |
| JSO-0702 | ACCATTTTCCACGGACAAGAC [SEQ ID NO.: 115] | qRT-PCR, vqmaPhage | JSO-702 x 703 |
| JSO-0703 | CACATTGGTCTCGAAGGATCC [SEQ ID NO.: 116] | qRT-PCR, vqmaPhage | JSO-702 x 703 |
| JSO-0908 | TGATTGTGCTGGTTGTCGGTG [SEQ ID NO.: 117] | qRT-PCR, gp69 | JSO-908 x 909 |
| JSO-0909 | CCATTTCGTGAGAGGTGATGTACT TCTC [SEQ ID NO.: 118] | qRT-PCR, gp69 | JSO-908 x 909 |
| JSO-0910 | GTCATTTTCAACGGTTGCTCAACT CAC [SEQ ID NO.: 119] | qRT-PCR, gp70 | JSO-910 x 911 |
| JSO-0911 | TAAGCGACTGGGCCAGAAC [SEQ ID NO.: 120] | qRT-PCR, gp70 | JSO-910 x 911 |
| JSO-0912 | TCGAGGAGCTGGCCTATAAAGAC [SEQ ID NO.: 121] | qRT-PCR, gp71 | JSO-912 x 913 |
| JSO-0913 | AAAGCGAACAGGCTCCATCC [SEQ ID NO.: 122] | qRT-PCR, gp71 | JSO-912 x 913 |
| JSO-1399 | GCTGAGACGAAAAACATATTCTCA ATAAACCC [SEQ ID NO.: 123] | qPCR, VP882 cmR Tn5 specific | JSO-1399 x 1400 |
| JSO-1400 | GGCAGTTTCTACACATATATTCGC AAGATG [SEQ ID NO.: 124] | qPCR, VP882 cmR Tn5 specific | JSO-1399 x 1400 |
| JSO-1401 | GATTACTGGCTTACTATGTTGGCA CTG [SEQ ID NO.: 125] | qPCR, non-phage plasmid specific | JSO-1401 x 1402 |
| JSO-1402 | GTCAGCAACACCTTCTTCACGA [SEQ ID NO.: 126] | qPCR, non-phage plasmid specific | JSO-1401 x 1402 |
| Misc | | | Pairs |
| JSO-0747 | TCTAAAGAGTCGATGTGTTCACTG C [SEQ ID NO.: 127] | vqmaPhage locus | JSO-747 x 748 |
| JSO-0748 | CCAAGAGGTAGAATTGGACAGAG ATC [SEQ ID NO.: 128] | vqmaPhage locus | JSO-747 x 748 |
| JSO-0781 | AATACCATAGAACAGTCGCTCCTC [SEQ ID NO.: 129] | V. parahaemolyticus vqmA | JSO-781 x 782 |
| JSO-0782 | TTGCTTTATCGATCAGCTCGTTCT [SEQ ID NO.: 130] | V. parahaemolyticus vqmA | JSO-781 x 782 |
| JSO-0136 | CGTGAGCGTATTCCAGTGTC [SEQ ID NO.: 131] | hfq | JSO-136 x 137 |
| JSO-0137 | AGAAATCGCGTGCTTGTACA [SEQ ID NO.: 132] | hfq | JSO-136 x 137 |
| JSO-0862 | ATATTGCGGCCGGTGACAAAAG [SEQ ID NO.: 133] | gp21-gp29 fragment | JSO-862 x 875 |
| JSO-0875 | CTGCCCATCTTGACCCCTT [SEQ ID NO.: 134] | gp21-gp29 fragment | JSO-862 x 875 |

TABLE 4 daDNA (gene blocks) Used.

| # | gBlockname | sequence (5'-3') |
|---|---|---|
| 1 | JSgBlock-30 | TAGCATTTTTATCCATAAGATTAGCGGATCCTACCTGACGC<br>TTTTTATCGCAACTCTCTACTGTTTCTCCGGTACCTGCAGGA<br>GGTGTGAAATGTCAATAAGCGAAGGGGATGATGCTTACAT<br>CCGCTCGTTGATTCATTTTTTTGGCAATCAACCGGATCCGT<br>GGGGCATCAAGGACACCAAGTCGGTGTTCATCTATGCAAA<br>CCAGCCCTTTCGAGAGTTAGTCGGTATGAAGAACCGCAAC<br>GTGGAAGGACTTACCGACGCTGATATGGATTGCGAAACTG<br>CGGCCTTTGCCGACTCCTTTCAGGCCCAAGATAGGCTGGTC<br>GAGCAAGGCCGGGAGAAGAAAATCGTCCTGGACGTACACC<br>CCTACGCGAATGGTTGGCGCGTTTTCACTTTCACCAAGACC<br>CCTCTCATCATGCCGTCCGGACGTGTGGCCGGCACCATTTT<br>CCACGGACAAGACCTGACTGACACGGCTGGCCGCATCGAG<br>CGTGCAGTGGTTGAGCTGCTGCTGCCTTCCAGTGGCCAGGC<br>TGGATCCTTCGAGACCAATGTGGTCGGTCTCAACTTGACCG<br>AACGCGAGGAACTGGTGCTGTTCTTCCTGCTTCGTGGCCGA<br>ACGGCCAAGGATATCGCTGGCATGCTGGGGCGCTCTCCCC<br>GCACCATCGAACACGCTATCGAGCGCATCCGCAACAAATT<br>CGGTGCTGGCAACAAGCGGGAGCTCATCGATATGGCCATG<br>TCCAAGGGTTATTACAGCATGGTGCCAAAAGCCCTGTTTCA<br>CACACAGGTCTCGATGCTGCTCAAGTAGCGCAACCAGGAT<br>CCGGTGATTGATTGAGCAAGCTTTATGCTTGTAAACCGTTT<br>TGTGA [SEQ ID NO.: 10] |
| 2 | JSgBlock-40 | TAGCATTTTTATCCATAAGATTAGCGGATCCTACCTGACGC<br>TTTTTATCGCAACTCTCTACTGTTTCTCCGGTACCTGCAGGA<br>GGTGTGAAATGGATTTGAGCACCCTTATCGCCCTGCTGACT<br>CTGATTGTGCTGGTTGTCGGTGGTTTGCTCTCCCTCCTTTGG<br>GGAAAGGTGAACAGCATCTCTCAGCAGCTGGCCGACGAGC<br>GTGTCCGGTCTGCCGAGAAGTACATCACCTCTCACGAAATG<br>GAACGGCGCCTCGAGCAAGCCATTGCACCGCTGGAGCGAA<br>CGCTCGAGCGGATGGAAAACCAGAACAACCAGATTTTCCA<br>GCTGTTGCGCCGCCACTACCACGCGGAGGCCAACTAATGG<br>ACAAGCAGCAAGCGAAATCAATCGCCATCAACGAAGTGAT<br>CGAACGTGAAGGCGGCTATGTGAATCACCCGGATGACCGA<br>GGCGGCCCTACTCGCTGGGGCGTTACCCAGGCGAAGGCTC<br>GGGAGCACGGTTATCACGGTGACATGCGCGACTATCCGGT<br>CGAGGCAGCTTTCGCTGTTTATGACGCGGATTATTGGCAGC<br>GCATGAAGCTGGACGAAATTGGCGACTACAGCCCAGACCT<br>GGCTGTGAAGCTGTTCGACTTCGGTGTGAACAGTGGAACG<br>GGCCGGGCGGCTCGTCATTTTCAACGGTTGCTCAACTCACT<br>GAACAACCGCGGCGAGTTTTATCCGGACATTAAGGTCGAC<br>GGCGCTATCGGTCAAAAGACCCTGGCTTCGCTGGCCGGCTT<br>CTACCGCAAGCGCGGTGAGGCAGGCTTGGCCGTTCTGGCC<br>CAGTCGCTTAACGGCCTGCGCATTGCTTTTTGCGTTGGCAT<br>CACTGAGGACAACGAGTCGCAGGAAGTATTCGCCTTTGGC<br>TGGTTGTCTCGCATCGTTCATTTGTAAGGAGCTGAAATGGA<br>ACCTTTGACCATTGCGCTCGGCCTGGCCAAGTTGACCGGGC<br>TGGATAAGAAAATCGGCCGCTGGATTGGTGGCGACAATGG<br>CGAGGAGGTTGCCGAGAAGGTTGTCTCCATCGCCCAGCAG<br>GTAACGGGCGCCAAGAATGGCGATCAGGCGCTGGCCAAGC<br>TGGAAGCCAACCCTGAGCAGTTGATTGAGTTCGAGCAGGC<br>AATGCACGAGCACGAACTGCACCTCGAGGAGCTGGCCTAT<br>AAAGACCGCGCTGATGCTCGAGCGATGCAAGTGGCGGCGC<br>TACAGGGTAACGATACCCTGTCTAAGCGTTTCGTCTATTAC<br>TTCGCTATCGGATGGAGCCTGTTCGCTTTCCTGTACCTGGG<br>CTTCATTACTTTCGGGGATATCCCGGAAGCAAACATCCGCT<br>TTGCTGACACTGTCCTGGGCTTCCTGCTCGGTACAGTACTC<br>GCTGGCATGTTCGGCTTCTTCTATGGCTCAAGCGCGGGAA<br>CGAACGTCGAGCAGAGCAGCAAGACTTGCACGCCGCGCTA<br>ACGCCGCGGCGCCGCTAGTTTTCTCCACTTCTAGGGATCCG<br>GTGATTGATTGAGCAAGCTTTATGCTTGTAAACCGTTTTGT<br>GA [SEQ ID NO.: 11] |
| 3 | JSgBlock-42 | TAGCATTTTTATCCATAAGATTAGCGGATCCTACCTGACGC<br>TTTTTATCGCAACTCTCTACTGTTTCTCCGGTACCTGCAGGA<br>GGTGTGAAATGAGAGTACGGGAATACAACGAGCAGCAACT<br>TGACTGGGTGCGCCTTCGAATCTTTCAGGCGCATTCGCTGC<br>ATATCAAGGGTAAGCCATTGTTTGAGGGCACGCAGTACTGT<br>GTTCCGGCCTCTCACATAAAACGCGCCAAGACGAAAGAAG<br>AACGAATCGAAAAGAGCTCCGCGGCGACCTGTTCCAGGT<br>GAAGGGCCGAGAGTCTCGCAGGGGGAAAAGTTCCATGCCA<br>TTGCCGCCTTGGGCATTCGAGGATAGCAGAGTCGTCCGCGT<br>GGTGAATGCCCTCCCTGATGGCCAGCGCCATTGGATCATGT<br>ACGCATACAGCGACTGCTACAACTGGGACAATGAGTCCGG<br>TGCGGTTGTCGCTCTCTGGAAAGAGTTCGAGCCAGAGCTGG<br>AAGGTGTTCGCGATGACACCCTGCAGAAGCTGAAAGGCAT |

TABLE 4-continued daDNA (gene blocks) Used.

| # | gBlockname | sequence (5'-3') |
|---|---|---|
| | | GGCTTACCTCTGTGTCCAGGACTTCAAGAACATCAAGAACC GAGGCAAGCCTGCACACTTGCCCTCACGCATTCGCCAGCTG ACTGGCGTGCCAGAGGGAAACTGGCGGCGTGACTGGTTGC CGCGCTGGAGACGAATGCAGCAAATCCTGACTGAGTTCGA CCGTGCGGCCCTGGCCAAGGTGATGGAGGTGATTTGTGAC CGACACGTTGCCTAAGGATCCGGTGATTGATTGAGCAAGCT TTATGCTTGTAAACCGTTTTGTGA [SEQ ID NO.: 12] |
| 4 | JSgBlock-44 | TAGCATTTTTATCCATAAGATTAGCGGATCCTACCTGACGC TTTTTATCGCAACTCTCTACTGTTTCTCCGGTACCTGCAGGA GGTGTGAAGTGCATATTCGCAGAAAAATTTTCAATTCTATT CTTACTATCCGCATTGATGCCAGACTTTTTTCGACGGATTAT AAGATGATGAATTTTGGTAACGTCATAAGACGACTTAGGA AGGCTAAAGGCTGGACTCTTCAACGTGTCTGCGAAGAGAT GAATGGTGCCATTCAGACCGGTCACTTATCTCGCATTGAGC GAGGTGAACTGACGCCATCCGTTTACATAGCACGCAACATT GCCCGATCGCTTGGTACCTCACTGGATACCATGCTTGCCGA GGCCGATGGGGGCCGCTCGCCCAAGTGGTACCGGATCCA GCGCAGCGGGTTCCGGTACTTTCATGGGTGCAAGCTGGCCT CTGGACTTCCTCGCCAACTGGCGTGGTGCCTGAGCTGTGCG ATAAATGGGTGGTTGCGCCAAGGGCCAAGTTACCGCCCCG GTGTTATGCACTGGAGGTAAGGGGCGACAGCATGCAAGCG CAGTATGGCATGAGCTTCCCGGAGGGGTGCTACATCATCGT GGATCCGAACCGCGTGCCTGAAAACAAGTCCTTTGTCGTGG CGATGCAAACGAACGCGGAAGAGGCCACATTCAAGCAGCT GATCATCGAGGGCGCGGACAAGTATTTGAAGCCGTTAAAC CCACAATATCCACTGCTTAAAATTGACCAAGAAGTAATCAC TTGTGGCGTTGTTATCGATATGGTGTGTCATCTGGCAAATG GTCACTGATAAAACGCAGCAGTTATAATTTGCGAAAAGTG AGAAAATTAGCTTAAACTAGGGCAGCCATAGAAGCCTATC GGCTGCATTTTTGTGCAAGGTTAGATATGGATCCGGTGATT GATTGAGCAAGCTTTATGCTTGTAAACCGTTTTGTGA [SEQ ID NO.: 13] |
| 5 | JSgBlock-47 | TAGCATTTTTATCCATAAGATTAGCGGATCCTACCTGACGC TTTTTATCGCAACTCTCTACTGTTTCTCCGGTACCTGCAGGA GGTGTGAAGTGTGTGATTTTTGCAGTGAACACATCGACTCT TTAGACGCCCTACAATCCAGCCTGGAAAAAGGTACTGCCA TCATCGAGCTACTGGACACCGCGCTTAGTGCCGGTATCGAG GTAAGCCCGAGGGTGGTATCGTGTGCCCTGTCTGCTGCCCA CCAGCACCTTCAGGTATCGGAAAAAATAAACCGCAGCCTG CAAATAGGCTGCGGTTCAAAGGAGGTGCTTCGCCTTGTTGA TTAGTCATCGAGTGCCTTTTGGCTGGCCTCCCATGCGGCTG TCATTGCCTCAACGCGGGTGCCCTTGATTTTCACCCTGGCC ACCTCCTCGCCTTCCACCAGCGCCCAGGCTTCCCAGTGCTC ATCATCAACCTGGTGAGCCACGAGTCTGGGCTTCTGCGCTT TCTTCGGCTGTTTTTCTTAGCGCAACCAGGATCCGGTGATT GATTGAGCAAGCTTTATGCTTGTAAACCGTTTTGTGA [SEQ ID NO.: 14] |
| 6 | JSgBlock-53 | GCCAACCACTGAGGATCTGTACTTTCAGAGCGATAACGCG ATAGAAATAGATATTGGCCCGGTATTAAAGCGCATCCGTTA TGAGCGAGGGCTAACGCTACAAAAGCTGTCACGGCTTACG GATGACAAAGTGCTACCAAGCAACATTTCCCGCATCGAGA GTGCGGGCGCTGGCGCTACGCTTAAAAACCTTGACCACCTTG GCGAATGCGCTGGGGACTTCTCCTTCTGACATTCTTCGTGA AGCTGAGGGCGGTGATAAGGTGATCACCAAGCCGCAGCAA GTCCTTTATGTACCTGTTTTGTCTTGGGTTCAGGCTGGCACC TGGACTGAATCACCAGAGCAGCCTGCCGATGGTGACTATG ATGAATGGGTAGAGGCACCAAGAGGCGCATCCAGGAAGGC TTTCGGCCTTCGAGTTCAAGGGGATAGTATGCAAGCCCCTA TCGGCAAGTCGTTCCCGGAAGGATGCTGCATAGTTGTTGAC CCAACCAAACAAGCAGATAACCGCTCGTTTGTTGTTGCTCG CCTGGCAGACACAGGAGAGCACACGTTCAAGCAGCTGATC ATTGACGGGCCGCACCAATATCTAAAGCCGCTAAACCCAA GTTACCGAACCATAGAAGTGAACAGCGAAGTACACGTCTG CGGGGTCGTTTTAGCATGGGGTGAAGGGTACACGGTGAAC GGTATTTAATTAATTAACCAATTCCTGCAGGATTTTGCGGC CGCTTGCT [SEQ ID NO.: 15] |
| 7 | JSgBlock-55 | GCCAACCACTGAGGATCTGTACTTTCAGAGCGATAACGCG ACTTTAGGGCAAGTAATCAGACGGATACGCCACGCCAAAC AATGGACGCTACAGCGGACTTGCGAAGAAGTGGACTTCCA AATTCAACCAGGACACCTCTCCCGTATTGAGCGGGGCGAG GGAATTCCATCCATACACTTTGTAAATATCATTTCCAAAGC GCTTGGCGTTTCTATAGACGCGATAATGGAAGAGGTTGAA |

TABLE 4-continued daDNA (gene blocks) Used.

| # | gBlockname | sequence (5'-3') |
|---|---|---|
| | | GGTAAAAGGCCTGTAAAAGTATCAACCACAGAACCCATCC CTTACCTACCAATAGTCTCATGGGTCCAAGCAGGATCCTGG ACCGACTCCCCACCGGCGGCAGACCCTCTCAGCTGTGATGA CTGGGTGATAGCCCCTAAGAAACTCCCAAAGAACTGCTAT GCATTGCGCGTAGTAGGCGACAGCATGACCGCACCATACG GCCCATCGTTCCCTGATGGCTGCATTATCATTGTTGACCCC ACCAAACAGCCTGAGAACAAGAGTTTTGTTGTTGCAAGGC AGGAAGGCTCAGACGAAGCAACCTTCAAACAACTAGCCAT TGAAGGCGGAACAAGATACTTAAAGCCACTGAATCAACAA TACCCACTGATTCAGATAAATGGCGACACTAGGTTCTGCGG AGTCGTGACCTTCATAATTTCACAAATCTAGTTAATTAACC AATTCCTGCAGGATTTTGCGGCCGCTTGCT [SEQ ID NO.: 16] |
| 8 | JSgBlock-56 | GCCAACCACTGAGGATCTGTACTTTCAGAGCGATAACGCG AGCACAAAAAGAAACCATTAACACAAGAGCAGCTTGAGG ACGCACGTCGCCTTAAAGCAATTTATGAAAAAAAGAAAAA TGAACTTGGCTTATCCCAGGAATCTGTCGCAGACAAGATGG GGATGGGGCAGTCAGGCGTTGGTGCTTTATTTAATGGCATC AATGCATTAAATGCTTATAACGCCGCATTGCTTGCAAAAT TCTCAAAGTTAGCGTTGAAGAATTTAGCCCTTCAATCGCCA GAGAAATCTACGAGATGTATGAAGCGGTTAGTATGCAGCC GTCACTTAGAAGTGAGTATGAGTACCCTGTTTTTTCTCATG TTCAGGCAGGGATGTTCTCACCTGAGCTTAGAACCTTTACC AAAGGTGATGCGGAGAGATGGGTAAGCACAACCAAAAAA GCCAGTGATTCTGCATTCTGGCTTGAGGTTGAAGGTAATTC CATGACCGCACCAACAGGCTCCAAGCCAAGCTTTCCTGAC GGAATGTTAATTCTCGTTGACCCTGAGCAGGCTGTTGAGCC AGGTGATTTCTGCATAGCCAGACTTGGGGGTGATGAGTTTA CCTTCAAGAAACTGATCAGGGATAGCGGTCAGGTGTTTTTA CAACCACTAAACCCACAGTACCCAATGATCCCATGCAATG AGAGTTGTTCCGTTGTGGGGAAAGTTATCGCTAGTCAGTGG CCTGAAGAGACGTTTGGCTGATTAATTAACCAATTCCTGCA GGATTTTGCGGCCGCTTGCT [SEQ ID NO.: 17] |
| 9 | JSgBlock-58 | CCTATCAGTGATAGAGAAAAGTGAAATGGGAGCTCCACAG GAGGTGTGAAATGGATTTAAGGGTTTCAAACGCTAAGGAT TTATTGGATAAGTTCGAGGAGAAAGCTGTACAGATGGAAT CAATCAGCCAGTTACTGGCTAATGCGCCGGAGGATCTGAC GCTGGCCACCGTGCAAGGTAGTCTATCGGCATTGGCATCGA TCGCCAGGGATGCCGGGGAGGCTGCTGATCGCCTGAGGAC GATCAGCAGTGCGGAAGGTTAGTCGCGGTTGCGGAAGATG TTCCAGGCCGCGGCGATCGCTGCAGCCCTGGAGCTCATCGA GTGCCTTTTGGCTGGCCTCCCATGCGGCTGTCATTGCCTCA AC [SEQ ID NO.: 18] |
| 10 | JSgBlock-60 | CCTATCAGTGATAGAGAAAAGTGAAATGGGAGCTCCACAG GAGGTGTGAAATGGACAAAGATTGCGAAATGAAACGTACC ACCCTGGATAGCCCCGCTGGGCAAACTGGAACTGAGCGGCT GCGAACAGGGCCTGCATGAAATTAAACTGCTGGGTAAAGG CACCAGCGCGGCCGATGCGGTTGAAGTTCCGGCCCCGGCC GCCGTGCTGGGTGGTCCGGAACCGCTGATGCAGGCGACCG CGTGGCTGAACGCGTATTTTCATCAGCCGGAAGCGATTGAA GAATTTCCGGTTCCGGCGCTGCATCATCCGGTGTTTCAGCA GGAGAGCTTTACCCGTCAGGTGCTGTGGAAACTGCTGAAA GTGGTTAAATTTGGCGAAGTGATTAGCTATCAGCAGCTGGC GGCCCTGGCGGGTAATCCGGCGGCCACCGCCGCCGTTAAA ACCGCGCTGAGCGGTAACCCGGTGCCGATTCTGATTCCGTG CCATCGTGTGGTTAGCTCTAGCGGTGCGGTTGGCGGTTATG AAGGTGGTCTGGCGGTGAAAGAGTGGCTGCTGGCCCATGA AGGTCATCGTCTGGGTAAACCGGGTCTGGGACCTGCAGGC GGATCCGGCGAGCCAACCACTGAGGATCTGTACTTTCAGA GCGATAACGCGTGTGATTTTTGCAGTGAACACATCGACTCT TTAGACGCCCTACAATCCAGCCTGGAAAAAGGTACTGCCA TCATCGAGCTACTGGACACCGCGCTTAGTGCCGGTATCGAG GTAAGCCCGAGGGTGGTATCGTGTGCCCTGTCTGCTGCCCA CCAGCACCCTTCAGGTATCGGAAAAAATAAACCGCAGCCTG CAAATAGGCTGCGGTTCAAAGGAGGTGCTTCGCCTTGTTGA TTAGTCATCGAGTGCCTTTTGGCTGGCCTCCCATGCGGCTG TCATTGCCTCAAC [SEQ ID NO.: 19] |
| 11 | JSgBlock-69 | GGGTCTTTTTGCATGCGGCGGGTACCGCTCGAGTTAATTAA TATTTTAAATCAGCAAACACTATGCAAGTTGGCCAATTTAA TTAGCGGGCGGCATCAGTTTCATAATGATTGCATCAGGATT TTGCCACCCGCTCCCGGTATTGTTTACATATTAAAATGATTT TTAACTGGTGCTGACAACTATGCTAAATACGCAGGAAGTA |

TABLE 4-continued daDNA (gene blocks) Used.

| # | gBlockname | sequence (5'-3') |
|---|---|---|
|  |  | CTTAAAGAAGGAGAGAAGCGGAAAATCCGCAGCCCGGAA<br>GCATGGTTTATACAGACGTGTTCCGCGCAAAAGCTGCATAT<br>GAGAGTACGGGAATACAACGAGCAGCAACTTGACTGGG<br>[SEQ ID NO.: 20] |
| 12 | JSgBlock-<br>73 | CCTATCAGTGATAGAGAAAAGTGAAATGGGAGCTCCACAG<br>GAGGTGTGAAATGGAAAATGTAACCTTTGTAAGTAATAGT<br>CATCAGCGTCCTGCCGCAGATAACTTACAGAAATTAAAATC<br>ACTTTTGACAAATACCCGGCAGCAAATTAAAAGTCAGACT<br>CAGCAGGTTACCATCAAAAATCTTTATGTAAGCAGTTTCAC<br>TTTAGTTTGCTTTCGGAGCGGTAAACTGACGATTAGCAATA<br>ATCACGATACGATTTACTGTGACGAACCTGGGATGTTGGTG<br>CTCAAAAAAGAGCAGGTAGTTAACGTGACGCTTGAAGAGG<br>TCAATGGCCACATGGATTTCGATATACTCGAGATACCGACG<br>CAACGACTTGGCGCTCTCTATGCACTTATCCCAAACGAGCA<br>GCAAACCAAATGGCGGTACCCACAGAGAAAGCGCAGAA<br>GATCTTCTATACGCCTGACTTTCCTGCCAGAAGAGAGGTAT<br>TTGAACATCTGAAAACGGCGTTCTCCTGTACGAAGGATACA<br>AGCAAAGGTTGCAGTAACTGTAACAACAAAAGTTGTATTG<br>AAAATGAAGAGTTAATTCCTTATTTTCTGCTGTTCCTGCTTA<br>CTGCTTTTCTCCGACTCCCGGAGAGTTATGAGATCATCCTT<br>AGCTCGGCTCAGATAACGTTAAAGGAGCGCGTTTACAACA<br>TTATATCTTCGTCACCCAGTAGACAGTGGAAGCTTACGGAT<br>GTTGCCGATCATATATTTATGAGTACGTCAACGCTCAAACG<br>GAAACTTGCAGAAGAAGGTACCAGCTTTAGCGACATCTAC<br>TTATCGGCAAGAATGAATCAGGCAGCAAAACTTTTACGCA<br>TAGGCAACCATAATGTTAATGCTGTAGCATTAAAATGTGGT<br>TATGATAGCACGTCCTACTTCATTCAATGTTTCAAAAAATA<br>TTTTAAAACTACGCCATCGACATTCATAAAAATGGCGAACC<br>ATTAATCATCGAGTGCCTTTTGGCTGGCCTCCCATGCGGCT<br>GTCATTGCCTCAAC [SEQ ID NO.: 21] |

TABLE 5

Summary of Cloning Techniques.

| # | Plasmid name | Plasmid ID | Strain ID | Relevant fragment | Marker, Origin |
|---|---|---|---|---|---|
| 1 | control::Tn5 VP882 | JSP-002 | JSP-0002 | full length phage | Cm, VP882 and oriR6ky |
| 2 | q::7n5 VP882 | JSP-003 | JSP-0003 | full length phage | Cm, VP882 and oriR6ky |
| 3 | vqmA$_{Phage}$::Tn5 VP882 | JSP-024 | JSP-0024 | full length phage | Cm, VP882 and oriR6ky |
| 4 | gp07::Tn5 (araC-pBAD-vqmA$_{Phage}$-oriT-kanR) VP882 | JSP-1270 | JSP-1270 | full length phage | Kan, VP882 |
| 5 | PvqmA$_{Vc}$-vqmA$_{Vc}$ | pJES-023 | JSS-0319 | vqmA$_{Vc}$ | Kan, p15A |
| 6 | PvqmR-lux, ZeoR | pJES-045 | JSS-0787-790 | PvqmR-lux reporter, ZeoR | Zeo, p15A |
| 7 | pBAD-vqmA$_{Phage}$ | pJES-052 | JSS-0864 | vqmA$_{Phage}$ | Kan, p15A |
| 8 | pBAD-gp69-71 | pJES-087 | JSS-1171 | gp69-71 | Kan, p15A |
| 9 | pBAD-q | pJES-093 | JSS-1197 | q | Kan, p15A |
| 10 | pET15b-T7-HIS-vqmA$_{Phage}$ | pJES-095 | JSS-1204 | HIS-vqmA$_{Phage}$ | Amp, pBR322 |
| 11 | Pq-lux, KanR | pJES-097 | JSS-1219 | Pq-lux reporter, KanR | Kan, p15A |
| 12 | PvqmR-lux, AmpR | pJES-101 | JSS-1245 | PvqmR-lux reporter, AmpR | Amp, pBR322 |
| 13 | Pq-lux, AmpR | pJES-104 | JSS-1271 | Pq-lux reporter, AmpR | Amp, pBR322 |
| 14 | Pgp69-lux | pJES-105 | JSS-1291 | Pgp69-lux reporter | Amp, pBR322 |
| 15 | PvqmR-q | pJES-117 | JSS-1345 | PvqmR-q kill switch | Kan, p15A |
| 16 | Pqtip-lux | pJES-119 | JSS-1357-1358 | Pqtip-lux reporter | Amp, pBR322 |
| 17 | PvqmA$_{Phage}$-lux | pJES-120 | JSS-1365 | PvqmA$_{Phage}$-lux reporter | Amp, pBR322 |
| 18 | cI$_{VP882}$, Pq-lux | pJES-125 | JSS-1388 | cI$_{VP882}$, Pq-lux reporter | Amp, pBR322 |

TABLE 5-continued

Summary of Cloning Techniques.

| # | Plasmid name | Plasmid ID | Strain ID | Relevant fragment | Marker, Origin |
|---|---|---|---|---|---|
| 19 | minimal phage "Active Fragment", CmR | pJES-128 | JSS-1384 | "Active Fragment", CmR | Cm, oriR6ky |
| 20 | pBAD-vqmA$_{Phage}$, cI$_{VP882}$, Pq-lux | pJES-130 | JSS-1434 | pBAD-vqmA$_{Phage}$, cI$_{VP882}$, Pq-lux reporter | Kan, p15A |
| 21 | minimal phage "Active Fragment", AmpR | pJES-133 | JSS-1462 | "Active Fragment", AmpR | Amp, pBR322 |
| 22 | pH6HTN-pT7-HIS-HALO-cI$_{VP882}$ | pJES-134 | JSS-1460 | HIS-HALO-cI$_{VP882}$ | Amp, pBR322 |
| 23 | HALO-cI$_{VP882}$, Pq-lux | pJES-140 | JSS-1480 | HALO-cI$_{VP882}$, Pq-lux reporter | Amp, pBR322 |
| 24 | pTetA-qtip, AmpR | pJES-141 | JSS-1487 | qtip, AmpR | Amp, pBR322 |
| 25 | pTetA-qtip, KanR | pJES-143 | JSS-1507 | qtip, KanR | Kan, p15A |
| 26 | pET15b-pT7-HIS-qtip | pJES-147 | JSS-1542 | HIS-qtip | Amp, pBR322 |
| 27 | pH6HTN-pT7-HIS-HALO-cI$_{VP58.5}$ | pJES-148 | JSS-1543 | HIS-HALO-cI$_{VP58.5}$ | Amp, pBR322 |
| 28 | pH6HTN-pT7-HIS-HALO-cI$_{MJ1}$ | pJES-150 | JSS-1545 | HIS-HALO-cI$_{MJ1}$ | Amp, pBR322 |
| 29 | pH6HTN-pT7-HIS-HALO-cI$_{lambda}$ | pJES-151 | JSS-1546 | HIS-HALO-cI$_{lambda}$ | Amp, pBR322 |
| 30 | pTetA-orf$_{584}$ | pJES-153 | JSS-1568 | MJ1 orf$_{584}$ | Kan, p15A |
| 31 | pH6HTN-pT7-HALO-cI$_{VP882}$ | pJES-154 | JSS-1575 | HALO-cI$_{VP882}$ (no HIS) | Amp, pBR322 |
| 32 | pH6HTN-pT7-HIS-HALO | pJES-156 | JSS-1584 | HIS-HALO | Amp, pBR322 |
| 33 | pH6HTN-pT7-HALO | pJES-157 | JSS-1590 | HALO (no HIS) | Amp, pBR322 |
| 34 | HALO; Pq-lux | pJES-158 | JSS-1602 | HALO (no cI$_{VP882}$), Pq-lux reporter | Amp, pBR322 |
| 35 | pBAD-cI | pJES-159 | JSS-1606 | cI$_{VP882}$ | Amp, pBR322 |
| 36 | pTetA-SNAP-qtip | pJES-166 | JSS-1619 | SNAP-qtip | Kan, p15A |
| 37 | PInvF-q | pJES-167 | JSS-1620 | PinvF-q kill switch | Kan, p15A |
| 38 | pTetA-hilD | pJES-171 | JSS-1624 | hilD | Amp, pBR322 |
| 39 | cI$_{MJ1}$, repA$_{MJ1}$, pRE112 | pJES-173 | JSS-1649-51 | cI$_{MJ1}$, repA$_{MJ1}$ | Cm, MJ1 and oriR6ky |
| 40 | cI$_{VP882}$, repA$_{VP882}$, vqmA$_{Phage}$, pRE112 | pJES-174 | JSS-1180 | cI$_{VP882}$, repA$_{VP882}$, vqmA$_{Phage}$ | Cm, VP882 and oriR6ky |
| 41 | ΔcI$_{VP882}$, repA$_{VP882}$, ΔvqmA$_{Phage}$, pRE112 | pJES-175 | JSS-1703 | repA$_{VP882}$ | Cm, VP882 and oriR6ky |
| 42 | ΔcI$_{VP882}$, repA$_{VP882}$, vqmA$_{Phage}$, pRE112 | pJES-176 | JSS-1704 | repA$_{VP882}$, vqmA$_{Phage}$ | Cm, VP882 and oriR6ky |
| 43 | cI$_{VP882}$, repA$_{VP882}$, ΔvqmA$_{Phage}$, pRE112 | pJES-177 | JSS-1705 | cI$_{VP882}$, repA$_{VP882}$ | Cm, VP882 and oriR6ky |
| 44 | pBAD | pJY-014 | BB-Ec0366 | Empty vector | Kan, p15A |
| 45 | pBAD-vqmA$_{Vc}$, AmpR | pKP-367 | KPS-0383 | vqmA$_{Vc}$ | Amp, pBR322 |
| 46 | pBAD-vqmA$_{Vc}$, KanR | pKP-375 | KPS-0441 | vqmA$_{Vc}$ | Kan, p15A |
| 47 | pET15b-pT7-HIS-vqmA$_{Vc}$ | pKP-445 | KPS-0929 | HIS-vqmA$_{Vc}$ | Amp, pBR322 |
| 48 | pET28b-pT7-HIS-luxO | pWN-001 | BB-Ec0194 | HIS-luxO | Kan, pBR322 |
| 49 | pTetA | pXB-300 | NM-0196/ JSS-1478 | Empty vector | Amp, pBR322 |

TABLE 6

Cloning Techniques (Continued).

| # | Primers for insert | Template for insert | Primers for backbone | Template for backbone | Cloning method |
|---|---|---|---|---|---|
| 1 | | | | | in vitro transposon mutagenesis |
| 2 | | | | | in vitro transposon mutagenesis |
| 3 | | | | | in vitro transposon mutagenesis |
| 4 | | | | | in vitro transposon mutagenesis |
| 5 | JSO-080 × 083 (BamHI) | *V. cholerae* | JSO-084 × 085 (BamHI) | pEVS-143* | Traditional (one-sided BamHI) |
| 6 | JSO-355 × 356 | pCR topo vector (Thermo) | JSO-367 × 369 | JSS-743 (PvqmR-lux KanR, unpublished) | Traditional (blunt) |
| 7 | n/a | gblock30 | JSO-402 × 403 | pKP-389 (pBAD-vqmA$_{Vc}$-3XFLAG KanR, unpublished) | Gibson |
| 8 | n/a | gblock40 | JSO-402 × 403 | pKP-389 (pBAD-vqmA$_{Vc}$-3XFLAG KanR, unpublished) | Gibson |
| 9 | n/a | gblock42 | JSO-402 × 403 | pKP-389 (pBAD-vqmA$_{Vc}$-3XFLAG KanR, unpublished) | Gibson |
| 10 | JSO-941 × 942 | pJES-052 | JSO-943 × 944 | JSS-1023 (pT7-HIS-TEV-vqmA$_{Vc}$ AmpR, unpublished) | Gibson |
| 11 | JSO-959 × 960 (PacI) | VP882 | JSO-404 × 406 (PacI) | JSS-743 (PvqmR-lux KanR, unpublished) | Traditional (one-sided PacI) |
| 12 | JSO-1001 × 1002 (KpnI) | JSS-743 (PvqmR-lux KanR, unpublished plasmid) | JSO-999 × 1000 (KpnI) | pKP-445 | Traditional (one-sided KpnI) |
| 13 | JSO-959 × 960 (PacI) | VP882 | JSO-404 × 406 (PacI) | pJES-101 | Traditional (one-sided PacI) |
| 14 | JSO-961 × 962 (PacI) | VP882 | JSO-404 × 406 (PacI) | pJES-101 | Traditional (one-sided PacI) |
| 15 | JSO-1096 × 1014 | pJES-093 | JSO-337 × 429 | JSS-743 (PvqmR-lux KanR, unpublished plasmid) | Gibson |
| 16 | JSO-1118 × 1115 (PacI) | VP882 | JSO-969 × 406 (PacI) | pJES-101 | Traditional (one-sided PacI) |
| 17 | JSO-1114 × 1119 (PacI) | VP882 | JSO-969 × 406 (PacI) | pJES-101 | Traditional (one-sided PacI) |
| 18 | JSO-1138 × 956 (PacI) | VP882 | JSO-404 × 406 (PacI) | pJES-101 | Traditional (one-sided PacI) |

TABLE 6-continued

Cloning Techniques (Continued).

| # | Primers for insert | Template for insert | Primers for backbone | Template for backbone | Cloning method |
|---|---|---|---|---|---|
| 19 | JSO-1088 × 703 | JSS-1300 (phage miniplasmid, unpublished) | n/a | n/a | Intramolecular (reclosure) |
| 20 | first round: JSO-1138 × 956 (PacI); second round: JSO-1138 × 1106 (PacI) | first round: VP882; second round: pJES-125 | first round: JSO-404 × 406 (PacI); second round: JSO-1159 × 1160 (PacI) | first round: pJES-101; second round: pJES-052 | Multi-step: one-sided PacI, one-sided PacI |
| 21 | random fragments of phage DNA | VP882 | obtained commercially, ready-to-use linear | pSMART-LC-Amp (Lucigen) | Traditional (blunt) |
| 22 | JSO-1189 × 1138 (PacI) | VP882 | JSO-1185 × 1186 (PacI) | pJES-156 | Traditional (one-sided PacI) |
| 23 | JSO-1225 × 1226 (PacI) | pJES-134 | JSO-1224 × 1195 (PacI) | pJES-125 | Traditional (one-sided PacI) |
| 24 | JSO-1229 × 1230 (BamHI) | gblock47 | JSO-1227 × 1228 (BamHI) | pXB-300** | Traditional (one-sided BamHI) |
| 25 | JSO-1240 × 1241 (KpnI) | JSS-1487 | JSO-985 × 1026 (KpnI) | JSS-743 (PvqmR-lux KanR, unpublished plasmid) | Traditional (one-sided KpnI) |
| 26 | JSO-1249 × 1250 (BamHI) | JSS-1513 (pTetA-m-qtip KanR, unpublished) | JSO-1247 × 1248 (BamHI) | pKP-445 | Traditional (one-sided BamHI) |
| 27 | n/a | gblock53 | JSO-1246 × 1185 | pJES-156 | Gibson |
| 28 | n/a | gblock55 | JSO-1246 × 1185 | pJES-156 | Gibson |
| 29 | n/a | gblock56 | JSO-1246 × 1185 | pJES-156 | Gibson |
| 30 | n/a | gblock58 | JSO-1242 × 1243 | pJES-143 | Gibson |
| 31 | JSO-1255 × 1256 | pJES-134 | n/a | n/a | Intramolecular (reclosure) |
| 32 | | | | | |
| 33 | JSO-1255 × 1256 | pJES-156 | n/a | n/a | Intramolecular (reclosure) |
| 34 | JSO-1271 × 1272 | pJES-140 | n/a | n/a | Intramolecular (reclosure) |
| 35 | first round: n/a; second round: JSO-1273 × 1274 | first round: gblock44; second round: n/a | first round: JSO-402 × 403; second round: n/a | pKP-389 (pBAD-vqmA$_{Vc}$-3XFLAG KanR, unpublished); second round: n/a | Multi-step: Gibson, intramolecular (reclosure) |
| 36 | n/a | gblock60 | JSO-1242 × 1243 | pJES-143 | Gibson |
| 37 | n/a | gblock69 | JSO-985 × 978 | pJES-117 | Gibson |
| 38 | n/a | gblock73 | JSO-1242 × 1243 | pJES-141 | Gibson |
| 39 | JSO-1279 × 1280 | MJ1 | JSO-206 × 250 | pRE112*** | Traditional (blunt) |
| 40 | JSO-897 × 899 | VP882 | JSO-206 × 250 | pRE112*** | Traditional (blunt) |
| 41 | JSO-898 × 206 | pJES-176 | n/a | n/a | Intramolecular (reclosure) |
| 42 | JSO-957 × 1058 | pJES-174 | n/a | n/a | Intramolecular (reclosure) |
| 43 | JSO-898 × 206 | pJES-174 | n/a | n/a | Intramolecular (reclosure) |
| 44 | | | | | |
| 45 | | | | | |
| 46 | | | | | |

TABLE 6-continued

Cloning Techniques (Continued).

| # | Primers for insert | Template for insert | Primers for backbone | Template for backbone | Cloning method |
|---|---|---|---|---|---|
| 47 | | | | | |
| 48 | | | | | |
| 49 | | | | | |

Growth, Lysis, and Reporter Assays. Typically, overnight cultures were back diluted 1:1000 into fresh medium with appropriate antibiotics and strains were grown to $OD_{600}$ 0.5-0.6. Cultures were back diluted 1:20, and grown to $OD_{600}$ 0.1, before being dispensed (200 µL) into 96 well plates (Corning Costar 3904). MMC, ara, or aTc was added as specified. Wells that did not receive treatment received an equivalent volume of water. Plates were shaken at 37° C. and a BioTek Synergy Neo2 Multi-Mode reader was used to measure $OD_{600}$, $OD_{600}$ and bioluminescence, or $OD_{600}$ and fluorescence. Measurement times for single time point assays are provided in Table S4. In Figure S2D, *V. parahaemolyticus* was monitored at 6 h, *V. cholerae* at 8 h, and *E. coli* at 12 h. Relative light units (RLU) and relative fluorescence units (RFU) were calculated by dividing the bioluminescence and fluorescence readings, respectively, by the $OD_{600}$ at that time. In the case of fluorescence assays, M9 supplemented with 0.4% casamino acids (BD-Difco) was used and readings were made by excitation at 588 nm and emission at 633 nm. The glycerol stocks were prepared from three independent colonies of each strain at a single $OD_{600}$. Care was taken to ensure that the $OD_{600}$ between these strains was identical prior to storage. Parallel cultures of the same strains were used for viral preparations.

Phage DNA Isolation. Phage DNA was purified from phage particles present in the supernatants of lysed cells (virion) and from host cell pellets lysogenized with VP882 (prophage). Prophage DNA was purified using the Fosmid-MAX kit (Lucigen) according to the manufacturer's protocol for 1.5 mL cultures. Virion DNA was isolated using a Phage DNA isolation kit (Norgen Biotek) including the DNase I and Proteinase K treatment steps indicated in the manufacturer's protocol.

In vitro Tn5 (IVT) Mutagenesis. VP882 phage DNA was used as the target for IVT. VP882 prophage DNA was isolated as described above, with the addition of a final digestion step to remove residual genomic DNA. Removal was accomplished by treatment with EcoRI, a restriction site that is absent in the VP882 genome, followed by Plasmid-Safe DNase (Lucigen). The transposon was constructed by PCR amplification of pRE112 (Edwards et al., 1998) with primers JSO-929×930 and JSO-931×932 (see Table 2) to make recombinant VP882 phage carrying an oriR6ky-oriT-cmR Tn5 transposon. To engineer the recombinant VP882 phage carrying the araC-pBAD-vqmA$_{Phage}$-oriT-kanR Tn5 transposon, PCR amplification of pJES-052 with JSO-1029× 1031 was used (see Table 3). All IVT reactions were carried out in a PCR thermocycler with EZ-Tn5 transposase (Lucigen) as described by the manufacturer for in vitro insertion reactions.

RT-qPCR. Overnight cultures of *V. parahaemolyticus* carrying pJES-052 and either WT phage VP882 or phage VP882 q::Tn5 were back diluted 1:1000 and grown with shaking at 37° C. Upon reaching $OD_{600}$ 0.2-0.4, cultures were divided in half, ara (0.2% final) was added to one aliquot and an equal volume of water to the other. These preparations were allowed to continue to grow at 37° C. for 60 min. A total of 1.5-2 $OD_{600}$ worth of cells was treated with RNAProtect Bacteria Reagent (Qiagen) according to the supplier's protocol. The cells were pelleted at 4,000 RPM for 10 min at 4° C. Pellets were stored at −80° C. prior to processing. Total RNA was isolated from three independent cultures per condition using the RNeasy Mini Kit (Qiagen). The samples were treated with DNAse using a TURBO DNA-free Kit (Thermo). cDNA was prepared from 1.5 µg RNA as described (Tu and Bassler, 2007) using SuperscriptIII reverse transcriptase (Thermo). SYBR Green mix (Quanta) and Applied Biosystems QuantStudio 6 Flex Real-Time PCR detection system (Thermo) were used for real-time PCR. Each cDNA sample was amplified in technical quadruplicate. Data were analyzed by a comparative CT method, in which the indicated target gene (vqmA$_{Phage}$ or gp69-71) was normalized to an internal bacterial control gene (hfq). The reference sample for all comparisons was the WT *V. parahaemolyticus* strain lysogenized with phage VP882 q::Tn5 to which no arabinose was added.

qPCR and Viral Preparations. Viral preparations consisted of purified non-chromosomal DNA (ZR BAC kit, Zymo Research) prepared from 2 mL of cells. Following addition of the indicated compounds or water control, the cultures were returned to growth for 3 h prior to harvesting. This alteration in procedure was necessary to enable growth of sufficient cells for use with the viral preparation kit. 0.5 ng of purified non-chromosomal DNA was used for each qPCR reaction. qPCR reactions were performed as described above for qRT-PCR reactions. Data were analyzed by a comparative CT method in which the VP882 phage-specific primer set (JSO-1399×1400) was normalized to the non-phage plasmid-specific primer set (JSO-1401×1402). The reference sample for each comparison was the isogenic strain (Δtdh or WT) that was not induced.

Western Blot to Assess HALO-cI. The pJES-134 plasmid carrying the HIS-HALO-cI protein construct was transformed into recA$^+$ *E. coli* T7Express (NEB) and ΔrecA *E. coli* BLR(DE3) (Novagen). Overnight cultures were back-diluted 1:100 into fresh medium and grown to $OD_{600}$~0.4-0.6. The cultures were divided in half. To one aliquot, MMC (250 ng mL$^{-1}$ final conc.) was added, and to the other aliquot, an equivalent volume of water was added. Samples were incubated for an additional 2.5 h. 1 mL of culture was collected from each sample, the cells were pelleted (13,000 g×1 min), and resuspended in HALO western lysis buffer (30 µL B-PER complete (Thermo), 1× Halt protease inhibitor cocktail (Thermo), 0.5 mM EDTA, 5 µM HALO-TMR ligand (Promega), 1 µL benzonase (Millipore)). The samples were incubated in the dark at 37° C. for 15-20 min before addition of 10 µL Laemmli sample buffer (Bio-Rad), followed by incubation at 70° C. for 15-20 min. 10 µL of each sample was separated by SDS-PAGE in 4-20% Mini-Protein TGX gels (Bio-Rad) and imaged using an ImageQuant LAS 4000 (GE) imager under the SYBR-Green setting.

Co-Immunoprecipitation. Cultures of *E. coli* BL21(DE3) producing HIS-Qtip, HALO-cI, and HALO were grown overnight, back-diluted 1:100, and grown to $OD_{600}$~0.5-0.8. 0.5 mM IPTG was added, followed by 4 h continued incubation. The cultures were moved to ice and 75 mL of cells containing HIS-Qtip were divided into three equal aliquots of 25 mL and placed in 50 mL conical tubes. To one tube, 25 mL of cells that had produced HIS-Qtip were added. To a second tube, 25 mL of cells that had produced HALO-cI were added. To the third tube, 25 mL of cells that had produced HALO were added. Each mixture was made in triplicate and immediately pelleted at 4,000 RPM for 10 min at 4° C. The cell pellets were stored at −80° C.

Cell lysis was carried out by resuspending each pellet in 1 mL of lysis buffer (20 mM Tris-HCl pH 8, 150 mM NaCl, 1x protease inhibitor cocktail, and benzonase) followed by sonication (Branson). 50 µL of magnetic cobalt based beads (Thermo, Dynabeads His-Tag Isolation and Pulldown) were added to each lysate and the samples incubated at RT for 10-20 min with gentle agitation. The samples were placed in a magnetic stand separator (Thermo) for 2 min. Proteins that remained associated with the magnetic particles were retained on the tube-wall facing the magnet while unbound and non-specifically bound proteins were removed via three washes with wash buffer (lysis buffer lacking protease inhibitor and benzonase). The washed magnetic beads were resuspended in 100 µL of wash buffer. 30 µL aliquots were taken as specified (input, first wash, cobalt beads). HALO-TMR ligand (5 µM) was added to each aliquot and the samples incubated for 10-20 min at RT, protected from light. 10 µL of 4× Laemmli buffer was added to each sample followed by incubation in a PCR machine at 70° C. for 15 min, after which the samples were separated by SDS-PAGE and imaged using an ImageQuant LAS 4000 imager under the SYBR-Green setting. Samples were diluted prior to loading onto a gel, as follows: Input, 1:5; Wash 1:2; Beads 1:4.

EMSA. 5' biotinylated forward primers and unmodified reverse primers (see Table 3) were used to make probes. EMSAs were performed as described (Cho et al., 2006) using the LightShift Chemiluminescent EMSA Kit (Thermo) with the indicated quantities of proteins and probes noted in the figures/legends.

Confocal Microscopy. Overnight cultures, started from single colonies of *E. coli* (T7Express) carrying HALO and/or SNAP fusions (see Table 2) were back-diluted 1:1000, and grown at 37° C. to $OD_{600}$~0.2. Either MMC, aTc, or ethanol in water was added. The so-treated samples were returned to shaking at 37° C. for an additional 60 min prior to live-cell staining and imaging. Live-cell staining was performed using a protocol adapted from (Ke et al., 2016). Briefly, HALO-TMR was added to each sample at 10 µM. The samples were incubated in the dark for 15-20 min at 37° C. The cells were pelleted at 13,000 g×1 min, washed twice with M9 medium, and resuspended in 50-150 µL of fresh M9 medium. 5-10 µL of each sample was spotted onto a glass coverslip and overlaid with a small amount of M9-agar. The samples were imaged on a Leica SP8 Confocal microscope. HALO-TMR was excited with 561 nm light and detected within a range of 579-622 nm. For SNAP-Qtip co-localization experiments, the SNAP-specific dye $JF_{503}$ (Grimm et al., 2017) was added at 10 µM at the same time as the HALO-TMR reagent was added. SNAP was visualized by excitation at 504 nm and detection within 516-540 nm. All images were acquired under the same conditions (laser power and gain) in LASX (Leica Microsystems). Images were imported into Fiji for processing, which consisted solely of adjusting brightness and contrast (min-max).

A second aspect of the disclosed invention is drawn to a method for selectively lysing a bacterium. The method includes providing a disclosed engineered recombinant phage, contacting a target bacterium with the phage, and allowing the phage to lyse the bacterium.

Figure 4:
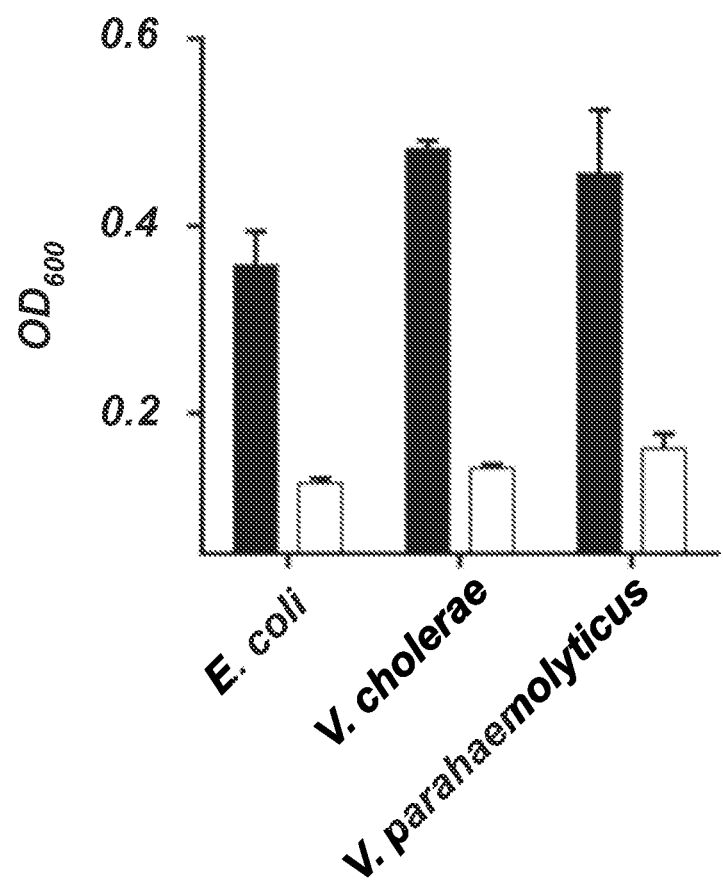
FIG. 4 is a graph showing the growth of $E.$ $coli$, $V.$ $cholerae$, and $V.$ $parahaemolyticus$ strains lysogenized with the generalized DPO-based phage kill switch in minimal medium lacking (black bars) or containing (white bars) 50 µM synthetic DPO to induce lysis, where all media contained arabinose.

To make a controllable kill switch on the phage, the arabinose-inducible $VqmA_{Phage}$ module can be introduced onto the phage genome along with an antibiotic resistance marker to select for acquisition of the module. Since the phage harbors the genes encoding the machinery for stable inheritance, there is no need to continue selection for the inducible module beyond initial selection for the recombinant phage. Referring to FIG. 4, in one embodiment, this phage is introduced into *E. coli*, *V. cholerae*, and *V. parahaemolyticus* (no arabinose, black bars). The addition of even a low concentration of arabinose (0.2% arabinose, white bars) causes lysis of all species, however, crucially, maximal lysis only occurs when DPO is also administered. Thus, the engineered phage acts as a DPO-dependent kill switch across different species.

Despite the ability to be maintained and to lyse non-natural hosts such as *E. coli*, the VP882 phage, and recombinants, appear only capable of infecting vibrios. This feature allows one to build and employ a non-pathogenic organism (e.g., *E. coli*) as a production and delivery vehicle to initiate a phage infection that selectively targets vibrios. Upon encountering DPO, the disclosed phage-mediated kill switch should kill the bacterial delivery vehicle, as well as any other bacteria (i.e., vibrios) to which the phage had been transferred prior to exposure to DPO. In considering the broad-generalized DPO-based killer), one can conceive of environmental and remediation contexts in which this engineered phage could be a useful, most notably, when it is essential to eliminate the host strain that is used to deliver the phage to the treatment site and/or when multiple species are simultaneously targeted. As an example, maritime applications aimed at limiting the transfer of pathogenic vibrios in ballast water to foreign harbors could potentially employ such a phage. Indeed, the onset of cholera epidemics and *V. parahaemolyticus* outbreaks have coincided with the detection of those organisms in ballast water, and thus it would be useful to eliminate both of them. Hypothetically, in this use, ballast water could be treated with a Δtdh *E. coli* pseudolysogen as a delivery vector. Because this host makes no DPO, it would maintain the pseudolysogen. *E. coli* naturally conjugates with vibrios, which could be the mechanism used to transfer the phage to the prey. Treatment of the ballast water with a $vqmA_{Phage}$ inducer (arabinose in our setup) will make the prophage become DPO sensitive. DPO is made by *V. cholerae* and *V. parahaemolyticus*, triggering the kill switch both in the delivery host and in the pathogen. Infective phage particles, produced by the lysed vibrios, could go on to infect other vibrios in the ballast water, propagating the infection of the target species. Obviously, design features would need to be established to ensure high level mating efficiency between delivery vehicle and prey. Likewise, safety features would need to be built into the phage to track the extent of killing, absence of phage particles, elimination of the host, etc.

A third aspect of the disclosed invention is a prophylactic treatment method for a high-risk individual. The method includes introducing the disclosed engineered recombinant phages, which are delivered by commensal bacteria to the high-risk individual prior to coming in contact with a pathogenic bacterium. The engineered recombinant phage includes a first DNA construct configured to drive a phage lytic program for the pathogenic bacterium, and where at least one regulator of a phage lytic gene is subject to a promoter that is activated by the pathogenic bacterium. In some embodiments, the promoter is induced by an external trigger or activated by a cue that is specifically produced by the pathogenic bacterium.

A fourth aspect of the disclosed invention is a method for manufacturing an engineered recombinant phage. The method involves providing a first gene adapted to drive a phage lytic program, and providing a first promoter, then integrating the first gene under the first promoter on a plasmid such that the phage is capable of responding to a host-produced quorum-sensing autoinducer. Embodiments of the method may include removing a natural lytic regulatory component of the phage, modifying the phage such that it does not respond to any of its native biological inputs, or a combination of the two.

In some embodiments, the first gene and/or the first promoter comprises either synthetic DNA or transgenic DNA.

In some embodiments, the integration of the first gene under the first promoter is accomplished via methods known to those of skill in the art, such as (i) in-vitro or in-vivo transposon mutagenesis, (ii) homologous recombination promoted by natural competence mechanisms or a suicide vector, (iii) recombineering with the lambda red system, restriction enzyme-based cloning or isothermal assembly, or (iv) genome editing using transcription activator-like effector nucleases (TALENs), zinc-finger nucleases (ZFNs), or clustered regulatory interspaced short palindromic repeat (CRISPR-Cas) based procedures.

A fifth aspect of the disclosed invention is a biomarker, utilizing an engineered recombinant phage that includes a DNA construct with a reporter tag, such as a fluorescent or luminescent reporter tag (e.g., mCherry, GFP, PADRON-C, etc.), subject to a promoter, wherein the phage is capable of responding to a host-produced quorum-sensing autoinducer.

A sixth aspect of the disclosed invention involves a system for inactivating a protein of interest. The system includes two promoters: (i) a first promoter controlling expression of a qtip gene, and (ii) a second promoter, such as a natural promoter of the protein of interest, controlling expression of a gene that encodes a phage repressor protein fused to a protein of interest, configured such that the phage repressor protein is capable of being inactivated by qtip.

In some embodiments, the first promoter may be activated by a specific species of bacteria, light-activated via a photoresponsive transcription factor, or activated by the presence of a chemical species such as a small molecule, a metabolite, or an artificial inducer.

A seventh aspect of the disclosed invention is a method for controlling the activity of a protein of interest, that includes providing a system as described above. Then, producing (i) a fusion protein containing the phage repressor protein fused to a protein of interest by expressing the gene that encodes the phage repressor protein fused to a protein of interest, and (ii) a Qtip protein by inducing expression of the qtip gene at a point in time after the fusion protein is produced. The Qtip protein is then allowed to inactivate the phage repressor protein.

What is claimed is:

1. An engineered recombinant phage, comprising a first DNA construct configured to drive a phage lytic program for a first bacterium, and where at least one regulator of a phage lytic gene is subject to a promoter,
wherein the engineered recombinant phage is a temperate phage, and
wherein the engineered recombinant phage is capable of detecting and responding to a host-produced quorum-sensing autoinducer, where detecting includes the host-produced quorum-sensing autoinducer binding to a phage-encoded quorum-sensing receptor.

2. The engineered recombinant phage according to claim 1, wherein the first DNA construct is configured to drive the phage lytic program for the first bacterium and an additional phage lytic program for an additional bacterium.

3. The engineered recombinant phage according to claim 1, wherein the engineered recombinant phage comprises a component from a phage that is specific to a second bacterium different from the first bacterium.

4. The engineered recombinant phage according to claim 1, wherein the at least one regulator of the phage lytic gene is a phage protein.

5. The engineered recombinant phage according to claim 4, wherein the phage protein is Qtip (quorum triggered inactivator of cI protein).

6. The engineered recombinant phage according to claim 1, wherein the at least one regulator of a phage lytic gene is a non-phage protein.

7. The engineered recombinant phage according to claim 1, wherein the at least one regulator of a phage lytic gene encodes a repressor.

8. The engineered recombinant phage according to claim 1, wherein the at least one regulator of a phage lytic gene encodes an antirepressor.

9. The engineered recombinant phage according to claim 1, wherein the promoter is activated by a specific species of bacteria.

10. The engineered recombinant phage according to claim 1, wherein the phage has been modified such that it does not respond to any of its native biological inputs.

11. The engineered recombinant phage according to claim 1, wherein the promoter is configured to be light-activated via a photoresponsive transcription factor.

12. The engineered recombinant phage according to claim 1, wherein the promoter is configured to be activated by the presence of a chemical species.

13. The engineered recombinant phage according to claim 12, wherein the chemical species is a small molecule, a metabolite, or an artificial inducer.

14. The engineered recombinant phage according to claim 1, wherein the engineered recombinant phage comprises a plurality of DNA constructs.

15. The engineered recombinant phage according to claim 14, wherein the phage further comprises a second DNA construct configured to prevent a phage lytic program, the second genetic construct having at least one regulator of a phage lytic gene subject to a promoter.

16. The engineered recombinant phage according to claim 14, wherein the phage further comprises a second DNA construct configured to lyse bacteria producing recombinant proteins.

17. A method for selectively lysing a bacterium, comprising the steps of:
providing an engineered recombinant phage according to claim 1;
contacting a target bacterium with the phage; and
allowing the phage to lyse the bacterium.

18. A prophylactic method for a high-risk individual, comprising the steps of:
introducing a plurality of engineered recombinant phages according to claim 1, which are delivered by commensal bacteria to the high-risk individual prior to coming in contact with a pathogenic bacterium;
wherein the engineered recombinant phage comprises a first DNA construct configured to drive a phage lytic program for the pathogenic bacterium, and where at least one regulator of a phage lytic gene is subject to a promoter that is activated by the pathogenic bacterium.

19. The prophylactic method according to claim 18, wherein the promoter is induced by an external trigger or activated by a cue that is specifically produced by the pathogenic bacterium.

20. A method for manufacturing an engineered recombinant temperate phage, comprising the steps of:
   providing a first gene adapted to drive a phage lytic program;
   providing a first promoter; and
   integrating the first gene under the first promoter on a plasmid,
   wherein the engineered recombinant temperate phage is capable of detecting and responding to a host-produced quorum-sensing autoinducer, where detecting includes the host-produced quorum-sensing autoinducer binding to a phage-encoded quorum-sensing receptor.

21. The method according to claim 20, further comprising removing a natural lytic regulatory component of the phage, modifying the phage such that it does not respond to any of its native biological inputs, or a combination thereof.

22. The method according to claim 20, wherein the first gene, the first promoter, or both comprises either synthetic DNA or transgenic DNA.

23. The method according to claim 20, wherein integrating is accomplished by a method selected from the group consisting of: in-vitro or in-vivo transposon mutagenesis, homologous recombination promoted by natural competence mechanisms or a suicide vector, recombineering with the lambda red system, restriction enzyme-based cloning or isothermal assembly, and genome editing using transcription activator-like effector nucleases (TALENs), zinc-finger nucleases (ZFNs), or clustered regulatory interspaced short palindromic repeat (CRISPR-Cas) based procedures.

24. An engineered recombinant temperate phage, comprising:
   a DNA construct having at least one reporter tag subject to a promoter, wherein the phage is capable of detecting and responding to a host-produced quorum-sensing autoinducer, where detecting includes the host-produced quorum-sensing autoinducer binding to a phage-encoded quorum-sensing receptor.

25. The engineered recombinant phage according to claim 24, wherein the reporter tag is a fluorescent or luminescent reporter tag.

26. A system for inactivating a protein of interest, comprising:
   a first promoter controlling expression of a qtip (quorum triggered inactivator of cI protein) gene; and
   a second promoter controlling expression of a gene that encodes a phage repressor protein fused to a protein of interest,
   wherein the phage repressor protein is capable of being inactivated by Qtip when Qtip is expressed and interacts with the phage repressor protein.

27. The system according to claim 26, wherein the second promoter is a natural promoter of the protein of interest.

28. The system according to claim 26, wherein the first promoter is activated by a specific species of bacteria, light-activated via a photoresponsive transcription factor, or activated by the presence of a chemical species.

29. The system according to claim 26, wherein the chemical species is a small molecule, a metabolite, or an artificial inducer.

30. A method for controlling the activity of a protein of interest, comprising the steps of:
   providing a system according to claim 26;
   producing a fusion protein containing the phage repressor protein fused to a protein of interest by expressing the gene that encodes the phage repressor protein fused to a protein of interest;
   producing a Qtip protein by inducing expression of the qtip gene at a point in time after the fusion protein is produced; and
   allowing the Qtip protein to inactivate the phage repressor protein.

* * * * *

SEQUENCE LISTING

```
<160> NUMBER OF SEQ ID NOS: 134

<210> SEQ ID NO 1
<211> LENGTH: 79
<212> TYPE: PRT
<213> ORGANISM: Vibrio cholerae

<400> SEQUENCE: 1

Met Cys Asp Phe Cys Ser Glu His Ile Asp Ser Leu Asp Ala Leu Gln
1               5                   10                  15

Ser Ser Leu Glu Lys Gly Thr Ala Ile Ile Glu Leu Leu Asp Thr Ala
            20                  25                  30

Leu Ser Ala Gly Ile Glu Val Ser Pro Arg Val Val Ser Cys Ala Leu
        35                  40                  45

Ser Ala Ala His Gln His Leu Gln Val Ser Glu Lys Ile Asn Arg Ser
    50                  55                  60

Leu Gln Ile Gly Cys Gly Ser Lys Glu Val Leu Arg Leu Val Asp
65                  70                  75

<210> SEQ ID NO 2
<211> LENGTH: 70
<212> TYPE: PRT
<213> ORGANISM: Vibrio cholerae

<400> SEQUENCE: 2

Met Asp Leu Arg Val Ser Asn Ala Lys Asp Leu Leu Asp Lys Phe Glu
1               5                   10                  15

Glu Lys Ala Val Gln Met Glu Ser Ile Ser Gln Leu Leu Ala Asn Ala
            20                  25                  30

Pro Glu Asp Leu Thr Leu Ala Thr Val Gln Gly Ser Leu Ser Ala Leu
```

```
                        35                  40                  45
Ala Ser Ile Ala Arg Asp Ala Gly Glu Ala Ala Asp Arg Leu Arg Thr
        50                  55                  60

Ile Ser Ser Ala Glu Gly
65                  70

<210> SEQ ID NO 3
<211> LENGTH: 100
<212> TYPE: PRT
<213> ORGANISM: Vibrio cholerae

<400> SEQUENCE: 3

Thr Cys Cys Gly Ala Gly Thr Ala Thr Gly Cys Gly Cys Gly Ala
1               5                   10                  15

Gly Cys Thr Gly Thr Ala Ala Thr Gly Thr Gly Ala Cys Thr Cys
                20                  25                  30

Ala Ala Ala Cys Ala Ala Thr Thr Ala Thr Gly Cys Ala Thr Ala Ala
                35                  40                  45

Ala Gly Gly Gly Gly Gly Ala Thr Thr Thr Cys Cys Cys Cys
        50                  55                  60

Cys Thr Thr Thr Thr Thr Cys Ala Thr Thr Gly Thr Ala Cys Cys
65                  70                  75                  80

Gly Cys Gly Thr Thr Cys Gly Gly Thr Ala Ala Ala Gly Thr Ala Cys
                        85                  90                  95

Ala Ala Ala Cys
            100

<210> SEQ ID NO 4
<211> LENGTH: 108
<212> TYPE: PRT
<213> ORGANISM: Vibrio cholerae

<400> SEQUENCE: 4

Thr Thr Ala Thr Cys Ala Ala Thr Thr Thr Ala Gly Cys Ala Gly
1               5                   10                  15

Cys Thr Gly Cys Thr Thr Ala Thr Cys Ala Gly Gly Gly Thr Ala Thr
                20                  25                  30

Thr Thr Thr Thr Cys Cys Cys Cys Cys Thr Ala Thr Cys Gly Gly Thr
            35                  40                  45

Ala Thr Thr Thr Cys Thr Thr Ala Thr Ala Gly Cys Ala Thr Cys
        50                  55                  60

Ala Ala Gly Ala Ala Thr Ala Ala Ala Gly Cys Thr Cys Cys Thr Thr
65                  70                  75                  80

Ala Thr Ala Ala Cys Ala Ala Thr Cys Ala Cys Thr Thr Ala Cys Ala
                        85                  90                  95

Ala Gly Gly Ala Gly Thr Gly Thr Ala Thr Thr Cys
            100                 105

<210> SEQ ID NO 5
<211> LENGTH: 33
<212> TYPE: PRT
<213> ORGANISM: Vibrio cholerae

<400> SEQUENCE: 5

Ala Ala Thr Cys Gly Ala Ala Ala Ala Ala Gly Ala Gly Cys Thr Cys
1               5                   10                  15

Cys Gly Cys Gly Gly Cys Gly Ala Cys Cys Thr Gly Thr Thr Cys Cys
                20                  25                  30
```

Ala

<210> SEQ ID NO 6
<211> LENGTH: 35
<212> TYPE: PRT
<213> ORGANISM: Vibrio cholerae

<400> SEQUENCE: 6

```
Gly Ala Ala Thr Ala Cys Ala Cys Thr Cys Cys Thr Thr Gly Thr Ala
1               5                   10                  15

Ala Gly Thr Gly Ala Thr Thr Gly Thr Thr Ala Thr Ala Ala Gly Gly
            20                  25                  30

Ala Gly Cys
        35
```

<210> SEQ ID NO 7
<211> LENGTH: 35
<212> TYPE: PRT
<213> ORGANISM: Vibrio cholerae

<400> SEQUENCE: 7

```
Thr Gly Thr Thr Cys Gly Ala Thr Ala Ala Thr Thr Ala Thr Thr Thr
1               5                   10                  15

Gly Gly Thr Cys Thr Thr Cys Gly Gly Thr Cys Ala Thr Thr Thr Thr
            20                  25                  30

Thr Cys Cys
        35
```

<210> SEQ ID NO 8
<211> LENGTH: 22
<212> TYPE: PRT
<213> ORGANISM: Vibrio cholerae

<400> SEQUENCE: 8

```
Cys Cys Ala Cys Gly Gly Ala Ala Thr Ala Gly Gly Ala Gly Gly Thr
1               5                   10                  15

Gly Thr Thr Thr Ala Gly
            20
```

<210> SEQ ID NO 9
<211> LENGTH: 21
<212> TYPE: PRT
<213> ORGANISM: Vibrio cholerae

<400> SEQUENCE: 9

```
Gly Ala Gly Gly Gly Ala Thr Ala Thr Cys Cys Ala Thr Thr Ala Cys
1               5                   10                  15

Gly Cys Cys Ala Gly
            20
```

<210> SEQ ID NO 10
<211> LENGTH: 857
<212> TYPE: DNA
<213> ORGANISM: Artificial Sequence
<220> FEATURE:
<223> OTHER INFORMATION: Synthetic Polynucleotide

<400> SEQUENCE: 10

```
tagcattttt atccataaga ttagcggatc ctacctgacg cttttatcg caactctcta      60 ctgtttctcc ggtacctgca ggaggtgtga aatgtcaata agcgaagggg atgatgctta    120
```

| | |
|---|---|
| catccgctcg ttgattcatt tttttggcaa tcaaccggat ccgtggggca tcaaggacac | 180 |
| caagtcggtg ttcatctatg caaaccagcc cttcgagag ttagtcggta tgaagaaccg | 240 |
| caacgtggaa ggacttaccg acgctgatat ggattgcgaa actgcggcct tgccgactc | 300 |
| ctttcaggcc caagataggc tggtcgagca aggccgggaa agaaaatcg tcctggacgt | 360 |
| acacccctac gcgaatggtt ggcgcgtttt cactttcacc aagacccctc tcatcatgcc | 420 |
| gtccggacgt gtggccggca ccattttcca cggacaagac ctgactgaca cggctggccg | 480 |
| catcgagcgt gcagtggttg agctgctgct gccttccagt ggccaggctg gatccttcga | 540 |
| gaccaatgtg gtcggtctca acttgaccga acgcgaggaa ctggtgctgt tcttcctgct | 600 |
| tcgtggccga acggccaagg atatcgctgg catgctgggg cgctctcccc gcaccatcga | 660 |
| acacgctatc gagcgcatcc gcaacaaatt cggtgctggc aacaagcggg agctcatcga | 720 |
| tatggccatg tccaagggtt attacagcat ggtgccaaaa gccctgtttc acacacaggt | 780 |
| ctcgatgctg ctcaagtagc gcaaccagga tccggtgatt gattgagcaa gctttatgct | 840 |
| tgtaaaccgt tttgtga | 857 |

<210> SEQ ID NO 11
<211> LENGTH: 1542
<212> TYPE: DNA
<213> ORGANISM: Artificial Sequence
<220> FEATURE:
<223> OTHER INFORMATION: Synthetic Polynucleotide

<400> SEQUENCE: 11

| | |
|---|---|
| tagcattttt atccataaga ttagcggatc ctacctgacg ctttttatcg caactctcta | 60 |
| ctgtttctcc ggtacctgca ggaggtgtga aatggatttg agcacccttta tcgccctgct | 120 |
| gactctgatt gtgctggttg tcggtggttt gctctccctc ctttgggaa aggtgaacag | 180 |
| catctctcag cagctggccg acgagcgtgt ccggtctgcc gagaagtaca tcacctctca | 240 |
| cgaaatggaa cggcgcctcg agcaagccat tgcaccgctg agcgaacgc tcgagcggat | 300 |
| ggaaaaccag aacaaccaga tttccagct gttgcgccgc cactaccacg cggaggccaa | 360 |
| ctaatggaca gcagcaagc gaaatcaatc gccatcaacg aagtgatcga acgtgaaggc | 420 |
| ggctatgtga atcacccgga tgaccgaggc ggccctactc gctgggcgt tacccaggcg | 480 |
| aaggctcggg agcacggtta tcacggtgac atgcgcgact atccggtcga ggcagctttc | 540 |
| gctgtttatg acgcggatta ttggcagcgc atgaagctgg acgaaattgg cgactacagc | 600 |
| ccagacctgg ctgtgaagct gttcgacttc ggtgtgaaca gtggaacggg ccgggcggct | 660 |
| cgtcattttc aacggttgct caactcactg aacaaccgcg gcgagtttta tccggacatt | 720 |
| aaggtcgacg gcgctatcgg tcaaaagacc ctggcttcgc tggccggctt ctaccgcaag | 780 |
| cgcggtgagg caggcttggc cgttctggcc cagtcgctta acggcctgcg cattgctttt | 840 |
| tgcgttggca tcactgagga caacgagtcg caggaagtat tcgccttgg ctggttgtct | 900 |
| cgcatcgttc atttgtaagg agctgaaatg gaacctttga ccattgcgct cggcctggcc | 960 |
| aagttgaccg ggctggataa gaaaatcggc cgctggattg gtggcgacaa tggcgaggag | 1020 |
| gttgccgaga aggttgtctc catcgcccag caggtaacgg gcgccaagaa tggcgatcag | 1080 |
| gcgctggcca agctggaagc caaccctgag cagttgattg agttcgagca ggcaatgcac | 1140 |
| gagcacgaac tgcacctcga ggagctggcc tataaagacc gcgctgatgc tcgagcgatg | 1200 |
| caagtggcgc gctacaggg taacgatacc ctgtctaagc gtttcgtcta ttacttcgct | 1260 |
| atcggatgga gcctgttcgc tttcctgtac ctgggcttca ttactttcgg ggatatcccg | 1320 |

```
gaagcaaaca tccgctttgc tgacactgtc ctgggcttcc tgctcggtac agtactcgct   1380
ggcatgttcg gcttcttcta tggctcaagc gccgggaacg aacgtcgagc agagcagcaa   1440
gacttgcacg ccgcgctaac gccgcggcgc cgctagtttt ctccacttct agggatccgg   1500
tgattgattg agcaagcttt atgcttgtaa accgttttgt ga                      1542

<210> SEQ ID NO 12
<211> LENGTH: 795
<212> TYPE: DNA
<213> ORGANISM: Artificial Sequence
<220> FEATURE:
<223> OTHER INFORMATION: Synthetic Polynucleotide

<400> SEQUENCE: 12
tagcattttt atccataaga ttagcggatc ctacctgacg cttttatcg caactctcta     60 ctgtttctcc ggtacctgca ggaggtgtga atgagagta cgggaataca acgagcagca    120
acttgactgg gtgcgccttc gaatctttca ggcgcattcg ctgcatatca agggtaagcc   180
attgtttgag ggcacgcagt actgtgttcc ggcctctcac ataaaacgcg ccaagacgaa   240
agaagaacga atcgaaaaag agctccgcgc cgacctgttc caggtgaagg gccgagagtc   300
tcgcaggggg aaaagttcca tgccattgcc gccttgggca ttcgaggata gcagagtcgt   360
ccgcgtggtg aatgccctcc ctgatggcca gcgccattgg atcatgtacg catacagcga   420
ctgctacaac tgggacaatg agtccggtgc ggttgtcgct ctctggaaag agttcgagcc   480
agagctggaa ggtgttcgcg atgacaccct gcagaagctg aaaggcatgg cttacctctg   540
tgtccaggac ttcaagaaca tcaagaaccg aggcaagcct gcacacttgc cctcacgcat   600
tcgccagctg actggcgtgc cagagggaaa ctggcggcgt gactggttgc cgcgctggag   660
acgaatgcag caaatcctga ctgagttcga ccgtgcggcc ctggccaagg tgatggaggt   720
gatttgtgac cgacacgttg cctaaggatc cggtgattga ttgagcaagc tttatgcttg   780
taaaccgttt tgtga                                                    795

<210> SEQ ID NO 13
<211> LENGTH: 973
<212> TYPE: DNA
<213> ORGANISM: Artificial Sequence
<220> FEATURE:
<223> OTHER INFORMATION: Synthetic Polynucleotide

<400> SEQUENCE: 13
tagcattttt atccataaga ttagcggatc ctacctgacg cttttatcg caactctcta     60 ctgtttctcc ggtacctgca ggaggtgtga agtgcatatt cgcagaaaaa ttttcaattc   120
tattcttact atccgcattg atgccagact tttttcgacg gattataaga tgatgaattt   180
tggtaacgtc ataagacgac ttaggaaggc taaaggctgg actcttcaac gtgtctgcga   240
agagatgaat ggtgccattc agaccggtca cttatctcgc attgagcgag gtgaactgac   300
gccatccgtt tacatagcac gcaacattgc ccgatcgctt ggtacctcac tggataccat   360
gcttgccgag gccgatgggg ggccgctcgc ccaagtggta ccggatccag cgcagcgggt   420
tccggtactt tcatgggtgc aagctggcct ctggacttcc tcgccaactg gcgtggtgcc   480
tgagctgtgc gataaatggg tggttgcgcc aagggccaag ttaccgcccc ggtgttatgc   540
actggaggta aggggcgaca gcatgcaagc gcagtatggc atgagcttcc cggaggggtg   600
ctacatcatc gtggatccga accgcgtgcc tgaaaacaag tcctttgtcg tggcgatgca   660
```

```
aacgaacgcg gaagaggcca cattcaagca gctgatcatc gagggcgcgg acaagtattt    720
gaagccgtta aacccacaat atccactgct taaaattgac caagaagtaa tcacttgtgg    780
cgttgttatc gatatggtgt gtcatctggc aaatggtcac tgataaaacg cagcagttat    840
aatttgcgaa aagtgagaaa attagcttaa actagggcag ccatagaagc ctatcggctg    900 cattttgtg caaggttaga tatggatccg gtgattgatt gagcaagctt tatgcttgta    960
aaccgttttg tga                                                       973
```

<210> SEQ ID NO 14
<211> LENGTH: 569
<212> TYPE: DNA
<213> ORGANISM: Artificial Sequence
<220> FEATURE:
<223> OTHER INFORMATION: Synthetic Polynucleotide

<400> SEQUENCE: 14

```
tagcattttt atccataaga ttagcggatc ctacctgacg cttttatcg caactctcta     60 ctgtttctcc ggtacctgca ggaggtgtga agtgtgtgat ttttgcagtg aacacatcga    120
ctctttagac gccctacaat ccagcctgga aaaaggtact gccatcatcg agctactgga    180
caccgcgctt agtgccggta tcgaggtaag cccgagggtg gtatcgtgtg ccctgtctgc    240
tgcccaccag caccttcagg tatcggaaaa aataaaccgc agcctgcaaa taggctgcgg    300
ttcaaaggag gtgcttcgcc ttgttgatta gtcatcgagt gccttttggc tggcctccca    360
tgcggctgtc attgcctcaa cgcgggtgcc cttgattttc accctggcca cctcctcgcc    420
ttccaccagc gcccaggctt cccagtgctc atcatcaacc tggtgagcca cgagtctggg    480
cttctgcgct ttcttcggct gttttcttta gcgcaaccag gatccggtga ttgattgagc    540
aagctttatg cttgtaaacc gttttgtga                                      569
```

<210> SEQ ID NO 15
<211> LENGTH: 737
<212> TYPE: DNA
<213> ORGANISM: Artificial Sequence
<220> FEATURE:
<223> OTHER INFORMATION: Synthetic Polynucleotide

<400> SEQUENCE: 15

```
gccaaccact gaggatctgt actttcagag cgataacgcg atagaaatag atattggccc     60
ggtattaaag cgcatccgtt atgagcgagg gctaacgcta caaaagctgt cacggcttac    120
ggatgacaaa gtgctaccaa gcaacatttc ccgcatcgag agtgcgggcg ctggcgctac    180
gcttaaaacc ttgaccacct tggcgaatgc gctggggact tctccttctg acattcttcg    240
tgaagctgag ggcggtgata aggtgatcac caagccgcag caagtccttt atgtacctgt    300
tttgtcttgg gttcaggctg gcacctggac tgaatcacca gagcagcctg ccgatggtga    360
ctatgatgaa tgggtagagg caccaagagg cgcatccagg aaggctttcg gccttcgagt    420
tcaaggggat agtatgcaag cccctatcgg caagtcgttc ccggaaggat gctgcatagt    480
tgttgaccca accaaacaag cagataaccg ctcgtttgtt gttgctcgcc tggcagacac    540
aggagagcac acgttcaagc agctgatcat tgacgggccg caccaatatc taagccgct     600 aaacccaagt taccgaacca tagaagtgaa cagcgaagta cacgtctgcg gggtcgtttt    660
agcatggggt gaagggtaca cggtgaacgg tatttaatta attaaccaat tcctgcagga    720
ttttgcggcc gcttgct                                                   737
```

<210> SEQ ID NO 16
<211> LENGTH: 716
<212> TYPE: DNA
<213> ORGANISM: Artificial Sequence
<220> FEATURE:
<223> OTHER INFORMATION: Synthetic Polynucleotide

<400> SEQUENCE: 16

```
gccaaccact gaggatctgt actttcagag cgataacgcg actttagggc aagtaatcag    60
acggatacgc cacgccaaac aatggacgct acagcggact tgcgaagaag tggacttcca   120
aattcaacca ggacacctct cccgtattga gcggggcgag ggaattccat ccatacactt   180
tgtaaatatc atttccaaag cgcttggcgt ttctatagac gcgataatgg aagaggttga   240
aggtaaaagg cctgtaaaag tatcaaccac agaacccatc ccttacctac caatagtctc   300
atgggtccaa gcaggatcct ggaccgactc cccaccggcg cagaccctc tcagctgtga    360
tgactgggtg atagccccta agaaactccc aaagaactgc tatgcattgc gcgtagtagg   420
cgacagcatg accgcaccat acggcccatc gttccctgat ggctgcatta tcattgttga   480
ccccaccaaa cagcctgaga caagagtttt gttgttgca aggcaggaag ctcagacga    540
agcaaccttc aaacaactag ccattgaagg cggaacaaga tacttaaagc cactgaatca   600
acaataccca ctgattcaga taaatggcga cactaggttc tgcggagtcg tgaccttcat   660
aatttcacaa atctagttaa ttaaccaatt cctgcaggat tttgcggccg cttgct       716
```

<210> SEQ ID NO 17
<211> LENGTH: 791
<212> TYPE: DNA
<213> ORGANISM: Artificial Sequence
<220> FEATURE:
<223> OTHER INFORMATION: Synthetic Polynucleotide

<400> SEQUENCE: 17

```
gccaaccact gaggatctgt actttcagag cgataacgcg agcacaaaaa agaaaccatt    60
aacacaagag cagcttgagg acgcacgtcg ccttaaagca atttatgaaa aaagaaaaa   120
tgaacttggc ttatcccagg aatctgtcgc agacaagatg gggatggggc agtcaggcgt   180
tggtgcttta tttaatggca tcaatgcatt aaatgcttat aacgccgcat tgcttgcaaa   240
aattctcaaa gttagcgttg aagaatttag ccttcaatc gccagagaaa tctacgagat    300
gtatgaagcg gttagtatgc agccgtcact tagaagtgag tatgagtacc ctgttttttc   360
tcatgttcag gcagggatgt ctcacctga gcttagaacc tttaccaaag gtgatgcgga    420
gagatgggta agcacaacca aaaaagccag tgattctgca ttctggcttg aggttgaagg   480
taattccatg accgcaccaa caggctccaa gccaagcttt cctgacggaa tgttaattct   540
cgttgaccct gagcaggctg ttgagccagg tgatttctgc atagccagac ttggggtga    600
tgagtttacc ttcaagaaac tgatcaggga tagcggtcag gtgttttac aaccactaaa    660
cccacagtac ccaatgatcc catgcaatga gagttgttcc gttgtgggga agttatcgc    720
tagtcagtgg cctgaagaga cgtttggctg attaattaac caattcctgc aggattttgc   780
ggccgcttgc t                                                        791
```

<210> SEQ ID NO 18
<211> LENGTH: 365
<212> TYPE: DNA
<213> ORGANISM: Artificial Sequence
<220> FEATURE:
<223> OTHER INFORMATION: Synthetic Polynucleotide

```
<400> SEQUENCE: 18
cctatcagtg atagagaaaa gtgaaatggg agctccacag gaggtgtgaa atggatttaa      60
gggtttcaaa cgctaaggat ttattggata agttcgagga gaaagctgta cagatggaat     120
caatcagcca gttactggct aatgcgccgg aggatctgac gctggccacc gtgcaaggta     180
gtctatcggc attggcatcg atcgccaggg atgccgggga ggctgctgat cgcctgagga     240
cgatcagcag tgcggaaggt tagtcgcggt tgcggaagat gttccaggcc gcggcgatcg     300
ctgcagccct ggagctcatc gagtgccttt tggctggcct cccatgcggc tgtcattgcc     360
tcaac                                                                 365

<210> SEQ ID NO 19
<211> LENGTH: 943
<212> TYPE: DNA
<213> ORGANISM: Artificial Sequence
<220> FEATURE:
<223> OTHER INFORMATION: Synthetic Polynucleotide

<400> SEQUENCE: 19
cctatcagtg atagagaaaa gtgaaatggg agctccacag gaggtgtgaa atggacaaag      60
attgcgaaat gaaacgtacc accctggata gcccgctggg caaactggaa ctgagcggct     120
gcgaacaggg cctgcatgaa attaaactgc tgggtaaagg caccagcgcg gccgatgcgg     180
ttgaagttcc ggccccggcc gccgtgctgg gtggtccgga accgctgatg caggcgaccg     240
cgtggctgaa cgcgtatttt catcagccgg aagcgattga agaatttccg gttccggcgc     300
tgcatcatcc ggtgtttcag caggagagct ttacccgtca ggtgctgtgg aaactgctga     360
aagtggttaa atttggcgaa gtgattagct atcagcagct ggcggccctg cgggtaatc      420
cggcggccac cgccgccgtt aaaccgcgc tgagcggtaa cccggtgccg attctgattc      480
cgtgccatcg tgtggttagc tctagcggtg cggttggcgg ttatgaaggt ggtctggcgg     540
tgaaagagtg gctgctggcc catgaaggtc atcgtctggg taaaccgggt ctgggacctg     600
caggcggatc cggcgagcca accactgagg atctgtactt tcagagcgat aacgcgtgtg     660
attttttgcag tgaacacatc gactctttag acgccctaca atccagcctg aaaaaggta     720
ctgccatcat cgagctactg gacaccgcgc ttagtgccgg tatcgaggta agcccgaggg     780
tggtatcgtg tgccctgtct gctgccacc agcaccttca ggtatcggaa aaataaaacc     840
gcagcctgca ataggctgc ggttcaaagg aggtgcttcg ccttgttgat tagtcatcga     900
gtgccttttg gctggcctcc catgcggctg tcattgcctc aac                       943

<210> SEQ ID NO 20
<211> LENGTH: 323
<212> TYPE: DNA
<213> ORGANISM: Artificial Sequence
<220> FEATURE:
<223> OTHER INFORMATION: Synthetic Polynucleotide

<400> SEQUENCE: 20
gggtcttttt gcatgcggcg ggtaccgctc gagttaatta atattttaaa tcagcaaaca      60
ctatgcaagt tggccaattt aattagcggg cggcatcagt ttcataatga ttgcatcagg     120
attttgccac ccgctcccgg tattgtttac atattaaaat gattttaaac tggtgctgac     180
aactatgcta aatacgcagg aagtacttaa agaaggagag aagcggaaaa tccgcagccc     240
ggaagcatgt tttatacaga cgtgttccgc gcaaaagctg catatgagag tacgggaata     300
caacgagcag caacttgact ggg                                             323
```

<210> SEQ ID NO 21
<211> LENGTH: 1030
<212> TYPE: DNA
<213> ORGANISM: Artificial Sequence
<220> FEATURE:
<223> OTHER INFORMATION: Synthetic Polynucleotide

<400> SEQUENCE: 21

```
cctatcagtg atagagaaaa gtgaaatggg agctccacag gaggtgtgaa atggaaaatg      60
taacctttgt aagtaatagt catcagcgtc ctgccgcaga taacttacag aaattaaaat     120
cacttttgac aaatacccgg cagcaaatta aaagtcagac tcagcaggtt accatcaaaa     180
atctttatgt aagcagtttc actttagttt gctttcggag cggtaaactg acgattagca     240
ataatcacga tacgatttac tgtgacgaac tgggatgtt ggtgctcaaa aaagagcagg      300
tagttaacgt gacgcttgaa gaggtcaatg gccacatgga tttcgatata ctcgagatac     360
cgacgcaacg acttggcgct ctctatgcac ttatcccaaa cgagcagcaa accaaaatgg     420
cggtacccac agagaaagcg cagaagatct tctatacgcc tgactttcct gccagaagag     480
aggtatttga acatctgaaa acggcgttct cctgtacgaa ggatacaagc aaaggttgca     540
gtaactgtaa caacaaaagt tgtattgaaa atgaagagtt aattccttat tttctgctgt     600
tcctgcttac tgcttttctc cgactcccgg agagttatga gatcatcctt agctcggctc     660
agataacgtt aaaggagcgc gtttacaaca ttatatcttc gtcacccagt agacagtgga     720
agcttacgga tgttgccgat catatattta tgagtacgtc aacgctcaaa cggaaacttg     780
cagaagaagg taccagcttt agcgacatct acttatcggc aagaatgaat caggcagcaa     840
aacttttacg cataggcaac cataatgtta atgctgtagc attaaaatgt ggttatgata     900
gcacgtccta cttcattcaa tgtttcaaaa aatatttaa aactacgcca tcgacattca      960
taaaaatggc gaaccattaa tcatcgagtg ccttttggct ggcctcccat gcggctgtca    1020
ttgcctcaac                                                            1030
```

<210> SEQ ID NO 22
<211> LENGTH: 20
<212> TYPE: PRT
<213> ORGANISM: Artificial Sequence
<220> FEATURE:
<223> OTHER INFORMATION: Primer

<400> SEQUENCE: 22

```
Gly Cys Ala Thr Thr Thr Cys Cys Ala Gly Thr Gly Ala Gly Gly
1               5                   10                  15

Ala Thr Ala Thr
            20
```

<210> SEQ ID NO 23
<211> LENGTH: 32
<212> TYPE: PRT
<213> ORGANISM: Artificial Sequence
<220> FEATURE:
<223> OTHER INFORMATION: Primer

<400> SEQUENCE: 23

```
Gly Thr Thr Thr Thr Thr Gly Gly Ala Thr Cys Cys Ala Ala Thr Cys
1               5                   10                  15

Ala Gly Cys Thr Thr Gly Ala Cys Gly Thr Thr Gly Thr Thr Gly Cys
                20                  25                  30
```

```
<210> SEQ ID NO 24
<211> LENGTH: 22
<212> TYPE: PRT
<213> ORGANISM: Artificial Sequence
<220> FEATURE:
<223> OTHER INFORMATION: Primer

<400> SEQUENCE: 24

Gly Thr Cys Gly Ala Cys Ala Ala Thr Gly Ala Ala Gly Gly Gly Thr
1               5                   10                  15

Cys Thr Thr Thr Thr Ala
            20

<210> SEQ ID NO 25
<211> LENGTH: 27
<212> TYPE: PRT
<213> ORGANISM: Artificial Sequence
<220> FEATURE:
<223> OTHER INFORMATION: Primer

<400> SEQUENCE: 25

Gly Thr Thr Thr Thr Thr Thr Gly Gly Ala Thr Cys Cys Gly Gly Thr
1               5                   10                  15

Gly Ala Thr Thr Gly Ala Thr Thr Gly Ala Gly
            20                  25

<210> SEQ ID NO 26
<211> LENGTH: 20
<212> TYPE: PRT
<213> ORGANISM: Artificial Sequence
<220> FEATURE:
<223> OTHER INFORMATION: Primer

<400> SEQUENCE: 26

Thr Cys Thr Ala Gly Ala Ala Gly Ala Ala Gly Cys Thr Thr Gly Gly
1               5                   10                  15

Gly Ala Thr Cys
            20

<210> SEQ ID NO 27
<211> LENGTH: 19
<212> TYPE: PRT
<213> ORGANISM: Artificial Sequence
<220> FEATURE:
<223> OTHER INFORMATION: Primer

<400> SEQUENCE: 27

Cys Thr Gly Thr Thr Gly Cys Ala Thr Gly Gly Cys Ala Thr Ala
1               5                   10                  15

Ala Ala Gly

<210> SEQ ID NO 28
<211> LENGTH: 18
<212> TYPE: PRT
<213> ORGANISM: Artificial Sequence
<220> FEATURE:
<223> OTHER INFORMATION: Primer

<400> SEQUENCE: 28

Thr Thr Cys Ala Cys Ala Cys Cys Cys Cys Thr Gly Thr Ala Cys
1               5                   10                  15

Gly Cys
```

```
<210> SEQ ID NO 29
<211> LENGTH: 44
<212> TYPE: PRT
<213> ORGANISM: Artificial Sequence
<220> FEATURE:
<223> OTHER INFORMATION: Primer

<400> SEQUENCE: 29

Gly Thr Thr Thr Thr Thr Thr Gly Ala Gly Cys Thr Cys Thr Gly Thr
1               5                   10                  15

Thr Thr Ala Thr Gly Thr Ala Ala Gly Cys Ala Gly Ala Cys Ala Gly
            20                  25                  30

Thr Thr Thr Thr Ala Thr Thr Gly Thr Thr Cys Ala
        35                  40

<210> SEQ ID NO 30
<211> LENGTH: 31
<212> TYPE: PRT
<213> ORGANISM: Artificial Sequence
<220> FEATURE:
<223> OTHER INFORMATION: Primer

<400> SEQUENCE: 30

Thr Ala Ala Thr Cys Ala Gly Ala Ala Thr Thr Gly Gly Thr Thr Ala
1               5                   10                  15

Ala Thr Thr Gly Gly Thr Thr Gly Thr Ala Ala Cys Ala Cys Thr
            20                  25                  30

<210> SEQ ID NO 31
<211> LENGTH: 21
<212> TYPE: PRT
<213> ORGANISM: Artificial Sequence
<220> FEATURE:
<223> OTHER INFORMATION: Primer

<400> SEQUENCE: 31

Gly Gly Ala Thr Cys Cys Gly Gly Thr Gly Ala Thr Thr Gly Ala Thr
1               5                   10                  15

Thr Gly Ala Gly Cys
            20

<210> SEQ ID NO 32
<211> LENGTH: 25
<212> TYPE: PRT
<213> ORGANISM: Artificial Sequence
<220> FEATURE:
<223> OTHER INFORMATION: Primer

<400> SEQUENCE: 32

Gly Gly Ala Gly Ala Ala Ala Cys Ala Gly Thr Ala Gly Ala Gly Ala
1               5                   10                  15

Gly Thr Thr Gly Cys Gly Ala Thr Ala
            20                  25

<210> SEQ ID NO 33
<211> LENGTH: 34
<212> TYPE: PRT
<213> ORGANISM: Artificial Sequence
<220> FEATURE:
<223> OTHER INFORMATION: Primer

<400> SEQUENCE: 33

Ala Thr Gly Ala Cys Thr Ala Ala Ala Ala Ala Ala Thr Thr Thr Thr
1               5                   10                  15
```

Cys Ala Thr Thr Cys Ala Thr Thr Ala Thr Ala Ala Cys Gly Gly
            20                  25                  30

Cys Cys

<210> SEQ ID NO 34
<211> LENGTH: 27
<212> TYPE: PRT
<213> ORGANISM: Artificial Sequence
<220> FEATURE:
<223> OTHER INFORMATION: Primer

<400> SEQUENCE: 34

Cys Cys Ala Thr Thr Cys Cys Ala Ala Cys Ala Thr Thr Ala
1               5                   10                  15

Cys Cys Thr Ala Cys Cys Ala Thr Thr Ala Ala
            20                  25

<210> SEQ ID NO 35
<211> LENGTH: 21
<212> TYPE: PRT
<213> ORGANISM: Artificial Sequence
<220> FEATURE:
<223> OTHER INFORMATION: Primer

<400> SEQUENCE: 35

Gly Gly Ala Thr Cys Cys Gly Gly Thr Gly Ala Thr Thr Gly Ala Thr
1               5                   10                  15

Thr Gly Ala Gly Cys
            20

<210> SEQ ID NO 36
<211> LENGTH: 21
<212> TYPE: PRT
<213> ORGANISM: Artificial Sequence
<220> FEATURE:
<223> OTHER INFORMATION: Primer

<400> SEQUENCE: 36

Cys Ala Cys Ala Thr Thr Gly Gly Thr Cys Thr Cys Gly Ala Ala Gly
1               5                   10                  15

Gly Ala Thr Cys Cys
            20

<210> SEQ ID NO 37
<211> LENGTH: 35
<212> TYPE: PRT
<213> ORGANISM: Artificial Sequence
<220> FEATURE:
<223> OTHER INFORMATION: Primer

<400> SEQUENCE: 37

Gly Ala Ala Thr Ala Cys Ala Cys Thr Cys Cys Thr Gly Thr Ala
1               5                   10                  15

Ala Gly Thr Gly Ala Thr Thr Gly Thr Thr Ala Thr Ala Ala Gly Gly
            20                  25                  30

Ala Gly Cys
        35

<210> SEQ ID NO 38
<211> LENGTH: 23
<212> TYPE: PRT
<213> ORGANISM: Artificial Sequence
<220> FEATURE:
<223> OTHER INFORMATION: Primer -continued

```
<400> SEQUENCE: 38

Cys Cys Ala Ala Ala Gly Cys Cys Thr Gly Thr Thr Thr Cys
1               5                   10                  15

Ala Cys Ala Cys Ala Cys Ala
            20

<210> SEQ ID NO 39
<211> LENGTH: 35
<212> TYPE: PRT
<213> ORGANISM: Artificial Sequence
<220> FEATURE:
<223> OTHER INFORMATION: Primer

<400> SEQUENCE: 39

Thr Gly Thr Thr Cys Gly Ala Thr Ala Ala Thr Ala Thr Thr Thr
1               5                   10                  15

Gly Gly Thr Cys Thr Thr Cys Gly Gly Thr Cys Ala Thr Thr Thr
                20                  25                  30

Thr Cys Cys
        35

<210> SEQ ID NO 40
<211> LENGTH: 43
<212> TYPE: PRT
<213> ORGANISM: Artificial Sequence
<220> FEATURE:
<223> OTHER INFORMATION: Primer

<400> SEQUENCE: 40

Ala Gly Ala Ala Thr Cys Thr Thr Thr Ala Thr Thr Thr Cys Ala
1               5                   10                  15

Gly Gly Gly Cys Ala Thr Gly Thr Cys Ala Ala Thr Ala Ala Gly Cys
                20                  25                  30

Gly Ala Ala Gly Gly Gly Gly Ala Thr Gly Ala
        35                  40

<210> SEQ ID NO 41
<211> LENGTH: 38
<212> TYPE: PRT
<213> ORGANISM: Artificial Sequence
<220> FEATURE:
<223> OTHER INFORMATION: Primer

<400> SEQUENCE: 41

Thr Thr Cys Gly Gly Gly Cys Thr Thr Gly Thr Thr Ala Gly Cys
1               5                   10                  15

Ala Gly Cys Cys Gly Gly Ala Thr Cys Cys Thr Gly Gly Thr Gly
                20                  25                  30

Cys Gly Cys Thr Ala Cys
        35

<210> SEQ ID NO 42
<211> LENGTH: 44
<212> TYPE: PRT
<213> ORGANISM: Artificial Sequence
<220> FEATURE:
<223> OTHER INFORMATION: Primer

<400> SEQUENCE: 42

Thr Cys Cys Cys Cys Thr Thr Cys Gly Cys Thr Thr Ala Thr Thr Gly
1               5                   10                  15
```

Ala Cys Ala Thr Gly Cys Cys Thr Gly Ala Ala Ala Thr Ala
            20                  25                  30

Ala Ala Gly Ala Thr Thr Cys Thr Cys Gly Cys Cys
        35                  40

<210> SEQ ID NO 43
<211> LENGTH: 40
<212> TYPE: PRT
<213> ORGANISM: Artificial Sequence
<220> FEATURE:
<223> OTHER INFORMATION: Primer

<400> SEQUENCE: 43

Cys Thr Gly Cys Thr Cys Ala Ala Gly Thr Ala Gly Cys Gly Cys Ala
1               5                   10                  15

Ala Cys Cys Ala Gly Gly Ala Thr Cys Cys Gly Gly Cys Thr Gly Cys
            20                  25                  30

Thr Ala Ala Cys Ala Ala Ala Gly
        35                  40

<210> SEQ ID NO 44
<211> LENGTH: 20
<212> TYPE: PRT
<213> ORGANISM: Artificial Sequence
<220> FEATURE:
<223> OTHER INFORMATION: Primer

<400> SEQUENCE: 44

Cys Thr Cys Ala Ala Thr Gly Cys Thr Cys Ala Gly Gly Gly Cys
1               5                   10                  15

Gly Thr Thr Thr
            20

<210> SEQ ID NO 45
<211> LENGTH: 22
<212> TYPE: PRT
<213> ORGANISM: Artificial Sequence
<220> FEATURE:
<223> OTHER INFORMATION: Primer

<400> SEQUENCE: 45

Gly Cys Ala Gly Ala Cys Ala Cys Gly Thr Thr Gly Ala Ala Gly Ala
1               5                   10                  15

Gly Thr Cys Cys Ala Gly
            20

<210> SEQ ID NO 46
<211> LENGTH: 21
<212> TYPE: PRT
<213> ORGANISM: Artificial Sequence
<220> FEATURE:
<223> OTHER INFORMATION: Primer

<400> SEQUENCE: 46

Gly Cys Gly Cys Cys Thr Cys Thr Ala Cys Cys Thr Thr Thr Gly
1               5                   10                  15

Ala Thr Gly Thr Cys
            20

<210> SEQ ID NO 47
<211> LENGTH: 36
<212> TYPE: PRT
<213> ORGANISM: Artificial Sequence
<220> FEATURE:

<223> OTHER INFORMATION: Primer

<400> SEQUENCE: 47

Gly Thr Thr Thr Thr Thr Thr Ala Ala Thr Thr Ala Ala Gly Thr Cys
1 5 10 15

Thr Gly Gly Cys Ala Thr Cys Ala Ala Thr Gly Cys Gly Gly Ala Thr
20 25 30

Ala Gly Thr Ala
35

<210> SEQ ID NO 48
<211> LENGTH: 25
<212> TYPE: PRT
<213> ORGANISM: Vibrio cholerae

<400> SEQUENCE: 48

Ala Cys Cys Gly Ala Thr Ala Cys Thr Cys Cys Ala Ala Thr Ala Ala
1 5 10 15

Ala Ala Ala Ala Cys Cys Cys Cys Gly
20 25

<210> SEQ ID NO 49
<211> LENGTH: 39
<212> TYPE: PRT
<213> ORGANISM: Artificial Sequence
<220> FEATURE:
<223> OTHER INFORMATION: Primer

<400> SEQUENCE: 49

Gly Thr Thr Thr Thr Thr Thr Ala Ala Thr Thr Ala Ala Gly Gly Cys
1 5 10 15

Ala Gly Cys Gly Thr Thr Cys Ala Ala Thr Thr Ala Ala Ala Cys Ala
20 25 30

Ala Ala Ala Gly Ala Cys Cys
35

<210> SEQ ID NO 50
<211> LENGTH: 36
<212> TYPE: PRT
<213> ORGANISM: Artificial Sequence
<220> FEATURE:
<223> OTHER INFORMATION: Primer

<400> SEQUENCE: 50

Thr Ala Ala Cys Thr Ala Ala Gly Thr Ala Ala Cys Thr Ala Gly Thr
1 5 10 15

Ala Cys Ala Gly Gly Ala Gly Gly Thr Gly Thr Gly Ala Ala Ala Thr
20 25 30

Gly Ala Cys Thr
35

<210> SEQ ID NO 51
<211> LENGTH: 25
<212> TYPE: PRT
<213> ORGANISM: Artificial Sequence
<220> FEATURE:
<223> OTHER INFORMATION: Primer

<400> SEQUENCE: 51

Ala Thr Gly Ala Gly Ala Gly Thr Ala Cys Gly Gly Gly Ala Ala Thr
1 5 10 15

Ala Cys Ala Ala Cys Gly Ala Gly Cys

```
                        20                  25
```

<210> SEQ ID NO 52
<211> LENGTH: 23
<212> TYPE: PRT
<213> ORGANISM: Vibrio cholerae

<400> SEQUENCE: 52

```
Thr Thr Ala Ala Thr Thr Ala Ala Cys Thr Cys Gly Ala Gly Cys Gly
1               5                   10                  15

Gly Thr Ala Cys Cys Cys Gly
            20
```

<210> SEQ ID NO 53
<211> LENGTH: 36
<212> TYPE: PRT
<213> ORGANISM: Artificial Sequence
<220> FEATURE:
<223> OTHER INFORMATION: Primer

<400> SEQUENCE: 53

```
Gly Thr Thr Thr Thr Thr Thr Gly Gly Thr Ala Cys Cys Thr Cys Thr
1               5                   10                  15

Thr Ala Cys Cys Ala Gly Cys Cys Thr Ala Ala Cys Thr Thr Cys Gly
            20                  25                  30

Ala Thr Cys Ala
        35
```

<210> SEQ ID NO 54
<211> LENGTH: 28
<212> TYPE: PRT
<213> ORGANISM: Artificial Sequence
<220> FEATURE:
<223> OTHER INFORMATION: Primer

<400> SEQUENCE: 54

```
Ala Gly Cys Ala Ala Thr Thr Thr Ala Ala Cys Thr Gly Thr Gly Ala
1               5                   10                  15

Thr Ala Ala Ala Cys Thr Ala Cys Cys Gly Cys Ala
            20                  25
```

<210> SEQ ID NO 55
<211> LENGTH: 18
<212> TYPE: PRT
<213> ORGANISM: Artificial Sequence
<220> FEATURE:
<223> OTHER INFORMATION: Primer

<400> SEQUENCE: 55

```
Thr Cys Thr Thr Thr Thr Thr Gly Cys Ala Thr Gly Cys Gly Gly Cys
1               5                   10                  15

Gly Gly
```

<210> SEQ ID NO 56
<211> LENGTH: 23
<212> TYPE: PRT
<213> ORGANISM: Artificial Sequence
<220> FEATURE:
<223> OTHER INFORMATION: Primer

<400> SEQUENCE: 56

```
Ala Ala Gly Gly Ala Thr Cys Ala Gly Ala Thr Cys Ala Cys Gly Cys
1               5                   10                  15
```

Ala Thr Cys Thr Thr Cys Cys
            20

<210> SEQ ID NO 57
<211> LENGTH: 23
<212> TYPE: PRT
<213> ORGANISM: Artificial Sequence
<220> FEATURE:
<223> OTHER INFORMATION: Primer

<400> SEQUENCE: 57

Thr Thr Gly Cys Thr Cys Ala Ala Thr Cys Ala Ala Thr Cys Ala Cys
1               5                   10                  15

Cys Gly Gly Ala Thr Cys Cys
            20

<210> SEQ ID NO 58
<211> LENGTH: 22
<212> TYPE: PRT
<213> ORGANISM: Artificial Sequence
<220> FEATURE:
<223> OTHER INFORMATION: Primer

<400> SEQUENCE: 58

Gly Gly Ala Thr Cys Cys Gly Gly Thr Gly Ala Thr Thr Gly Ala Thr
1               5                   10                  15

Thr Gly Ala Gly Cys Ala
            20

<210> SEQ ID NO 59
<211> LENGTH: 24
<212> TYPE: PRT
<213> ORGANISM: Artificial Sequence
<220> FEATURE:
<223> OTHER INFORMATION: Primer

<400> SEQUENCE: 59

Thr Gly Thr Cys Ala Thr Cys Thr Gly Gly Cys Ala Ala Ala Thr Gly
1               5                   10                  15

Gly Thr Cys Ala Cys Thr Gly Ala
            20

<210> SEQ ID NO 60
<211> LENGTH: 23
<212> TYPE: PRT
<213> ORGANISM: Artificial Sequence
<220> FEATURE:
<223> OTHER INFORMATION: Primer

<400> SEQUENCE: 60

Cys Thr Gly Thr Thr Gly Cys Ala Thr Gly Gly Gly Cys Ala Thr Ala
1               5                   10                  15

Ala Ala Gly Thr Thr Gly Cys
            20

<210> SEQ ID NO 61
<211> LENGTH: 44
<212> TYPE: PRT
<213> ORGANISM: Artificial Sequence
<220> FEATURE:
<223> OTHER INFORMATION: Primer

<400> SEQUENCE: 61

Gly Cys Gly Cys Gly Thr Ala Cys Ala Gly Gly Ala Gly Gly Thr Gly
1               5                   10                  15

Thr Gly Ala Ala Ala Thr Gly Ala Gly Thr Ala Cys Gly Gly
            20                  25                  30

Gly Ala Ala Thr Ala Cys Ala Ala Cys Gly Ala Gly
        35                  40

<210> SEQ ID NO 62
<211> LENGTH: 26
<212> TYPE: PRT
<213> ORGANISM: Artificial Sequence
<220> FEATURE:
<223> OTHER INFORMATION: Primer

<400> SEQUENCE: 62

Gly Cys Ala Thr Ala Ala Ala Gly Cys Thr Thr Gly Cys Thr Cys Ala
1               5                   10                  15

Ala Thr Cys Ala Ala Thr Cys Ala Cys Cys
            20                  25

<210> SEQ ID NO 63
<211> LENGTH: 37
<212> TYPE: PRT
<213> ORGANISM: Artificial Sequence
<220> FEATURE:
<223> OTHER INFORMATION: Primer

<400> SEQUENCE: 63

Gly Thr Thr Thr Thr Thr Thr Ala Ala Thr Ala Ala Cys Thr Thr
1               5                   10                  15

Thr Thr Cys Cys Ala Gly Gly Cys Thr Gly Gly Ala Thr Thr Gly
            20                  25                  30

Thr Ala Gly Gly Gly
        35

<210> SEQ ID NO 64
<211> LENGTH: 24
<212> TYPE: PRT
<213> ORGANISM: Artificial Sequence
<220> FEATURE:
<223> OTHER INFORMATION: Primer

<400> SEQUENCE: 64

Cys Thr Thr Thr Thr Thr Cys Cys Ala Gly Gly Cys Thr Gly Gly Ala
1               5                   10                  15

Thr Thr Gly Thr Ala Gly Gly Gly
            20

<210> SEQ ID NO 65
<211> LENGTH: 40
<212> TYPE: PRT
<213> ORGANISM: Artificial Sequence
<220> FEATURE:
<223> OTHER INFORMATION: Primer

<400> SEQUENCE: 65

Gly Thr Thr Thr Thr Thr Thr Ala Ala Thr Thr Ala Ala Ala Gly Cys
1               5                   10                  15

Ala Thr Cys Ala Thr Cys Cys Cys Cys Thr Thr Cys Gly Cys Thr Thr
            20                  25                  30

Ala Thr Thr Gly Ala Cys Ala Thr
        35                  40

<210> SEQ ID NO 66

```
<211> LENGTH: 27
<212> TYPE: PRT
<213> ORGANISM: Artificial Sequence
<220> FEATURE:
<223> OTHER INFORMATION: Primer

<400> SEQUENCE: 66

Ala Gly Cys Ala Thr Cys Ala Thr Cys Cys Cys Thr Cys Gly
1               5                   10                  15

Cys Thr Thr Ala Thr Thr Gly Ala Cys Ala Thr
            20                  25

<210> SEQ ID NO 67
<211> LENGTH: 39
<212> TYPE: PRT
<213> ORGANISM: Artificial Sequence
<220> FEATURE:
<223> OTHER INFORMATION: Primer

<400> SEQUENCE: 67

Gly Thr Thr Thr Thr Thr Thr Ala Ala Thr Thr Ala Ala Gly Gly Thr
1               5                   10                  15

Thr Gly Thr Thr Gly Thr Gly Thr Ala Gly Ala Gly Thr Thr Thr Ala
            20                  25                  30

Ala Cys Thr Gly Gly Cys Cys
        35

<210> SEQ ID NO 68
<211> LENGTH: 23
<212> TYPE: PRT
<213> ORGANISM: Artificial Sequence
<220> FEATURE:
<223> OTHER INFORMATION: Primer

<400> SEQUENCE: 68

Gly Ala Ala Thr Cys Cys Cys Thr Gly Cys Thr Thr Cys Gly Thr Cys
1               5                   10                  15

Cys Ala Thr Thr Thr Gly Ala
            20

<210> SEQ ID NO 69
<211> LENGTH: 35
<212> TYPE: PRT
<213> ORGANISM: Artificial Sequence
<220> FEATURE:
<223> OTHER INFORMATION: Primer

<400> SEQUENCE: 69

Gly Thr Thr Thr Thr Thr Thr Ala Ala Thr Thr Ala Ala Cys Thr Ala
1               5                   10                  15

Cys Thr Cys Cys Gly Thr Cys Ala Ala Gly Cys Cys Gly Thr Cys Ala
            20                  25                  30

Ala Thr Thr
        35

<210> SEQ ID NO 70
<211> LENGTH: 23
<212> TYPE: PRT
<213> ORGANISM: Artificial Sequence
<220> FEATURE:
<223> OTHER INFORMATION: Primer

<400> SEQUENCE: 70

Cys Gly Cys Gly Thr Thr Ala Thr Cys Gly Cys Thr Cys Thr Gly Ala
```

```
                1               5                  10                 15
Ala Ala Gly Thr Ala Cys Ala
            20
```

<210> SEQ ID NO 71
<211> LENGTH: 35
<212> TYPE: PRT
<213> ORGANISM: Artificial Sequence
<220> FEATURE:
<223> OTHER INFORMATION: Primer

<400> SEQUENCE: 71

```
Gly Thr Thr Thr Thr Thr Thr Ala Ala Thr Thr Ala Ala Cys Cys Ala
1               5                  10                 15

Ala Thr Thr Cys Cys Thr Gly Cys Ala Gly Gly Ala Thr Thr Thr Thr
            20                  25                 30

Gly Cys Gly
        35
```

<210> SEQ ID NO 72
<211> LENGTH: 33
<212> TYPE: PRT
<213> ORGANISM: Artificial Sequence
<220> FEATURE:
<223> OTHER INFORMATION: Primer

<400> SEQUENCE: 72

```
Ala Thr Gly Ala Ala Thr Thr Thr Thr Gly Gly Thr Ala Ala Cys Gly
1               5                  10                 15

Thr Cys Ala Thr Ala Ala Gly Ala Cys Gly Ala Cys Thr Thr Ala Gly
            20                  25                 30

Gly
```

<210> SEQ ID NO 73
<211> LENGTH: 29
<212> TYPE: PRT
<213> ORGANISM: Artificial Sequence
<220> FEATURE:
<223> OTHER INFORMATION: Primer

<400> SEQUENCE: 73

```
Cys Ala Thr Cys Thr Thr Ala Thr Ala Ala Thr Cys Cys Gly Thr Cys
1               5                  10                 15

Gly Ala Ala Ala Ala Ala Ala Gly Thr Cys Thr Gly Gly
            20                  25
```

<210> SEQ ID NO 74
<211> LENGTH: 24
<212> TYPE: PRT
<213> ORGANISM: Artificial Sequence
<220> FEATURE:
<223> OTHER INFORMATION: Primer

<400> SEQUENCE: 74

```
Gly Gly Cys Cys Ala Gly Thr Thr Ala Ala Cys Thr Cys Thr Ala
1               5                  10                 15

Cys Ala Cys Ala Ala Cys Ala Ala
            20
```

<210> SEQ ID NO 75
<211> LENGTH: 22
<212> TYPE: PRT
<213> ORGANISM: Artificial Sequence
<220> FEATURE:
<223> OTHER INFORMATION: Primer

<400> SEQUENCE: 75

Cys Gly Cys Ala Ala Ala Ala Thr Cys Thr Gly Cys Ala Gly Gly
1               5                   10                  15

Ala Ala Thr Thr Gly Gly
            20

<210> SEQ ID NO 76
<211> LENGTH: 24
<212> TYPE: PRT
<213> ORGANISM: Artificial Sequence
<220> FEATURE:
<223> OTHER INFORMATION: Primer

<400> SEQUENCE: 76

Ala Thr Gly Ala Ala Ala Cys Ala Thr Cys Ala Thr Cys Ala Cys
1               5                   10                  15

Ala Thr Cys Ala Cys Cys Ala Cys
            20

<210> SEQ ID NO 77
<211> LENGTH: 23
<212> TYPE: PRT
<213> ORGANISM: Artificial Sequence
<220> FEATURE:
<223> OTHER INFORMATION: Primer

<400> SEQUENCE: 77

Gly Thr Gly Gly Ala Gly Cys Thr Cys Cys Ala Thr Thr Thr Cys
1               5                   10                  15

Ala Cys Thr Thr Thr Thr Cys
            20

<210> SEQ ID NO 78
<211> LENGTH: 22
<212> TYPE: PRT
<213> ORGANISM: Vibrio cholerae

<400> SEQUENCE: 78

Cys Gly Cys Thr Cys Thr Ala Gly Ala Ala Cys Thr Ala Gly Thr
1               5                   10                  15

Gly Ala Thr Cys Cys Cys
            20

<210> SEQ ID NO 79
<211> LENGTH: 23
<212> TYPE: PRT
<213> ORGANISM: Artificial Sequence
<220> FEATURE:
<223> OTHER INFORMATION: Primer

<400> SEQUENCE: 79

Ala Gly Gly Ala Gly Gly Thr Gly Thr Gly Ala Ala Gly Thr Gly Thr
1               5                   10                  15

Gly Thr Gly Ala Thr Thr Thr
            20

<210> SEQ ID NO 80
<211> LENGTH: 22
<212> TYPE: PRT
<213> ORGANISM: Artificial Sequence
<220> FEATURE:

<223> OTHER INFORMATION: Primer

<400> SEQUENCE: 80

Cys Thr Cys Ala Ala Thr Cys Ala Ala Thr Cys Ala Cys Cys Gly Gly
1               5                   10                  15

Ala Thr Cys Cys Thr Gly
            20

<210> SEQ ID NO 81
<211> LENGTH: 29
<212> TYPE: PRT
<213> ORGANISM: Artificial Sequence
<220> FEATURE:
<223> OTHER INFORMATION: Primer

<400> SEQUENCE: 81

Gly Thr Cys Thr Cys Ala Thr Gly Ala Gly Cys Gly Gly Ala Thr Ala
1               5                   10                  15

Cys Ala Thr Ala Thr Thr Thr Gly Ala Ala Thr Gly Thr
            20                  25

<210> SEQ ID NO 82
<211> LENGTH: 30
<212> TYPE: PRT
<213> ORGANISM: Artificial Sequence
<220> FEATURE:
<223> OTHER INFORMATION: Primer

<400> SEQUENCE: 82

Gly Thr Thr Thr Thr Gly Gly Thr Ala Cys Cys Thr Thr Thr Ala Thr
1               5                   10                  15

Ala Ala Ala Gly Gly Gly Gly Cys Thr Gly Cys Thr Gly Gly
            20                  25                  30

<210> SEQ ID NO 83
<211> LENGTH: 21
<212> TYPE: PRT
<213> ORGANISM: Artificial Sequence
<220> FEATURE:
<223> OTHER INFORMATION: Primer

<400> SEQUENCE: 83

Thr Cys Ala Thr Cys Gly Ala Gly Thr Gly Cys Cys Thr Thr Thr
1               5                   10                  15

Gly Gly Cys Thr Gly
            20

<210> SEQ ID NO 84
<211> LENGTH: 20
<212> TYPE: PRT
<213> ORGANISM: Artificial Sequence
<220> FEATURE:
<223> OTHER INFORMATION: Primer

<400> SEQUENCE: 84

Thr Thr Cys Ala Cys Ala Cys Cys Thr Cys Cys Thr Gly Thr Gly Gly
1               5                   10                  15

Ala Gly Cys Thr
            20

<210> SEQ ID NO 85
<211> LENGTH: 30
<212> TYPE: PRT
<213> ORGANISM: Artificial Sequence
<220> FEATURE:
<223> OTHER INFORMATION: Primer

<400> SEQUENCE: 85

Thr Thr Ala Ala Thr Thr Ala Ala Cys Cys Ala Ala Thr Thr Cys Cys
1               5                   10                  15

Thr Gly Cys Ala Gly Gly Ala Thr Thr Thr Gly Cys Gly
            20                  25                  30

<210> SEQ ID NO 86
<211> LENGTH: 43
<212> TYPE: PRT
<213> ORGANISM: Artificial Sequence
<220> FEATURE:
<223> OTHER INFORMATION: Primer

<400> SEQUENCE: 86

Gly Gly Thr Ala Thr Ala Thr Cys Thr Cys Thr Thr Cys Thr Thr
1               5                   10                  15

Ala Ala Ala Gly Thr Thr Ala Ala Cys Ala Ala Ala Thr Thr
            20                  25                  30

Ala Thr Thr Thr Cys Thr Ala Gly Ala Gly Gly
        35                  40

<210> SEQ ID NO 87
<211> LENGTH: 27
<212> TYPE: PRT
<213> ORGANISM: Artificial Sequence
<220> FEATURE:
<223> OTHER INFORMATION: Primer

<400> SEQUENCE: 87

Gly Thr Thr Thr Thr Thr Thr Gly Gly Ala Thr Cys Cys Gly Gly Cys
1               5                   10                  15

Thr Gly Cys Thr Ala Ala Cys Ala Ala Ala Gly
            20                  25

<210> SEQ ID NO 88
<211> LENGTH: 32
<212> TYPE: PRT
<213> ORGANISM: Artificial Sequence
<220> FEATURE:
<223> OTHER INFORMATION: Primer

<400> SEQUENCE: 88

Gly Thr Thr Thr Thr Thr Thr Gly Gly Ala Thr Cys Cys Ala Ala Ala
1               5                   10                  15

Ala Gly Gly Cys Ala Cys Thr Cys Gly Ala Thr Gly Ala Cys Thr Ala
            20                  25                  30

<210> SEQ ID NO 89
<211> LENGTH: 19
<212> TYPE: PRT
<213> ORGANISM: Artificial Sequence
<220> FEATURE:
<223> OTHER INFORMATION: Primer

<400> SEQUENCE: 89

Gly Ala Ala Ala Thr Gly Gly Gly Cys Ala Gly Cys Ala Gly Cys Cys
1               5                   10                  15

Ala Thr Cys

<210> SEQ ID NO 90

```
<211> LENGTH: 34
<212> TYPE: PRT
<213> ORGANISM: Artificial Sequence
<220> FEATURE:
<223> OTHER INFORMATION: Primer

<400> SEQUENCE: 90

Cys Ala Thr Gly Ala Thr Gly Ala Ala Thr Thr Cys Thr Cys Cys Thr
1               5                   10                  15

Thr Ala Gly Thr Ala Ala Ala Gly Thr Thr Ala Ala Ala Ala Thr Ala
            20                  25                  30

Cys Cys

<210> SEQ ID NO 91
<211> LENGTH: 21
<212> TYPE: PRT
<213> ORGANISM: Artificial Sequence
<220> FEATURE:
<223> OTHER INFORMATION: Primer

<400> SEQUENCE: 91

Gly Cys Ala Gly Ala Ala Ala Thr Cys Gly Gly Thr Ala Cys Thr Gly
1               5                   10                  15

Gly Cys Thr Thr Thr
            20

<210> SEQ ID NO 92
<211> LENGTH: 25
<212> TYPE: PRT
<213> ORGANISM: Artificial Sequence
<220> FEATURE:
<223> OTHER INFORMATION: Primer

<400> SEQUENCE: 92

Gly Cys Thr Cys Thr Gly Ala Ala Ala Gly Thr Ala Cys Ala Gly Ala
1               5                   10                  15

Thr Cys Cys Thr Cys Ala Gly Thr Gly
            20                  25

<210> SEQ ID NO 93
<211> LENGTH: 29
<212> TYPE: PRT
<213> ORGANISM: Artificial Sequence
<220> FEATURE:
<223> OTHER INFORMATION: Primer

<400> SEQUENCE: 93

Thr Gly Ala Thr Ala Ala Ala Ala Cys Gly Cys Ala Gly Cys Ala Gly
1               5                   10                  15

Thr Thr Ala Thr Ala Ala Thr Thr Thr Gly Cys Gly Ala
            20                  25

<210> SEQ ID NO 94
<211> LENGTH: 20
<212> TYPE: PRT
<213> ORGANISM: Artificial Sequence
<220> FEATURE:
<223> OTHER INFORMATION: Primer

<400> SEQUENCE: 94

Thr Thr Cys Ala Cys Ala Cys Cys Thr Cys Thr Gly Cys Ala Gly
1               5                   10                  15

Gly Thr Ala Cys
            20
```

```
<210> SEQ ID NO 95
<211> LENGTH: 32
<212> TYPE: PRT
<213> ORGANISM: Artificial Sequence
<220> FEATURE:
<223> OTHER INFORMATION: Primer

<400> SEQUENCE: 95

Ala Thr Gly Ala Thr Gly Ala Ala Thr Thr Thr Gly Gly Thr Ala
1               5                   10                  15

Ala Cys Gly Thr Cys Ala Thr Ala Ala Gly Ala Cys Gly Ala Cys Thr
            20                  25                  30

<210> SEQ ID NO 96
<211> LENGTH: 22
<212> TYPE: PRT
<213> ORGANISM: Vibrio cholerae

<400> SEQUENCE: 96

Cys Cys Ala Cys Gly Gly Ala Ala Thr Ala Gly Gly Ala Gly Gly Thr
1               5                   10                  15

Gly Thr Thr Thr Ala Gly
            20

<210> SEQ ID NO 97
<211> LENGTH: 21
<212> TYPE: PRT
<213> ORGANISM: Artificial Sequence
<220> FEATURE:
<223> OTHER INFORMATION: Primer

<400> SEQUENCE: 97

Gly Ala Gly Gly Gly Ala Thr Ala Thr Cys Cys Ala Thr Ala Cys
1               5                   10                  15

Gly Cys Cys Ala Gly
            20

<210> SEQ ID NO 98
<211> LENGTH: 42
<212> TYPE: PRT
<213> ORGANISM: Artificial Sequence
<220> FEATURE:
<223> OTHER INFORMATION: Primer

<400> SEQUENCE: 98

Cys Thr Gly Thr Cys Thr Cys Thr Ala Thr Ala Cys Ala Cys Ala
1               5                   10                  15

Thr Cys Thr Ala Thr Thr Cys Cys Ala Thr Gly Thr Cys Ala Gly
            20                  25                  30

Cys Cys Gly Thr Thr Ala Ala Gly Thr Gly
        35                  40

<210> SEQ ID NO 99
<211> LENGTH: 42
<212> TYPE: PRT
<213> ORGANISM: Artificial Sequence
<220> FEATURE:
<223> OTHER INFORMATION: Primer

<400> SEQUENCE: 99

Cys Thr Gly Thr Cys Thr Cys Thr Thr Ala Thr Ala Cys Ala Cys Ala
1               5                   10                  15
```

Thr Cys Thr Ala Gly Gly Gly Cys Ala Cys Ala Ala Thr Ala Ala
            20                  25                  30

Cys Thr Gly Cys Cys Thr Thr Ala Ala Ala
        35                  40

<210> SEQ ID NO 100
<211> LENGTH: 39
<212> TYPE: PRT
<213> ORGANISM: Artificial Sequence
<220> FEATURE:
<223> OTHER INFORMATION: Primer

<400> SEQUENCE: 100

Cys Thr Gly Thr Cys Thr Cys Thr Thr Ala Thr Ala Cys Ala Cys Ala
1               5                   10                  15

Thr Cys Thr Thr Cys Thr Ala Gly Ala Ala Gly Ala Ala Gly Cys Thr
            20                  25                  30

Thr Gly Gly Gly Ala Thr Cys
        35

<210> SEQ ID NO 101
<211> LENGTH: 38
<212> TYPE: PRT
<213> ORGANISM: Artificial Sequence
<220> FEATURE:
<223> OTHER INFORMATION: Primer

<400> SEQUENCE: 101

Cys Thr Gly Thr Cys Thr Cys Thr Thr Ala Thr Ala Cys Ala Cys Ala
1               5                   10                  15

Thr Cys Thr Cys Thr Gly Thr Thr Gly Cys Ala Thr Gly Gly Gly Cys
            20                  25                  30

Ala Thr Ala Ala Ala Gly
        35

<210> SEQ ID NO 102
<211> LENGTH: 41
<212> TYPE: PRT
<213> ORGANISM: Artificial Sequence
<220> FEATURE:
<223> OTHER INFORMATION: Primer

<400> SEQUENCE: 102

Cys Thr Gly Thr Cys Thr Cys Thr Thr Ala Thr Ala Cys Ala Cys Ala
1               5                   10                  15

Thr Cys Thr Cys Ala Ala Ala Thr Gly Gly Ala Cys Gly Ala Ala Gly
            20                  25                  30

Cys Ala Gly Gly Gly Ala Thr Thr Cys
        35                  40

<210> SEQ ID NO 103
<211> LENGTH: 42
<212> TYPE: PRT
<213> ORGANISM: Artificial Sequence
<220> FEATURE:
<223> OTHER INFORMATION: Primer

<400> SEQUENCE: 103

Cys Thr Gly Thr Cys Thr Cys Thr Thr Ala Thr Ala Cys Ala Cys Ala
1               5                   10                  15

Thr Cys Thr Thr Cys Cys Cys Thr Gly Thr Ala Ala Gly Thr Ala
            20                  25                  30

Thr Cys Thr Thr Cys Cys Thr Gly Gly Cys
        35                  40

<210> SEQ ID NO 104
<211> LENGTH: 24
<212> TYPE: PRT
<213> ORGANISM: Artificial Sequence
<220> FEATURE:
<223> OTHER INFORMATION: Primer

<400> SEQUENCE: 104

Gly Cys Ala Thr Cys Ala Thr Cys Cys Cys Thr Cys Gly Cys
1               5                   10                  15

Thr Thr Ala Thr Thr Gly Ala Cys
            20

<210> SEQ ID NO 105
<211> LENGTH: 35
<212> TYPE: PRT
<213> ORGANISM: Artificial Sequence
<220> FEATURE:
<223> OTHER INFORMATION: Primer

<400> SEQUENCE: 105

Gly Ala Ala Thr Ala Cys Ala Cys Thr Cys Cys Thr Thr Gly Thr Ala
1               5                   10                  15

Ala Gly Thr Gly Ala Thr Thr Gly Thr Thr Ala Thr Ala Ala Gly Gly
            20                  25                  30

Ala Gly Cys
        35

<210> SEQ ID NO 106
<211> LENGTH: 20
<212> TYPE: PRT
<213> ORGANISM: Artificial Sequence
<220> FEATURE:
<223> OTHER INFORMATION: Primer

<400> SEQUENCE: 106

Thr Cys Cys Gly Ala Gly Thr Ala Thr Thr Gly Cys Gly Cys Gly Ala
1               5                   10                  15

Gly Cys Thr Gly
            20

<210> SEQ ID NO 107
<211> LENGTH: 20
<212> TYPE: PRT
<213> ORGANISM: Artificial Sequence
<220> FEATURE:
<223> OTHER INFORMATION: Primer

<400> SEQUENCE: 107

Gly Thr Thr Thr Gly Thr Ala Cys Thr Thr Ala Cys Cys Gly Ala
1               5                   10                  15

Ala Cys Gly Cys
            20

<210> SEQ ID NO 108
<211> LENGTH: 20
<212> TYPE: PRT
<213> ORGANISM: Artificial Sequence
<220> FEATURE:
<223> OTHER INFORMATION: Primer

<400> SEQUENCE: 108

Gly Ala Thr Thr Thr Thr Cys Ala Cys Cys Thr Gly Cys Cys
1               5                   10                  15

Ala Cys Cys Thr
            20

<210> SEQ ID NO 109
<211> LENGTH: 23
<212> TYPE: PRT
<213> ORGANISM: Artificial Sequence
<220> FEATURE:
<223> OTHER INFORMATION: Primer

<400> SEQUENCE: 109

Cys Cys Cys Gly Ala Thr Cys Cys Ala Ala Gly Cys Thr Thr Cys
1               5                   10                  15

Thr Thr Cys Thr Ala Gly Ala
            20

<210> SEQ ID NO 110
<211> LENGTH: 21
<212> TYPE: PRT
<213> ORGANISM: Artificial Sequence
<220> FEATURE:
<223> OTHER INFORMATION: Primer

<400> SEQUENCE: 110

Cys Thr Gly Cys Cys Ala Thr Cys Ala Thr Cys Gly Ala Gly Cys Thr
1               5                   10                  15

Ala Cys Thr Gly Gly
            20

<210> SEQ ID NO 111
<211> LENGTH: 23
<212> TYPE: PRT
<213> ORGANISM: Artificial Sequence
<220> FEATURE:
<223> OTHER INFORMATION: Primer

<400> SEQUENCE: 111

Gly Thr Thr Gly Ala Thr Gly Ala Thr Gly Ala Gly Cys Ala Cys Thr
1               5                   10                  15

Gly Gly Gly Ala Ala Gly Cys
            20

<210> SEQ ID NO 112
<211> LENGTH: 20
<212> TYPE: PRT
<213> ORGANISM: Artificial Sequence
<220> FEATURE:
<223> OTHER INFORMATION: Primer

<400> SEQUENCE: 112

Ala Gly Ala Cys Ala Gly Gly Gly Cys Ala Cys Ala Cys Gly Ala Thr
1               5                   10                  15

Ala Cys Cys Ala
            20

<210> SEQ ID NO 113
<211> LENGTH: 20
<212> TYPE: PRT
<213> ORGANISM: Artificial Sequence
<220> FEATURE:
<223> OTHER INFORMATION: Primer

```
<400> SEQUENCE: 113

Gly Ala Cys Cys Cys Ala Thr Thr Thr Cys Thr Ala Ala Ala Cys Gly
1               5                   10                  15

Cys Gly Cys Thr
            20

<210> SEQ ID NO 114
<211> LENGTH: 20
<212> TYPE: PRT
<213> ORGANISM: Artificial Sequence
<220> FEATURE:
<223> OTHER INFORMATION: Primer

<400> SEQUENCE: 114

Gly Cys Cys Gly Gly Cys Ala Cys Ala Ala Cys Thr Gly Thr Ala Gly
1               5                   10                  15

Ala Ala Ala Thr
            20

<210> SEQ ID NO 115
<211> LENGTH: 21
<212> TYPE: PRT
<213> ORGANISM: Artificial Sequence
<220> FEATURE:
<223> OTHER INFORMATION: Primer

<400> SEQUENCE: 115

Ala Cys Cys Ala Thr Thr Thr Cys Thr Ala Cys Gly Gly Ala Cys
1               5                   10                  15

Ala Ala Gly Ala Cys
            20

<210> SEQ ID NO 116
<211> LENGTH: 21
<212> TYPE: PRT
<213> ORGANISM: Artificial Sequence
<220> FEATURE:
<223> OTHER INFORMATION: Primer

<400> SEQUENCE: 116

Cys Ala Cys Ala Thr Thr Gly Gly Thr Cys Thr Cys Gly Ala Ala Gly
1               5                   10                  15

Gly Ala Thr Cys Cys
            20

<210> SEQ ID NO 117
<211> LENGTH: 21
<212> TYPE: PRT
<213> ORGANISM: Artificial Sequence
<220> FEATURE:
<223> OTHER INFORMATION: Primer

<400> SEQUENCE: 117

Thr Gly Ala Thr Thr Gly Thr Gly Cys Thr Gly Gly Thr Thr Gly Thr
1               5                   10                  15

Cys Gly Gly Thr Gly
            20

<210> SEQ ID NO 118
<211> LENGTH: 28
<212> TYPE: PRT
<213> ORGANISM: Artificial Sequence
<220> FEATURE:
<223> OTHER INFORMATION: Primer
```

<400> SEQUENCE: 118

Cys Cys Ala Thr Thr Thr Cys Gly Thr Gly Ala Gly Gly Thr
1               5                   10                  15

Gly Ala Thr Gly Thr Ala Cys Thr Thr Cys Thr Cys
            20                  25

<210> SEQ ID NO 119
<211> LENGTH: 27
<212> TYPE: PRT
<213> ORGANISM: Artificial Sequence
<220> FEATURE:
<223> OTHER INFORMATION: Primer

<400> SEQUENCE: 119

Gly Thr Cys Ala Thr Thr Thr Cys Ala Ala Cys Gly Gly Thr Thr
1               5                   10                  15

Gly Cys Thr Cys Ala Ala Cys Thr Cys Ala Cys
            20                  25

<210> SEQ ID NO 120
<211> LENGTH: 19
<212> TYPE: PRT
<213> ORGANISM: Artificial Sequence
<220> FEATURE:
<223> OTHER INFORMATION: Primer

<400> SEQUENCE: 120

Thr Ala Ala Gly Cys Gly Ala Cys Thr Gly Gly Cys Cys Ala Gly
1               5                   10                  15

Ala Ala Cys

<210> SEQ ID NO 121
<211> LENGTH: 23
<212> TYPE: PRT
<213> ORGANISM: Artificial Sequence
<220> FEATURE:
<223> OTHER INFORMATION: Primer

<400> SEQUENCE: 121

Thr Cys Gly Ala Gly Gly Ala Gly Cys Thr Gly Gly Cys Cys Thr Ala
1               5                   10                  15

Thr Ala Ala Ala Gly Ala Cys
            20

<210> SEQ ID NO 122
<211> LENGTH: 20
<212> TYPE: PRT
<213> ORGANISM: Artificial Sequence
<220> FEATURE:
<223> OTHER INFORMATION: Primer

<400> SEQUENCE: 122

Ala Ala Ala Gly Cys Gly Ala Ala Cys Ala Gly Gly Cys Thr Cys Cys
1               5                   10                  15

Ala Thr Cys Cys
            20

<210> SEQ ID NO 123
<211> LENGTH: 32
<212> TYPE: PRT
<213> ORGANISM: Artificial Sequence
<220> FEATURE:
<223> OTHER INFORMATION: Primer

```
<400> SEQUENCE: 123

Gly Cys Thr Gly Ala Gly Ala Cys Gly Ala Ala Ala Ala Cys Ala
1               5                   10                  15

Thr Ala Thr Thr Cys Thr Cys Ala Ala Thr Ala Ala Cys Cys Cys
                20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Primer

<400> SEQUENCE: 124

Gly Gly Cys Ala Gly Thr Thr Cys Thr Ala Cys Ala Cys Ala Thr
1               5                   10                  15

Ala Thr Ala Thr Thr Cys Gly Cys Ala Ala Gly Ala Thr Gly
                20                  25                  30

<210> SEQ ID NO 125
<211> LENGTH: 27
<212> TYPE: PRT
<213> ORGANISM: Artificial Sequence
<220> FEATURE:
<223> OTHER INFORMATION: Primer

<400> SEQUENCE: 125

Gly Ala Thr Thr Ala Cys Thr Gly Gly Cys Thr Thr Ala Cys Thr Ala
1               5                   10                  15

Thr Gly Thr Thr Gly Gly Cys Ala Cys Thr Gly
                20                  25

<210> SEQ ID NO 126
<211> LENGTH: 22
<212> TYPE: PRT
<213> ORGANISM: Artificial Sequence
<220> FEATURE:
<223> OTHER INFORMATION: Primer

<400> SEQUENCE: 126

Gly Thr Cys Ala Gly Cys Ala Ala Cys Ala Cys Cys Thr Thr Cys Thr
1               5                   10                  15

Thr Cys Ala Cys Gly Ala
                20

<210> SEQ ID NO 127
<211> LENGTH: 25
<212> TYPE: PRT
<213> ORGANISM: Artificial Sequence
<220> FEATURE:
<223> OTHER INFORMATION: Primer

<400> SEQUENCE: 127

Thr Cys Thr Ala Ala Ala Gly Ala Gly Thr Cys Gly Ala Thr Gly Thr
1               5                   10                  15

Gly Thr Thr Cys Ala Cys Thr Gly Cys
                20                  25

<210> SEQ ID NO 128
<211> LENGTH: 26
<212> TYPE: PRT
<213> ORGANISM: Artificial Sequence
<220> FEATURE:
```

<223> OTHER INFORMATION: Primer

<400> SEQUENCE: 128

Cys Cys Ala Ala Gly Ala Gly Gly Thr Ala Gly Ala Thr Thr Gly
1               5                   10                  15

Gly Ala Cys Ala Gly Ala Gly Ala Thr Cys
            20                  25

<210> SEQ ID NO 129
<211> LENGTH: 24
<212> TYPE: PRT
<213> ORGANISM: Artificial Sequence
<220> FEATURE:
<223> OTHER INFORMATION: Primer

<400> SEQUENCE: 129

Ala Ala Thr Ala Cys Cys Ala Thr Ala Gly Ala Ala Cys Ala Gly Thr
1               5                   10                  15

Cys Gly Cys Thr Cys Cys Thr Cys
            20

<210> SEQ ID NO 130
<211> LENGTH: 24
<212> TYPE: PRT
<213> ORGANISM: Artificial Sequence
<220> FEATURE:
<223> OTHER INFORMATION: Primer

<400> SEQUENCE: 130

Thr Thr Gly Cys Thr Thr Thr Ala Thr Cys Gly Ala Thr Cys Ala Gly
1               5                   10                  15

Cys Thr Cys Gly Thr Thr Cys Thr
            20

<210> SEQ ID NO 131
<211> LENGTH: 20
<212> TYPE: PRT
<213> ORGANISM: Artificial Sequence
<220> FEATURE:
<223> OTHER INFORMATION: Primer

<400> SEQUENCE: 131

Cys Gly Thr Gly Ala Gly Cys Gly Thr Ala Thr Thr Cys Cys Ala Gly
1               5                   10                  15

Thr Gly Thr Cys
            20

<210> SEQ ID NO 132
<211> LENGTH: 20
<212> TYPE: PRT
<213> ORGANISM: Artificial Sequence
<220> FEATURE:
<223> OTHER INFORMATION: Primer

<400> SEQUENCE: 132

Ala Gly Ala Ala Ala Thr Cys Gly Cys Gly Thr Gly Cys Thr Thr Gly
1               5                   10                  15

Thr Ala Cys Ala
            20

<210> SEQ ID NO 133
<211> LENGTH: 22
<212> TYPE: PRT
<213> ORGANISM: Artificial Sequence

```
<220> FEATURE:
<223> OTHER INFORMATION: Primer

<400> SEQUENCE: 133

Ala Thr Ala Thr Thr Gly Cys Gly Gly Cys Cys Gly Gly Thr Gly Ala
1               5                   10                  15

Cys Ala Ala Ala Ala Gly
            20

<210> SEQ ID NO 134
<211> LENGTH: 19
<212> TYPE: PRT
<213> ORGANISM: Artificial Sequence
<220> FEATURE:
<223> OTHER INFORMATION: Primer

<400> SEQUENCE: 134

Cys Thr Gly Cys Cys Cys Ala Thr Cys Thr Thr Gly Ala Cys Cys Cys
1               5                   10                  15

Cys Thr Thr
```